US009675561B2

(12) United States Patent
Bencherif et al.

(10) Patent No.: US 9,675,561 B2
(45) Date of Patent: Jun. 13, 2017

(54) INJECTABLE CRYOGEL VACCINE DEVICES AND METHODS OF USE THEREOF

(71) Applicant: President and Fellows of Harvard College, Cambridge, MA (US)

(72) Inventors: Sidi A. Bencherif, Dorchester, MA (US); Roger Warren Sands, Chicago, IL (US); Sandeep T. Koshy, Boston, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/166,689

(22) Filed: Jan. 28, 2014

(65) Prior Publication Data

US 2014/0227327 A1 Aug. 14, 2014

Related U.S. Application Data

(63) Continuation-in-part of application No. 14/112,096, filed as application No. PCT/US2012/035505 on Apr. 27, 2012.

(60) Provisional application No. 61/480,237, filed on Apr. 28, 2011, provisional application No. 61/757,509, filed on Jan. 28, 2013, provisional application No. 61/915,985, filed on Dec. 13, 2013.

(51) Int. Cl.
| | | |
|---|---|---|
| A61K 9/70 | (2006.01) | |
| A61K 47/36 | (2006.01) | |
| A61K 47/42 | (2017.01) | |
| A61K 39/39 | (2006.01) | |
| A61K 9/00 | (2006.01) | |
| A61K 39/00 | (2006.01) | |
| A61L 27/26 | (2006.01) | |
| A61L 27/50 | (2006.01) | |
| A61L 27/54 | (2006.01) | |
| A61L 27/56 | (2006.01) | |

(52) U.S. Cl.
CPC .......... *A61K 9/7007* (2013.01); *A61K 9/0024* (2013.01); *A61K 39/0011* (2013.01); *A61K 39/39* (2013.01); *A61K 47/36* (2013.01); *A61K 47/42* (2013.01); *A61L 27/26* (2013.01); *A61L 27/50* (2013.01); *A61L 27/54* (2013.01); *A61L 27/56* (2013.01); *A61K 2039/5152* (2013.01); *A61K 2039/55522* (2013.01); *A61K 2039/55561* (2013.01); *A61L 2300/252* (2013.01); *A61L 2300/258* (2013.01); *A61L 2400/06* (2013.01)

(58) Field of Classification Search
CPC ...... A61K 9/7007; A61K 47/42; A61K 47/36; A61K 39/0011; A61K 2039/5152; A61K 2039/55522; A61K 2039/55561; A61K 39/39; A61L 27/26; A61L 27/50; A61L 27/54; A61L 2300/258; A61L 2300/252; A61L 27/56; C08L 5/04; C08L 89/06
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

Kathuria et al ("Synthesis and characterization of elastic and macroporous chitosan-gelatin cryogels for tissue engineering," Acta Biomaterialia 5 (2009) 406-418, Available online Jul. 25, 2008).*
"Antigens and Receptors." *Immunology*. Doan et al., eds. Philadelphia: Wolters Kluwer/Lippincott Williams & Wilsons. (2008):11-23.
"Collagen: The Fibrous Proteins of the Matrix." *Molecular Cell Biology*. Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
"Wound Management: Past, Present, and Future." *Clinicians' Pocket Guide to Chronic Wound Repair*. Mulder et al., eds. Springhouse, PA: Springhouse Corporation. (1998):85-90.

(Continued)

*Primary Examiner* — Suzanne Ziska
(74) *Attorney, Agent, or Firm* — Mintz Levin Cohn Ferris Glovsky and Popeo, P.C.

(57) ABSTRACT

The invention provides polymer compositions for cell and drug delivery.

39 Claims, 59 Drawing Sheets

(56) References Cited

U.S. PATENT DOCUMENTS

| | | | |
|---|---|---|---|
| 7,427,602 | B1 | 9/2008 | Shea et al. |
| 7,575,759 | B2 | 8/2009 | Murphy et al. |
| 7,687,241 | B2 | 3/2010 | Chen |
| 7,790,699 | B2 | 9/2010 | Melvik et al. |
| 8,067,237 | B2* | 11/2011 | Mooney et al. ............. 435/375 |
| 8,188,058 | B2 | 5/2012 | Hackam et al. |
| 8,273,373 | B2* | 9/2012 | Alsberg et al. ............. 424/484 |
| 8,709,464 | B2 | 4/2014 | Ma et al. |
| 8,728,456 | B2 | 5/2014 | Sands et al. |
| 8,932,583 | B2 | 1/2015 | Mooney et al. |
| 9,012,399 | B2 | 4/2015 | Cao et al. |
| 9,132,210 | B2 | 9/2015 | Mooney et al. |
| 9,370,558 | B2 | 6/2016 | Ali et al. |
| 2002/0131853 | A1 | 9/2002 | Nagasawa |
| 2002/0150604 | A1 | 10/2002 | Yi et al. |
| 2003/0075822 | A1 | 4/2003 | Slivka et al. |
| 2003/0082806 | A1 | 5/2003 | Berenson et al. |
| 2003/0095994 | A1 | 5/2003 | Geistlich et al. |
| 2003/0100527 | A1 | 5/2003 | Krieg et al. |
| 2003/0194397 | A1 | 10/2003 | Mishra |
| 2003/0232895 | A1* | 12/2003 | Omidian et al. ............. 521/99 |
| 2004/0058883 | A1 | 3/2004 | Phillips et al. |
| 2004/0063206 | A1 | 4/2004 | Rowley et al. |
| 2004/0136968 | A1 | 7/2004 | Zheng et al. |
| 2004/0151764 | A1 | 8/2004 | Zamora |
| 2004/0220111 | A1 | 11/2004 | Kleinman et al. |
| 2004/0242469 | A1 | 12/2004 | Lee et al. |
| 2004/0242482 | A1 | 12/2004 | Gehring et al. |
| 2005/0002915 | A1 | 1/2005 | Atala et al. |
| 2005/0037330 | A1 | 2/2005 | Fischer et al. |
| 2005/0053667 | A1 | 3/2005 | Irvine et al. |
| 2005/0079159 | A1 | 4/2005 | Shastri et al. |
| 2005/0090008 | A1 | 4/2005 | Segura et al. |
| 2005/0106211 | A1 | 5/2005 | Nelson et al. |
| 2005/0154376 | A1 | 7/2005 | Riviere et al. |
| 2005/0177249 | A1 | 8/2005 | Kladakis et al. |
| 2005/0202394 | A1 | 9/2005 | Dobson |
| 2006/0083712 | A1 | 4/2006 | Anversa |
| 2006/0141018 | A1 | 6/2006 | Cochrum et al. |
| 2006/0264380 | A1 | 11/2006 | Hellstrom et al. |
| 2006/0292134 | A1 | 12/2006 | Stohs |
| 2007/0003595 | A1 | 1/2007 | Wang et al. |
| 2007/0020232 | A1 | 1/2007 | Rossignol et al. |
| 2007/0026518 | A1* | 2/2007 | Healy ............. C08J 3/246 435/325 |
| 2007/0081972 | A1 | 4/2007 | Sandler et al. |
| 2007/0116680 | A1 | 5/2007 | Stegemann et al. |
| 2007/0178159 | A1 | 8/2007 | Chen et al. |
| 2007/0190646 | A1 | 8/2007 | Engler et al. |
| 2008/0044900 | A1 | 2/2008 | Mooney et al. |
| 2008/0044990 | A1 | 2/2008 | Lee |
| 2008/0051490 | A1 | 2/2008 | Williams et al. |
| 2008/0138416 | A1 | 6/2008 | Rauh et al. |
| 2008/0152624 | A1 | 6/2008 | Paludan et al. |
| 2008/0206308 | A1 | 8/2008 | Jabbari et al. |
| 2008/0268052 | A1 | 10/2008 | Voytik-Harbin et al. |
| 2009/0017096 | A1 | 1/2009 | Lowman et al. |
| 2009/0192079 | A1 | 7/2009 | Santos et al. |
| 2009/0238853 | A1 | 9/2009 | Liu et al. |
| 2009/0297579 | A1 | 12/2009 | Semino et al. |
| 2009/0305983 | A1 | 12/2009 | Ying et al. |
| 2010/0015709 | A1 | 1/2010 | Rehfeldt et al. |
| 2010/0055186 | A1 | 3/2010 | Dadsetan et al. |
| 2010/0080816 | A1 | 4/2010 | Hadeiba et al. |
| 2010/0129422 | A1 | 5/2010 | Han et al. |
| 2010/0159008 | A1 | 6/2010 | Barron et al. |
| 2010/0189760 | A1 | 7/2010 | Schaffer et al. |
| 2010/0190741 | A1 | 7/2010 | Cohen et al. |
| 2010/0272771 | A1 | 10/2010 | Harlow et al. |
| 2011/0008443 | A1 | 1/2011 | Alsberg et al. |
| 2011/0020216 | A1* | 1/2011 | Mooney et al. ............. 424/1.11 |
| 2011/0117170 | A1 | 5/2011 | Cao et al. |
| 2011/0223255 | A1 | 9/2011 | Thiesen et al. |
| 2011/0300186 | A1 | 12/2011 | Hellstrom et al. |
| 2012/0100182 | A1 | 4/2012 | Mooney et al. |
| 2012/0121539 | A1 | 5/2012 | Sands et al. |
| 2012/0122218 | A1 | 5/2012 | Huebsch et al. |
| 2012/0134967 | A1 | 5/2012 | Mooney et al. |
| 2012/0256336 | A1 | 10/2012 | Yano et al. |
| 2012/0264599 | A1 | 10/2012 | Komatsu et al. |
| 2012/0329791 | A1 | 12/2012 | Ashwell et al. |
| 2013/0029030 | A1 | 1/2013 | Larsen |
| 2013/0177536 | A1 | 7/2013 | Mooney et al. |
| 2013/0202707 | A1 | 8/2013 | Ali et al. |
| 2013/0302396 | A1 | 11/2013 | Mooney et al. |
| 2013/0331343 | A1 | 12/2013 | Cao et al. |
| 2014/0079752 | A1 | 3/2014 | Huebsch et al. |
| 2014/0112990 | A1 | 4/2014 | Bencherif et al. |
| 2014/0178964 | A1 | 6/2014 | Mooney et al. |
| 2014/0193488 | A1 | 7/2014 | Kim et al. |
| 2014/0234423 | A1 | 8/2014 | Sands et al. |
| 2015/0024026 | A1 | 1/2015 | Mooney et al. |
| 2015/0072009 | A1 | 3/2015 | Kim et al. |
| 2015/0366956 | A1 | 12/2015 | Mooney et al. |
| 2016/0220667 | A1 | 8/2016 | Mooney et al. |
| 2016/0220668 | A1 | 8/2016 | Mooney et al. |
| 2016/0228543 | A1 | 8/2016 | Mooney et al. |

FOREIGN PATENT DOCUMENTS

| | | |
|---|---|---|
| EP | 1452191 A2 | 9/2004 |
| EP | 1561481 A2 | 8/2005 |
| JP | 2000503884 A | 4/2000 |
| JP | 2001524136 A | 11/2001 |
| JP | 2003506401 A | 2/2003 |
| JP | 2003180815 A | 7/2003 |
| JP | 2004520043 A | 7/2004 |
| JP | 2005160669 A | 6/2005 |
| JP | 2005170816 A | 6/2005 |
| JP | 2005528401 A | 9/2005 |
| JP | 2007500673 A | 1/2007 |
| JP | 2007503881 | 3/2007 |
| JP | 2007528848 A | 10/2007 |
| JP | 2008515503 A | 5/2008 |
| JP | 2008528114 A | 7/2008 |
| JP | 2009519042 | 5/2009 |
| JP | 2009521406 A | 6/2009 |
| JP | 2009540921 | 11/2009 |
| JP | 2010502824 A | 1/2010 |
| JP | 2010508976 | 3/2010 |
| JP | 2011511684 A | 4/2011 |
| WO | WO-9616086 A1 | 5/1996 |
| WO | WO-9812228 A1 | 3/1998 |
| WO | WO-9816266 A1 | 4/1998 |
| WO | WO-9951259 A2 | 10/1999 |
| WO | WO-9951259 A3 | 1/2000 |
| WO | WO-0050006 A2 | 8/2000 |
| WO | WO-0110421 A1 | 2/2001 |
| WO | WO-0135932 A2 | 5/2001 |
| WO | WO-0216557 A2 | 2/2002 |
| WO | WO-0240071 A1 | 5/2002 |
| WO | WO-02058723 A2 | 8/2002 |
| WO | WO-03020884 A2 | 3/2003 |
| WO | WO-2004006990 A2 | 1/2004 |
| WO | WO-2004029230 A2 | 4/2004 |
| WO | WO-2004030706 A2 | 4/2004 |
| WO | WO-2004031371 A2 | 4/2004 |
| WO | WO-2004089413 A1 | 10/2004 |
| WO | WO-2005013896 A2 | 2/2005 |
| WO | WO-2005013933 A1 | 2/2005 |
| WO | WO-2005026318 A2 | 3/2005 |
| WO | WO-2005037190 A2 | 4/2005 |
| WO | WO-2005037293 A1 | 4/2005 |
| WO | WO-2005046748 A1 | 5/2005 |
| WO | WO-2005072088 A2 | 8/2005 |
| WO | WO-2006040128 A1 | 4/2006 |
| WO | WO-2006078987 A2 | 7/2006 |
| WO | WO-2006113407 A2 | 10/2006 |
| WO | WO-2006119619 A1 | 11/2006 |
| WO | WO-2006136905 A2 | 12/2006 |
| WO | WO-2007030901 A1 | 3/2007 |
| WO | WO-2007063075 A1 | 6/2007 |
| WO | WO-2007064152 A1 | 6/2007 |
| WO | WO-2007070660 A2 | 6/2007 |

(56) References Cited

FOREIGN PATENT DOCUMENTS

| WO | WO-2007078196 A1 | 7/2007 |
|---|---|---|
| WO | WO-2007107739 A1 | 9/2007 |
| WO | WO-2007150020 A1 | 12/2007 |
| WO | WO-2008018707 A1 | 2/2008 |
| WO | WO-2008031525 A1 | 3/2008 |
| WO | WO-2008109852 A2 | 9/2008 |
| WO | WO-2008114149 A2 | 9/2008 |
| WO | WO-2008148761 A1 | 12/2008 |
| WO | WO-2008157394 A2 | 12/2008 |
| WO | WO-2009002401 A2 | 12/2008 |
| WO | WO-2009005769 A2 | 1/2009 |
| WO | WO-2009018500 A1 | 2/2009 |
| WO | WO-2009072767 A2 | 6/2009 |
| WO | WO-2009074341 A1 | 6/2009 |
| WO | WO-2009102465 A2 | 8/2009 |
| WO | WO-2009146456 A1 | 12/2009 |
| WO | WO-2009155583 A1 | 12/2009 |
| WO | WO-2010078209 | 7/2010 |
| WO | WO-2010120749 A2 | 10/2010 |
| WO | WO-2011014871 A1 | 2/2011 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A2 | 12/2011 |
| WO | WO-2012009611 A2 | 1/2012 |
| WO | WO-2012019049 A1 | 2/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |
| WO | WO-2013158673 A1 | 10/2013 |
| WO | WO-2015168379 A2 | 11/2015 |
| WO | WO-2016123573 A1 | 8/2016 |

OTHER PUBLICATIONS

Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agache et al."Mechanical Properties and Young's Modulus of Human Skin in Vivo." *Arch. Dermatol. Res.* 269.3(1980):221-232.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.
Aguado et al. "Improving Viability of Stem Cells During Syringe Needle Flow Through the Design of Hydrogel Cell Carriers." *Tissue Eng. Part A.* 18.7-8(2012):806-815.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.
Aldhous. "Print Me a Heart and a Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Alsberg et al. "Regulating Bone Formation via Controlled Scaffold Design." *J. Dent. Res.* 82.11(2003):903-908.
American Diabetes Association. "Standards of Medical Care in Diabetes—2013." *Diabetes Care.* 36.S1(2013):S11-S66.
Anderson et al. "Biomaterial Microarrays: Rapid, Microscale Screening of Polymer-Cell Interaction." *Biomaterials.* 26.23(2005):4892-4897.
Anderson et al. "Nanoliter-Scale Synthesis of Arrayed Biomaterials and Application to Human Embryonic Stem Cells." *Nat. Biotechnol.* 22.7(2004):863-866.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.
Annaidh et al. "Characterization of the Anistropic Mechanical Properties of Excised Human Skin." *J. Mech. Behav. Biomed. Mater.* 5.1(2012):139-148.
Arany et al. "At the Edge of Translation—Materials to Program Cells for Directed Differentiation." *Oral Dis.* 17.3(2011):241-251.
Aschner et al. "Metabolic Memory for Vascular Disease in Diabetes." *Diabetes Technol. Ther.* 14.S1(2012):S68-S74.
Atala et al. "Endoscopic Treatment of Vesicoureteral Reflux with a Chondrocyte-Alginate Suspension." *J. Urol.* 152(1994):641-643.
Aubin et al. "Directed 3D Cell Alignment and Elongation in Microengineered Hydrogels." *Biomater.* 31.27(2010):6941-6951.
Augst et al. "Alginate Hydrogels as Biomaterials." *Macromol. Biosci.* 6(2006):623-633.
Babensee et al. "Host Response to Tissue Engineered Device." *Adv. Drug Deli. Rev.* 33.1-2(1998):111-139.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Balakrishna et al. "Structural Correlates of Antibacterial and Membrane-Permeabilizing Activities in Acylpolyamines." *Antimicrob. Agents Chemother.* 50.3(2006):852-861.
Banchereau et al. "Dendritic Cells and the Control of Immunity." *Nature.* 392.6673(1998):245-252.
Bar-Cohen et al. "Electroactive Polymer Actuators and Sensors." *MRS Bullet.* 33.3(2008):173-181.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.

(56) References Cited

OTHER PUBLICATIONS

Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math. Biol.* 61.3(1999):483-505.
Bates. "Improved Muscle Regeneration by Combining VEGF With IGF1." *Regen. Med.* 5.6(2010):853-854.
Beaucage et al. "The Functionalization of Oligonucleotides Via Phosphoramidite Derivatives." *Tetrahedron.* 49.10(1993):1925-1963.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Becker et al. "Cytological Demonstration of the Clonal Nature of Spleen Colonies Derived from Transplanted Mouse Marrow Cells." *Nature.* 197(1963):452-454.
Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bergstraesser et al. "Stimulation and Inhibition of Human Mammary Epithelial Cell Duct Morphogenesis In Vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1(2013):35-42.
Bilodeau et al. "Regular Pyramid Punch Problem." *J. Appl. Mech.* 59.3(1992):519-523.
Bischoff. "Proliferation of Muscle Satellite Cells on Intact Myofibers in Culture." *Dev. Biol.* 115.1(1986):129-139.
Blanes et al. "Induction of Autoimmune Diabetes by Oral Administration of Autoantigen." *Science.* 274.5293(1996):1707-1709.
Blumenthal et al. "Polyurethane Scaffolds Seeded with Genetically Engineered Skeletal Myoblasts: A Promising Tool to Regenerate Myocardial Function." *Artificial Organs.* 34.2(2010): E46-E54.
Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Controlling Alginate Gel Degradation Utilizing Partial Oxidation and Bimodal Molecular Weight Distribution." *Biomaterials.* 26.15(2005):2455-2465.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Degradation of Partially Oxidized Alginate and its Potential Application for Tissue Engineering." *Biotechnol. Prog.* 17.5(2001):945-950.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkmann et al. "Neutrophil Extracellular Traps Kill Bacteria." *Science.* 303.5663(2004):1532-1535.
Brouwers et al. "Can the Growth Factors PTHrP, Ihh and VEGF, Together Regulate the Development of a Long Bone?" *J. Biomech.* 39.15(2006):2774-2782.
Broxmeyer et al. "Insights into the Biology of Cord Blood Stem/Progenitor Cells." *Cell Prolif.* 44.S1(2011):55-59.
Bryant et al. "Photo-Patterning of Porous Hydrogels for Tissue Engineering." *Biomater.* 28.19(2007):2978-2986.
Buckwalter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1(2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Burdick et al. "Stimulation of Neurite Outgrowth by Neurotrophins Delivered From Degradable Hydrogels." *Biomater.* 27.3(2006):452-459.
Bégué et al. "Vaccination Against Human Papillomavirus. Implementation and Efficacy Against Cervical Cancer Control." *Bull. Acad. Natl. Med.* 191.9(2007):1805-1816. (French original and English abstract).
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Cameron et al. "The Influence of Substrate Creep on Mesenchymal Stem Cell Behaviour and Phenotype." *Biomater.* 32.26(2011):5979-5993.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.

(56) References Cited

OTHER PUBLICATIONS

Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Functional Human Vascular Network Generated in Photocrosslinkable Gelatin Methacrylate Hydrogels." *Adv. Funct. Mater.* 22.10(2012):2027-2039.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Chiang et al. "Whole Tumor Antigen Vaccines." *Semin. Immunol.* 22.3(2010):132-143.
Choi et al. "In Vitro Mineralization by Preosteoblasts in Poly(DL-lactide-*co*-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Choi. "Replacement Organs, Hot Off the Press." *New Scientist.* 177.2379(2003):16.
Chou et al. "Characterization of Photocross Linked Alginate Hydrogels for Nucleus Pulposus Cell Encapsulation." *J. Biomed. Mater. Res. A.* 91A.1(2009):187-194.
Chromiak et al. "Bioreactor Perfusion System for the Long-Term Maintenance of Tissue-Engingeered Skeletal Muscle Organoids." *In Vitro Cell Dev. Biol. Anim.* 34.9(1998):694-703.
Clark et al. "Myosin II and Mechanotransduction: A Balancing Act." *Trends Cell Biol.* 17.4(2007):178-186.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Comisar et al. "Engineering RGD Nanopatterned Hydrogels to Control Preosteoblast Behavior: A Combined Computational and Experimental Approach." *Biomaterials.* 28(2007):4409-4417.
Conboy et al. "The Regulation of Notch Signaling Controls Satellite Cell Activation and Cell Fate Determination in Postnatal Myogenesis." *Dev. Cell.* 3.3(2002):397-409.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.
Conn et al. "Purification of a Glycoprotein Vascular Endothelial Cell Mitogen From a Rat Glioma-Derived Cell Line." *PNAS.* 87.4(1990):1323-1327.
Cook et al. "A Sialomucopeptide Liberated by Trypsin from the Human Erythrocyte." *Nature.* 188(1960):1011-1012.
Cooper et al. "Extended Amplification In Vitro and Replicative Senescence: Key Factors Implicated in the Success of Human Myoblast Transplantation." *Hum. Gene Ther.* 14(2003):1169-1179.
Cooper. "Metabolic Memory: Implications for Diabetic Vascular Complications." *Pediatr. Diabetes.* 10.5(2009):343-346.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and are Implicated in Satellite Cell Maintenance and Muscle Regeneration." *Dev. Biol.* 239.1(2001):79-94.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Dar et al. "Optimization of Cardiac Cell Seeding and Distribution in 3D Porous Alginate Scaffolds." *Biotechnol. Bioeng.* 80(2002):305-312.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
de Jong et al. "Regulation of Notch Signaling Genes During BMP2-Induced Differentiation of Osteoblast Precursor Cells." *Biochem. Biophys. Res. Commun.* 320(2004):100-107.
De Temmerman et al. "Particulate Vaccines: On the Quest for Optimal Delivery and Immune Response." *Drug Disc. Today.* 16.13/14(2011):569-582.
Dembo et al. "Stresses at the Cell-to-Substrate Interface During Locomotion of Fibroblasts." *Biophys. J.* 76.4(1999):2307-2316.
den Haan et al. "CD8+ by not CD8− Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dexter et al. "Conditions Controlling the Proliferation of Haemopoietic Stem Cells In Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.

(56) References Cited

OTHER PUBLICATIONS

Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Dieu et al. "Selective Recruitment of Immature and Mature Dendritic Cells by Distinct Chemokines Expressed in Different Anatomic Sites." *J. Exp. Med.* 188.2(1988):373-386.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Doan et al. "Subcellular Localization of a Sporulation Membrane Protein is Achieved Through a Network of Interactions Along and Across the Septum." *Mol. Microbiol.* 55.6(2005):1767-1781.
Donati et al. "New Hypothesis on the Role of Alternating Sequences in Calcium-Alginate Gels." *Biomacromol.* 6.2(2005):1031-1040.
Dor et al. "Making Vascular Networks in the Adult: Branching Morphogenesis Without a Roadmap." *Trends Cell Biol.* 13.3(2003):131-136.
Douay et al. "Ex vivo Production of Human Red Blood Cells from Hematopoietic Stem Cells: What is the Future in Transfusion?" *Transfus. Med. Rev.* 21.2(2007):91-100.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dranoff. "GM-CSF-Based Cancer Vaccines." *Immunol. Rev.* 188(2002):147-154.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Eming et al. "Inflammation in Wound Repair: Molecular and Cellular Mechanisms." *J. Invest. Dermatol.* 127.3(2007):514-525.

Engler et al. "Matrix Elasticity Directs Stem Cell Lingeage Specification." *Cell.* 126.4(2006):677-689.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1Pt1(2004):617-628.
Ennett et al. "Temporally Regulated Delivery of VEGF in vitro and in vivo." *J. Biomed. Mater. Res. A.* 79.1(2006):176-184.
Exposito et al. "The Fibrallar Collagen Family." *Int. J. Mol. Sci.* 11.2(2010):407-426.
Faissner et al. "Boundaries and Inhibitory Molecules in Developing Neural Tissues." *Glia.* 13.4(1995):233-254.
Falanga. "Wound Healing and its Impairment in the Diabetic Foot." *Lancet.* 366.9498(2005):1736-1743.
Falsey et al. "Peptide and Small Molecule Microarray for High Throughput Cell Adhesion and Functional Assays." *Bioconjug. Chem.* 12.3(2001):346-353.
Farrar et al. "T Helper Subset Development: Roles of Instruction, Selection, and Transcription." *J. Clin. Invest.* 109.4(2002):431-435.
Fauquemberque et al. "HLA-A* 0201-Restricted CEA-Derived Peptide CAP1 is not a Suitable Target for T-Cell-Based Immunotherapy." *J. Immunother.* 33.4(2010):402-413.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Fischer et al. "A Brilliant Monomeric Red Fluorescent Protein to Visualize Cytoskeleton Dynamics in *Dictyostelium.*" *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Fisher et al. "The Study of Protein Mechanics with the Atomic Force Microscope." *Trends Biochem. Sci.* 24.10(1999):379-384.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Fontaine et al. "Surgical Treatment of Peripheral Circulation Disorders." *Helv. Chir. Acta.* 21.56(1954):499-533. (German Original, No English Translation Available).
Fox. "Management of Worsening Multiple Sclerosis with Mitoxantrone: A Review." *Clin. Ther.* 28.4(2006):461-474.
Friedenstein et al. "Fibroblast Precursors in Normal and Irradiated Mouse Hematopoietic Organs." *Exp. Hematol.* 4.5(1976):267-274.
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.

(56) References Cited

OTHER PUBLICATIONS

GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000230.2, Dec. 17, 2012.
GenBank Accession No. NM_000514.3, Aug. 19, 2012.
GenBank Accession No. NM_000572.2, May 18, 2014.
GenBank Accession No. NM_000601.4, Nov. 25, 2012.
GenBank Accession No. NM_000614.3, Sep. 9, 2012.
GenBank Accession No. NM_000638.3, May 4, 2014.
GenBank Accession No. NM_000660.4, Dec. 9, 2012.
GenBank Accession No. NM_000758.3, May 4, 2014.
GenBank Accession No. NM_000800.3, Mar. 4, 2012.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_001845.4, May 3, 2014.
GenBank Accession No. NM_001901.2, May 18, 2014.
GenBank Accession No. NM_002421.3_May 11, 2014.
GenBank Accession No. NM_002506.2, Dec. 9, 2012.
GenBank Accession No. NM_002632.4, May 4, 2011.
GenBank Accession No. NM_002982.3, May 3, 2014.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_006068.4, Oct. 28, 2012.
GenBank Accession No. NM_015719.3, Feb. 26, 2014.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001096124.1, Dec. 16, 2012.
GenBank Accession No. NP_001836.2, May 3, 2014.
GenBank Accession No. NP_001892.1, May 18, 2014.
GenBank Accession No. NP_002010.2, Dec. 9, 2012.
GenBank Accession No. NP_002973.1, May 3, 2014.
GenBank Accession No. NP_003239.2, Feb. 18, 2014.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_006059.2, Oct. 28, 2012.
GenBank Accession No. NP_056534.2, Feb. 26, 2014.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Glasbey et al. "Image Analysis and Three-Dimensional Modelling of Pores in Soil Aggregates." *Eur. J. Soil Sci.* 42.2(1991):479-486.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Graessley. "Entangled Linear, Branched and Network Polymer Systems—Molecular Theories." *Adv. Poly. Sci.* 47(1982):67-117.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.*130.10(2004):1191-1196.
Gros et al. "A Common Somitic Origin for Embryonic Muscle Progenitors and Satellite Cells." *Nature.* 435(2005):954-958.
Guillaume et al. "Two Abundant Proteasome Subtypes that Uniquely Process Some Antigens Presented by HLA Class I Molecules." *PNAS.* 107.43(2010):18599-18604.
Gullberg et al. "Extracellular Matrix and Its Receptors During Development." *Int. J. Dev. Biol.* 39(1995):845-854.

(56) References Cited

OTHER PUBLICATIONS

Guo et al. "Droplet Microfluidics for High-Throughput Biological Assays." *Lab Chip.* 12.12(2012):2146-2155.
Gupta et al. "Magnetically Controlled Targeted Micro-Carrier Systems." *Life Sci.* 44.3(1989):175-186.
Gurkan et al. "The Mechanical Environment of Bone Marrow: A Review." *Ann. Biomed. Eng.* 36.12(2008):1978-1991.
Gussoni et al. "Dystophin Expression and in the *mdx* Mouse Restored by Stem Cell Transplantation." *Nature.* 401(1999):390-394.
Halim et al. "Biologic and Synthetic Skin Substitutes: An Overview." *Indian J. Plast. Surg.* 43(2010):523-528.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harris. "Classification, Diagnostic Criteria, and Screening for Diabetes." *Diabetes in America.* NIH Publication No. 95-1468. Chapter 2. (1995):15-36.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Heath. "Cells for Tissue Engineering." *Trends Biotechnol.* 18.1(2006):17-19.
Helm et al. "Synergy Between Interstitial Flow and VEGF Directs Capillary Morphogenesis in vitro Through a Gradient Amplification Mechanism." *PNAS.* 102.42(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts can Give Rise to Functional Satellite Cells as Identified Using the Myf5nlacZI+ Mouse." *Gene Ther.* 8(2001):778-783.
Hildner et al. "*Batf3* Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Holland et al. "Transforming Growth Factor-β1 Release from Oligo(poly(ethylene glycol) Fumarate) Hydrogels in Conditions that Model the Cartilage Wound Healing Environment." *J. Control. Release.* 94(2004):101-114.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Ishihara et al. "Roles of Bradykinin in Vascular Permeability and Angiogenesis in Solid Tumor." *Int. Immunopharmacol.* 2.4(2002):499-509.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Jain. "Molecular Regulation of Vessel Maturation." *Nat. Med.* 9.6(2003):685-693.
Jain. "The Manufacturing Techniques of Various Drug Loaded Biodegradable Poly(lactide-*co*-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Janmey et al. "From Tissue Mechanics to Transcription Factors." *Differentiation.* 86.3(2013):112-120.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primordia." *Development.* 126.22(1999):4997-5009.

(56) References Cited

OTHER PUBLICATIONS

Jiang et al. "Two-Piconewton Slip Bond Between Fibronectin and the Cytoskeleton Depends on Talin." *Nature.* 424.6946(2003):334-337.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Jokinen et al. "Integrin-Mediated Cell Adhesion to Type I Collagen Fibrils." *J. Blol. Chem.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Juntanon et al. "Electrically Controlled Release of Sulfosalicylic Acid from Crosslinked Poly(Vinyl Alcohol) Hydrogel." *Int. J. Pharm.* 356(2008):1-11.
Kang et al. "Effect of Porous Structure on the Degradation of Freeze-Dried Gelatin Hydrogels." *J. Bioact. Compat. Poly.* 14.4(1999):331-343.
Kanzler et al. "Therapeutic Targeting of Innate Immunity with Toll-Like Receptor Agaonists and Antagonists." *Nat. Med.* 13.5(2007):552-559.
Katayama et al. "Integrated Analysis of the Genome and the Transcriptome by FANTOM." *Brief Bioinform.* 5.3(2004):249-258.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Khownium et al. "Novel Endotoxin-Compounds with Terephthalaldehyde-bis-guanyllhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kim et al. "Multifunctional Capsule-in-Capsules for Immunoprotection and Trimodal Imaging." *Angew. Chem. Int. Ed.* 50.10(2011):2317-2321.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klein et al. "Cell-Cycle Control by Physiological Matrix Elasticity and In Viivo Tissue Stiffening." *Curr. Biol.* 19.18(2009):1511-1518.
Klinman. "Immunotherapeutic Uses of CpG Oligodeoxynucleotides." *Nat. Rev. Immunol.* 4.4(2004):249-258.
Kohane. "Microparticles and Nanoparticles for Drug Delivery." *Biotechnol. Bioeng.* 96.2(2007):203-209.
Kondo et al. "A Reaction-Diffusion Wave on the Skin of the Marine Angelfish *Pomacanthus.*" *Nature.* 376(2002):765-768.
Kong et al. "Controlling Degradation of Hydrogels via the Size of Crosslinked Junctions." *Adv. Mater.* 16.21(2004):1917-1921.

Kong et al. "Controlling Rigidity and Degradation of Alginate Hydrogels via Molecular Weight Distribution." *Biomacromolec.* 5.5(2004):1720-1727.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "Designing Alginate Hydrogels to Maintain Viability of Immobilized Cells." *Biomat.* 24.22(2003):4023-4029.
Kong et al. "FRET Measurements of Cell-Traction Forces and Nano-Scale Clustering of Adhesion Ligands Varied by Substrate Stiffness." *PNAS.* 102.12(2005):4300-4305.
Kong et al. "Non-Viral Gene Delivery Regulated by Stiffness of Cell Adhesion Substrates." *Nat. Mater.* 4(2005):460-465.
Kratky et al. "Direct Activation of Antigen-Presenting Cells is Required for CD8+ T-Cell Priming and Tumor Vaccination." *PNAS.* 108.42(2011):17414-17419.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kuwahara et al. "Cell Delivery Using an Injectable and Adhesive Transglutaminase-Gelatin Gel." *Tissue Eng. Part C Methods.* 16.4(2010):609-618.
Kwon et al. "Electrically Erodible Polymer Gel for Controlled Release of Drugs." *Nature.* 354(1991):291-293.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langenkamp et al. "Kinetics of Dendritic Cell Activation: Impact on Priming of TH1, TH2 and Nonpolarized T Cells." *Nat. Immunol.* 1.4(2000):311-316.
Langer et al. "Tissue Engineering." *Science.* 260(1993):920-926.
Lanzavecchia et al. "Regulation of T Cell Immunity by Dendritic Cells." *Cell.* 106.3(2001):263-266.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-λ in Response to Poly IC." *J. Exp. Med.* 207.12(2010):2703-2717.
Leach et al. "Coating of VEGF-Releasing Scaffolds with Bioactive Glass for Angiogenesis and Bone Regeneration." *Biomater.* 27.17(2006):3249-3255.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lee et al. "Hydrogel Formation via Vell Crosslinking." *Adv. Mat.* 15.21(2003):1828-1832.
Lee et al. "Hydrogels for Tissue Engineering." *Chem. Rev.* 101. 7(2001):1869-1879.
Lefaucheur et al. "The Cellular Events of Injured Muscle Regeneration Depend on the Nature of the Injury." *Neuromusc. Disorders.* 5.6(1995):501-509.
Lele et al. "Investigating Complexity of Protein-Protein Interactions in Focal Adhesions." *Biochem. Biophys. Res. Commun.* 369. 3(2008):929-934.

(56) References Cited

OTHER PUBLICATIONS

Lensch et al. "Scientific and Clinical Opportunities for Modeling Blood Disorders With Embryonic Stem Cells." *Blood.* 107.7(2006):2605-2612.
Leor et al. "Cells, Scaffolds, and Molecules for Myocardial Tissue Engineering." *Pharmacol. Therapeutics.* 105(2005):151-163.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Letsinger et al. "Phosphoramidate Analogs of Oligonucleotides." *J. Org. Chem.* 35.11(1970):3800-3803.
Levental et al. "Soft Biological Materials and their Impact on Cell Function." *Soft Matter.* 3(2007):299-306.
Li et al. "A Novel Cyclohexene Derivate, Ethyl (6$R$)-6-[$N$-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li et al. "Purified Hybrid Cells from Dendritic Cell and Tumor Cell Fusions are Superior Activators of Antitumor Immunity." *Cancer Immunol. Immunother.* 50.9(2001):456-462.
Li. "TNF-α is a Mitogen is Skeletal Muscle." *Am. J. Physiol. Cell Physiol.* 285(2003):C370-C376.
Lin et al. "Transdermal Regulation of Vascular Network Bioengineering Using a Photopolymerizable Methacrylated Gelatin Hydrogel." *Biomater.* 34.28(2013):6785-6796.
Lipton et al. "Developmental Fate of Skeletal Satellite Cells." *Science.* 205(1979):1292-1294.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007)1113-1124.
Liu et al. "Nanostructured Materials Designed for Cell Binding and Transduction." *Biomacromolecules.* 2.2(2001):362-368.
Liu et al. "On the Viscoelastic Character of Liver Tissue: Experiments and Modelling of the Linear Behaviour." *Biorheol.* 37.3(2000):191-201.
Liu. "Dendritic Cell Subsets and Lineages, and Their Functions in Innate and Adaptive Immunity." *Cell.* 106.3(2001):259-262.
Lo et al. "Cell Movement is Guided by the Rigidity of the Substrate." *Biophys. J.* 79.1(2000):144-152.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Lumelsky et al. "Differentiation of Embryonic Stem Cells to Insulin-Secreting Structures Similar to Pancreatic Islets." *Science.* 292.5520(2001):1389-1394.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.

Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Majeti et al. "Identification of a Hierarchy of Multipotent Hematopoietic Progenitors in Human Cord Blood." *Cell Stem Cell.* 1.6(2007):635-645.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manayski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Martinsen et al. "Alginate as Immobilization Material." *Biotech. Bioeng.* 33.1(1989):79-89.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Masedunskas et al. "Role for the Actomyosin Complex in Regulated Exocytosis Revealed by Intravital Microscopy." *PNAS.* 108.33(2011):13552-13557.
Massia et al. "An RGD Spacing of 440 nm is Sufficient for Integrin αvβ3-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinney-Freeman et al. "Muscle-Derived Hematopoietic Stem Cells are Hematopoietic in Origin." *PNAS.* 99.3(2002):1341-1346.
McKinnon et al. "Biophysically Defined and Cytocompatible Covalently Adaptable Networks as Viscoelastic 3D Cell Culture Systems." *Adv. Mater.* 26.6(2014):865-872.
McPherron et al. "Regulation of Skeletal Muscle Mass in Mice by a New TGF-β Superfamily Member." *Nature.* 387(1997):83-90.
McWhorter et al. "Modulation of Macrophage Phenotype by Cell Shape." *PNAS.* 110.43(2013):17253-17258.
Meier et al. "Peptide Nucleic Acids (PNAs)—Unusual Properties of Noionic Oligonucleotide Analogues." *Angew. Chem. Int. Ed.* 31.8(1992):1008-1010.
Melero-Martin et al. "Engineering Robust and Functional Vascular Networks In Vivo With Human Adult and Cord Blood-Derived Progenitor Cells." *Circ. Res.* 103.2(2008):194-202.
Melief et al. "Immunotherapy of Established (Pre)Malignant Disease by Synthetic Long Peptide Vaccines." *Nat. Rev. Cancer.* 8(2008):351-360.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.

(56) References Cited

OTHER PUBLICATIONS

Miljkovic et al. "Chondrogenesis, Bone Morphogenetic Protein-4 and Mesenchymal Stem Cells." *Osteoarthritis Cartilage.* 16(2008):1121-1130.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermines." *J. Med. Chem.* 48(2005):2589-2599.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Miyata et al. "Biomolecule-Sensitive Hydrogels." *Adv. Drug Deliv. Rev.* 54.1(2002):79-98.
Mohan et al. "Novel Porous, Polysaccharide Scaffolds for Tissue Engineering Applications." *Trends Biomater. Artif. Organs.* 18.2(2005):219-224.
Moioli et al. "Matrices and Scaffolds for Drug Delivery in Dental, Oral and Craniofacial Tissue Engineering." *Adv. Drug Deliv. Rev.* 59.4-5(2007):308-324.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Muralidharan-Chari et al. "ARF6-Regulated Shedding of Tumor Cell-Derived Plasma Membrane Microvesicles." *Curr. Biol.* 19.22(2009):1875-1885.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_001561.5, Mar. 16, 2014.
NCBI Accession No. NM_003265, Dec. 30, 2012.
NCBI Accession No. NM_004119, Apr. 14, 2013.
NCBI Accession No. NM_004448.3, Apr. 23, 2014.
NCBI Accession No. NM_005018.2, Apr. 27, 2014.
NCBI Accession No. NM_006274.2, Mar. 31, 2013.
NCBI Accession No. NM_017442, Apr. 14, 2012.
NCBI Accession No. NM_181780.3, Jan. 27, 2014.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_003367, Jan. 30, 2011.
NCBI Accession No. NP_005009.2, Apr. 27, 2014.
NCBI Accession No. NP_059138, Apr. 14, 2012.
NCBI Accession No. NP_861445.3, Jan. 27, 2014.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Niamlang et al. "Electrically Controlled Release of Salicylic Acid from poly(p-phenylene vinylene) Polyacrylamide Hydrogels." *Int. J. Pharm.* 371(2009):126-133.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The α6β4 Integrin is a Receptor for Both Lamin and Kalinin." *Exp. Cell Res.* 211.2(1994):360-367.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohashi et al. "Surgical Excision Combined with Autologous Whole Tumor Cell Vaccination is an Effective Therapy for Murine Neuroblastoma." *J. Ped. Surg.* 41(2006):1361-1368.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Orner et al. "Arrays for the Combinatorial Exploration of Cell Adhesion." *J. Am. Chem. Soc.* 126.35(2004):10808-10809.
Osunkoya et al. "Synthesis and Fate of Immunological Surface Receptors on Cultured Burkitt Lymphoma Cells." *Int. J. Cancer.* 4.2(1969):159-165.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.

(56) References Cited

OTHER PUBLICATIONS

Parekkadan et al. "Mesenchymal Stem Cell-Derived Molecules Reverse Fulminant Hepatic Failure." *PLoS One*. 2.9(2007):e941.
Park et al. "Photopolymerized Hyaluronic Acid-Based Hydrogels and Interpenetrating Networks." *Biomater*. 24.6(2003):893-900.
Parker et al. "Effect of Mitoxantrone on Outcome of Children with First Relapse of Acute Lymphoblastic Leukemia (ALL R3): An Open-Label Radomised Trial." *Lancet*. 376(2010):2009-2017.
Partridge et al. "Conversion of mdx Myofibres From Dystrophin-Negative to -Positive by Injection of Normal Myoblasts." *Nature*. 337.6203(1989):176-179.
Pawlaczyk et al. "Age-Dependent Biomechanical Properties of the Skin." *Postepy. Dermatol. Alergol*. 30.5(2013):302-306.
Pedersen et al. "Induction of Regulatory Dendritic Cells by Desamethasone and 1α,25-Dihydroxyvitamin D3." *Immunol. Lett*. 91(2004):63-69.
Pek et al. "The Effect of Matrix Stiffness on Mesenchymal Stem Cell Differentiation in a 3D Thixotropic Gel." *Biomater*. 31.3(2010):385-391.
Pelinkovic et al. "Tissue Engineering and Gene Therapy of the Muscoskeletal System with Muscle Cells." *Z. Orthop. Ihre Grenzgeb*. 138.5(2000):402-406. (German Original and English Abstract).
Pena et al. "Effects of TGF-β and TGF-β Neutralizing Antibodies on Fibroblast-Induced Collagen Gel Contraction: Implications for Proliferative Vitroretinpathy." *Invest. Ophthalmol. Vis. Sci*. 35.6(1994):2804-2808.
Peters et al. "Engineering Vascular Networks in Porous Polymer Matrices." *J. Biomed. Mater. Res*. 60.4(2002):668-678.
Peyton et al. "The Use of Poly(ethylene glycol) Hydrogels to Investigate the Impact of ECM Chemistry and Mechanics on Smooth Muscle Cells." *Biomater*. 27.28(2006):4881-4893.
Phillippi. "Patterning of Multiple Cell Lineages from a Single Stem Cell Population." *Annual Meeting of the American Society for Cell Biology*. (Dec. 10, 2006).
Pinho et al. "PDGFRα and CD51 Mark Human Nestin+ Sphere-Forming Mesenchymal Stem Cells Capable of Hematopoietic Progenitor Cell Expansion." *J. Exp. Med*. 210.7(2013):1351-1367.
Pluen et al. "Role of Tumor-Host Interactions in Interstitial Diffusion of Macromolecules: Cranial vs. Subcutaneous Tumors." *PNAS*. 98.8(2001):4628-4633.
Pooyan et al. "Conjugates Bearing Multiple Formyl-Methionyl Peptides Display Enhanced Binding to, but not Activation of Phagocytic Cells." *Bioconjugate Chem*. 13.2(2002):216-223.
Pope et al. "Organ-Specific Regulation of the CD8 T Cell Response to *Listeria monocytogenes* Infection." *J. Immunol*. 166(2001):3402-3409.
Porter et al. "Separation of Natural Populations of Coliform Bacteria from Freshwater and Sewage by Magnetic-Bead Cell Sorting." *J. Microbiol. Meth*. 33.3(1998):221-226.
Pouzet et al. "Factors Affecting Functional Outcome After Autologous Skeletal Myoblast Transplantation." *Ann. Thorac. Surg*. 71(2001):844-851.
Pulendran et al. "Flt3-Ligand and Granulocyte Colony-Stimulating Factor Mobilize Distinct Human Dendritic Cell Subsets In Vivo." *J. Immunol*. 165(2000):566-572.
Qi et al. "Patterned Differentiation of Individual Embryoid Bodies in Spatially Organized 3D Hybrid Microgels." *Adv. Mater*. 22.46(2010):5276-5281.
Qin et al. "Soft Lithography for Micro- and Nanoscale Patterning." *Nat. Protoc*. 5.3(2010):491-502.
Qu et al. "Development of Approaches to Improve Cell Survival in Myoblast Transfer Therapy." *J. Cell Biol*. 142.5(1998):1257-1267.
Qu-Petersen et al. "Identification of a Novel Population of Muscle Stem Cells in Mice: Potential for Muscle Regeneration." *J. Cell Biol*. 157.5(2002):851-864.
Quezada et al. "CTLA4 Blockade and GM-CSF Combination Immunotherapy Alters the Intratumor Balance of Effector and Regulatory T Cells." *J. Clin. Invest*. 116.7(2006):1935-1945.
Qui et al. "Environment-Sensitive Hydrogels for Drug Delivery." *Adv. Drug Deliv. Rev*. 53.3(2001):321-339.
Raeber et al. "Molecularly Engineered PEG Hydrogels: A Novel Model System for Proteolyrically Mediated Cell Migration." *Biophys. J*. 89.2(2005):1374-1388.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation*. 108.16(2003):1933-1938.
Ramón-Azcón et al. "Gelatin Methacrylate as a Promising Hydrogel for 3D Microscale Organization and Proliferation of Dielectroretically Patterned Cells." *Lab on a Chip*. 12.16(2012):2959-2969.
Randolph et al. "Migration of Dendritic Cell Subsets and Their Precursors." *Annu. Rev. Immunol*. 26(2008):293-316.
Ranganath et al. "Harnessing the Mesenchymal Stem Cell Secretome for the Treatment of Cardiovascular Disease." *Cell Stem Cell*. 10.3(2012):244-258.
Raposo et al. "Extracellular Vesicles: Exosomes, Microvesicles, and Friends." *J. Cell. Biol*. 200.4(2013):373-383.
Rappolee et al. "Macrophage-Derived Growth Factors." *Curr. Top. Microbiol. Immunol*. 181(1992):87-140.
Rapraeger. "Syndecan-Regulated Receptor Signaling." *J. Cell. Biol*. 149.5(2000):995-998.
Reddy et al. "Exploiting Lymphatic Transport and Complement Activation in Nanoparticle Vaccines." *Nat. Biotechnol*. 25.10(2007):1159-1164.
Reimann et al. "Satellite Cells in Normal and Regenerated Soleus Muscles of mdx and Control Mice." *Eur. J. Neurosci*.10(1998):366. (Abstract #153.07).
Reis e Sousa. "Activation of Dendritic Cells: Translating Innate into Adaptive Immunity." *Curr. Opin. Immunol*. 16.1(3005):21-25.
Rhoads et al. "Satellite Cell-Mediated Angiogenesis in vitro Coincides with a Functional Hypoxia-Inducible Factor Pathway." *Am. J. Physiol. Cell Physiol*. 296.6(2009):C1321-C1328.
Richards Grayson et al. "Multi-Pulse Drug Delivery From a Resorbable Polymeric Microchip Device." *Nat. Mater*. 2.11(2003):767-772.
Richardson et al. "Polymeric System for Dual Growth Factor Delivery." *Nat. Biotech*. 19.11(2001):1029-1034.
Riddle et al. "Role of Poly(lactide-co-glycolide) Particle Size on Gas-Foamed Scaffolds." *J. Biomater. Sci. Polym. Ed*. 15.12(2004):1561-1570.
Ridgway et al. "Inhibition of DII4 Signalling Inhibits Tumour Growth by Deregulating Angiogenesis." *Nature*. 444.7122(2006):1083-1087.
Rinderknecht et al. "The Amino Acid Sequence of Human Insulin-Like Growth Factor I and its Structural Homology with Proinsulin." *J. Biol. Chem*. 253.8(1978):2769-2776.
Rizzo et al. "An Improved Cyan Fluorescent Protein Variant Useful for FRET." *Nat. Biotechnol*. 22.4(2004):445-449.
Roccaro et al. "BM Mesenchymal Stromal Cell-Derived Exosomes Facilitate Multiple Myeloma Progression." *J. Clin. Invest*. 123.4(2013):1542-1555.
Rodriguez et al. "Minimal "Self" Peptides that Inhibit Phagocytic Clearance and Enhance Delivery of Nanoparticles." *Science*. 339.6122(2013):971-975.
Rosenberg et al. "Cancer Immunotherapy: Moving Beyond Current Vaccines." *Nat. Med*. 10.9(2004):909-915.
Roth et al. "SC68896, A Novel Small Molecule Proteasome Inhibitor, Exerts Antiglioma Activity In vitro and In vivo." *Clin. Cancer Res*. 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol*. 295(2008):1037-1044.
Rowley et al. "Alginate Type and RGD Density Control Myoblast Phenotype." *J. Biomed. Mater. Res*. 60.2(2002):217-233.
Rowley et al. "Biomaterials to Spatially Regulate Cell Fate." *Adv. Mater*. 14.12(2002):886-889.
Rowley. "Alginate Hydrogels as Synthetic Extracellular Matrix Materials." *Biomaterials*. 20.1(1999):45-53.

(56) References Cited

OTHER PUBLICATIONS

Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Salem et al. "Defining the Antigen-Specific T-Cell Response to Vaccination and Poly(I:C)/TLR3 Signaling." *J. Immunother.* 28.3(2005):220-228.
Salvador et al. "Combination of Immune Stimulating Adjuvants With Poly(lactide-co-glycolide) Microspheres Enhances the Immune Response of Vaccines." *Vaccine.* 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Scheel et al. "Toll-Like Receptor-Dependent Activation of Several Human Blood Cell Types by Protamine Condensed mRNA." *Eur. J. Immunol.* 35(2005):1557-1566.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schofield. "The Relationship Between the Spleen Colony-Forming Cell and the Haemopoietic Stem Cell." *Blood. Cells.* 4.1-2(1978):7-25.
Schuler et al. "The Use of Dendritic Cells in Cancer Immunotherapy." *Curr. Opin. Immunol.* 15.2(2003):138-147.
Schwartz. "Integrins and Extracellular Matrix in Mechanotransduction." *Cold Spring Harb. Perspect. Biol.* 2.12(2010):a005066.
Seale et al. "Pax7 Is Required for the Specification of Myogenic Satellite Cells." *Cell.* 102.6(2000):777-786.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.

Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Shoichet et al. "Stability of Hydrogels Used in Cell Encapsulation: An In Vitro Comparison of Alginate and Agarose." *Biotechnol. Bioeng.* 50(1996):374-381.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Siegwart et al. "Synthesis, Characterization, and in vitro Cell Culture Viability of Degradable Poly(*N*-isopropylacrylamide-*co*-5,6-benzo-2-methylene-1,3-dioxepane)-Based Polymers and Cross-linked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Silva et al. "Material-Based Deployment Enhances Efficacy of Endothelial Progenitor Cells." *PNAS.* 105.38(2008):14347-14352.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Singer et al. "Cutaneous Wound Healing." *N. Engl. J. Med.* 341.10(1999):738-746.
Skokos et al. "CD8-DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.

(56) References Cited

OTHER PUBLICATIONS

Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Sun et al. "Sustained Vascular Endothelial Growth Factor Delivery Enhances Angiogenesis and Perfusion in Ischemic Hind Limb." *Pharm. Res.* 22.7(2005):1110-1116.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Takahashi et al. "Induction of Pluripotent Stem Cells from Adult Human Fibroblasts by Defined Factors." *Cell.* 131.5(2007):861-872.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tanaka et al. "Collapse of Gels in an Electric Field." *Science.* 218(1982):467-469.
Tannous. "*Gaussia* Luciferase Reporter Assay for Monitoring Biological Processes in Culture and in vivo." *Nat. Protoc.* 4.4(2009):582-591.
Tatsumi et al. "HGF/SF is Present in Normal Adult Skeletal Muscle and is Capable of Activating Satellite Cells." *Dev. Biol.* 194.1(1998):114-128.
ten Dijke et al. "Growth Factors for Wound Healing." *Nat. Biotechnol.* 7(1989):793-798.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Thurston et al. "The Delta Paradox: DLL4 Blockade Leads to More Tumour Vessels but Less Tumour Growth." *Nat. Rev. Cancer.* 7.5(2007):327-331.
Tidball. "Inflammatory Cell Response to Acute Muscle Injury." *Med. Sci. Sports Exerc.* 27.7(1995):1022-1032.
Tomer et al. "Electrically Controlled Release of Macromolecules from Cross-Linked Hyaluronic Acid Hydrogels." *J. Control. Release.* 33.3(1995):405-413.
Tong et al. "Engineering Interpenetrating Network Hydrogels as Biomimetic Cell Niche with Independently Tunable Biochemical and Mechanical Properties." *Biomater.* 35.6(2014):1807-1815.
Tourniaire et al. "Polymer Microarrays for Cellular Adhesion." *Chem. Commun.* 20(2006):2118-2120.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Tsien. "The Green Fluorescent Protein." *Annu. Rev. Biochem.* 67(1998):509-544.
Turing. "Discussion: Turing's Theory of Morphogenesis—Its Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.
Uchida et al. "Immunization by Particle Bombardment of Antigen-Loaded poly-(DL-lactide-co-glycolide) Microspheres in Mice." *Vaccine.* 12(2006):2120-2130.
Ugarte et al. "Notch Signaling Enhances Osteogenic Differentiation While Inhibiting Adipogenesis in Primary Human Bone Marrow Stromal Cells." *Exp. Hematol.* 37(2009):867-875.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al. "Stem Cell Niches in the Adult Mouse Heart." *PNAS.* 103.24(2006):9226-9231.
van der Bruggen et al. "T Cell-Defined Tumor Antigens." *Cancer Immunity.* (2013). Http:www.cancerimmunity.org/peptide.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Venturoni et al. "Investigations into the Polymorphism of Rat Tail Tendon Fibrils Using Atomic Force Microscopy." *Biochem. Biophys. Res. Commun.* 303.2(2003):508-513.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.

(56) References Cited

OTHER PUBLICATIONS

Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wang et al. "Evolution of New Nonantibody Proteins via Iterative Somatic Hypermutation." *PNAS.* 101.48(2004):16745-16749.
Wang et al. "Mechanotransduction at a Distance: Mechanically Coupling the Extracellular Matric with the Nucleus." *Nat. Rev. Mol. Cell. Biol.* 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs.* 31.3(2013):707-713.
Warner et al. "Cyclooxygenases: New Forms, New Inhibitors, and Lessons from the Clinic." *FASEB J.* 18.7(2004):790-804.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res.* 30(1963):331-338.
Wen et al. "Mechanically Robust Gelatin-Alginate IPN Hydrogels by a Combination of Enzymatic and Ionic Crosslinking Approaches." *Macromol. Mater. Eng.* 299(2013):504-513.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):148-152.
Wong et al. "Mechanical Force Prolongs Acute Inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wozniak et al. "Mechanotransduction in Development: A Growing Role for Contractility." *Nat. Rev. Mol. Cell Biol.* 10.1(2009):34-43.
Wright et al. "Muscle-Based Gene Therapy and Tissue Engineering for the Musculoskeletal System." *Drug Disc. Today.* 6.14(2001):728-733.
Xie et al. "Preparation and Application of Surface-Coated Superparamagnetic Nanobeads in the Isolation of Genomic DNA." *J. Magn. Magnetic Mater.* 277.1(2004):16-23.
Yancopoulos et al. "Vascular-Specific Growth Factors and Blood Vessel Formation." *Nature.* 407.6801(2000):242-248.
Yeung et al. "Effects of Substrate Stiffness on Cell Morphology, Cytoskeletal Structure, and Adhesion." *Cell Motil. Cytoskeleton.* 60.1(2005):24-34.
Yoo et al. "Bio-Inspired, Bioengineered and Biomimetic Drug Delivery Carriers." *Nat. Rev. Drug Discov.* 10.7(2011):521-535.
Yoon. "Hidden Markov Models and their Applications in Biological Sequene Analysis." *Curr. Genomics.* 10.6(2009):402-415.
Young et al. "Gelatin as a Delivery Vehicle for the Controlled Release of Bioactive Molecules." *J. Control. Release.* 109.1-3(2005):256-274.
Yu et al. "Induced Pluripotent Stem Cell Lines Derived from Human Somatic Cells." *Science.* 318.5858(2007):1917-1920.
Yuen et al. "Mimicking Nature by Codelivery of Stimulant and Inhibitor to Create Temporally Stable and Spatially Restricted Angiogenic Zones." *PNAS.* 107.42(2010):17933-17938.
Yuk et al. "Electric Current-Sensitive Drug Delivery System Using Sodium Alginate/Polyacrylic Acid Composites." *Pharm. Res.* 9.7(1992):955-957.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zemel et al. "Optimal Matrix Rigidity for Stress Fibre Polarization in Stem Cells." *Nat. Phys.* 6.6(2010):468-473.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
Zhang et al. "A Tension-Induced Mechanostransduction Pathway Promotes Epithelial Morphogenesis." *Nature.* 471.7336(2011):99-103.
Zhang et al. "Talin Depletion Reveals Independence of Initial Cell Spreading from Integrin Activation and Traction." *Nat. Cell Biol.* 10.9(2008):1062-1068.
Zhao et al. "Active Scaffolds for On-Demand Drug and Cell Delivery." *PNAS.* 108.1(201 1):67-72.
Zhao et al. "Directed Cell Migration via Chemoattractants Released from Degradable Microspheres." *Biomat.* 26(2005):5048-5063.
Zhao et al. "Stress-Relaxation Behavior in Gels with Ionic and Covalent Crosslinks." *J. Appl. Phys.* 107.6(2010):63509.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
Yang, Fan et al., "The effect of incorporating RGD adhesive peptide in polyethylene glycol diacrylate hydrogel on osteogenesis of bone marrow stromal cells," *Biomaterials*, vol. 26(2005):5991-5998.
Annual Review Meneki. Immunity. 2008:122-31.
Brunner et al. Enhanced dendritic cell maturation by TNF-alpha or cytidine-phosphateguanosine DNA drives T cell activation in vitro and therapeutic anti-tumor immune responses in vivo. J Immunol. Dec. 1, 2000;165(11):6278-86.
Corcione et al. CCL19 and CXCL12 trigger in vitro chemotaxis of human mantle cell lymphoma B cells. Clin Cancer Res. Feb. 1, 2004;10(3):964-71.
Fransen et al. Local immunomodulation for cancer therapy: Providing treatment where needed. Oncoimmunology. Nov. 1, 2013;2(11):e26493.
Latorre et al. Applications of magnetic nanoparticles in medicine: magnetic fluid hyperthermia. P R Health Sci J. Sep. 2009;28(3):227-38.
Liu et al. Immunostimulatory CpG oligodeoxynucleotides enhance the immune response to vaccine strategies involving granulocyte-macrophage colony-stimulating factor. Blood. Nov. 15, 1998;92(10):3730-6.
Malhotra et al. Use of an oncolytic virus secreting GM-CSF as combined oncolytic and immunotherapy for treatment of colorectal and hepatic adenocarcinomas. Surgery. Apr. 2007;141(4):520-9.
Nestle et al. Vaccination of melanoma patients with peptide- or tumor lysate-pulsed dendritic cells. Nat Med. Mar. 1998;4(3):328-32.
Sato. Human dendritic cells. Biotherapy. Nov. 2004;18(6):467-77.
Wang et al. Photothermal effects of supramolecularly assembled gold nanoparticles for the targeted treatment of cancer cells. Angew Chem Int Ed Engl. May 17, 2010;49(22):3777-81.

(56) References Cited

OTHER PUBLICATIONS

Yamazaki et al., CD8+ CD205+ splenic dendritic cells are specialized to induce Foxp3+ regulatory T cells. J Immunol. Nov. 15, 2008;181(10):6923-33.

Lee et al., Controlling Mechanical and Swelling Properties of Alginate Hydrogels Independently by Cross-Linker Type and Cross-Linking Density. Macromolecules. 2000;33(11):4291-4.

Pajonk et al., From sol-gel to aerogels and cryogels. Journal of Non-Crystalline Solids. 1990;121(1-3):66-67.

Research Results of National Institute of Advanced Industrial Science and Technology, 2006, URL: [http://www.aist.go.jp/aist_j/press_release/pr2006/pr20060719. html].

Thornton et al., Shape retaining injectable hydrogels for minimally invasive bulking. J Urol. Aug. 2004;172(2):763-8.

\* cited by examiner

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Gly Gly Gly Gly Arg Gly Asp Ala Ser Ser Lys Tyr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: acryloyl-PEG
<222> LOCATION: (1)..(1)

<400> SEQUENCE: 2

Gly Gly Gly Gly Arg Gly Asp Ala Ser Ser Lys Tyr
1               5                   10

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
tccatgacgt tcctgacgtt                                                  20

<210> SEQ ID NO 4
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 4
tccatgagct tcctgagctt                                                    20

<210> SEQ ID NO 5
<211> LENGTH: 128
<212> TYPE: PRT
<213> ORGANISM: Homo sapiens

<400> SEQUENCE: 5

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
            20                  25                  30

Thr Ala Ala Glu Met Asn Glu Thr Val Glu Val Ile Ser Glu Met Phe
        35                  40                  45

Asp Leu Gln Glu Pro Thr Cys Leu Gln Thr Arg Leu Glu Leu Tyr Lys
    50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
            100                 105                 110

Asp Phe Leu Leu Val Ile Pro Phe Asp Cys Trp Glu Pro Val Gln Glu
            115                 120                 125
```

INJECTABLE CRYOGEL VACCINE DEVICES AND METHODS OF USE THEREOF

RELATED APPLICATIONS

This application is a continuation-in-part of U.S. application Ser. No. 14/112,096, which is a national stage application, filed under 35 U.S.C. §371, of International Application No. PCT/US2012/035505 filed Apr. 27, 2012, which claims the benefit of priority under 35 U.S.C. §119(e) to U.S. Provisional Application No. 61/480,237 filed Apr. 28, 2011. This application also claims the benefit of priority under 35 U.S.C. §119(e) to U.S. Provisional Application No. 61/757,509 filed Jan. 28, 2013 and U.S. Provisional Application No. 61/915,985 filed Dec. 13, 2013. The contents of each of these applications are incorporated herein by reference in their entireties.

INCORPORATION-BY-REFERENCE OF SEQUENCE LISTING

The contents of the text file named "29297-084002US_ST25.txt", which was created on Apr. 24, 2014 and is 3 KB in size, is hereby incorporated by reference in their entirety.

STATEMENT AS TO FEDERALLY SPONSORED RESEARCH

This invention was made with U.S. Government support under Grant Numbers R01 DE013349, 5R01 DE019917-03, and R01 EB015498 from the National Institutes of Health and Award Number ECS-0335765 from the National Science Foundation. The Government has certain rights in the invention.

FIELD OF THE INVENTION

The invention relates to polymer-containing devices for drug and cell delivery systems.

BACKGROUND

Cancer is a devastating disease with a high mortality rate that can affect nearly any organ in the body. Although treatment options exist for certain cancers, these options are limited in terms of efficacy, safety, and applicability to a wide range of cancer types. Thus, there is a need for more effective, safe, and widely-applicable cancer treatments. There is also a need for methods of preventing cancer.

Three-dimensional polymer-containing devices, such as scaffold matrices, have been used for a number of applications, including tissue regeneration/repair and cell transplantation. For example, porous and biodegradable polymer scaffolds have been utilized as a structural supporting matrix or as a cell adhesive substrate for cell-based tissue engineering. However, a major side effect of the surgical implantation of three dimensional scaffolds is the trauma created by physicians while treating patient illness. In particular, current technologies for the surgical implantation of three dimensional scaffolds involve incisions that lead to patient pain, bleeding, and bruising. As such, there is a pressing need in the art to develop less invasive structured polymer-containing devices.

This invention addresses these needs.

SUMMARY OF THE INVENTION

The invention features injectable hydrogel/cryogel-based vaccines greatly increase the efficacy of vaccine therapy for many cancer types, including melanoma and breast cancer. These vaccines provide much needed hope for patients with these fatal diseases.

The invention provides a cryogel sponge-like vaccine that has several advantages as a prophylactic cancer vaccine (e.g., for melanoma or breast cancer). First, the vaccine does not require expensive, time-consuming preparation and expansion of cells in some versions. Second, it is safely and easily administered with subcutaneous injection. Third, the diversity of native cancer antigens available from the use of whole cancer cells, conservation of cancer-specific cell surface antigens, and the ability to recruit, house, and activate immune cells, demonstrates the potential for using cryogel-based vaccines to develop safer and more effective cellular cancer vaccines with long-term protective benefits.

The present invention also provides compositions and a minimally-invasive method of injecting preformed large macroporous polymer-based hydrogels (e.g., cryogels) that are loaded with cargo such as cells and/or therapeutics such as small molecule compounds, proteins/peptides (e.g., antigens to which an immune response is desired), or nucleic acids. Hydrogel (also called aquagel) is a network of polymer chains that are hydrophilic, and are sometimes found as a colloidal gel in which water is the dispersion medium. Hydrogels are highly absorbent (they can contain over 99% water) natural or synthetic polymers that possess a degree of flexibility very similar to natural tissue, due to their significant water content. Unlike conventional hydrogels, a unique characteristic of the devices described herein is that when an appropriate shear stress is applied, the deformable hydrogel is dramatically and reversibly compressed (up to 95% of its volume), resulting in injectable macroporous preformed scaffolds. This property allows the devices to be delivered via syringe with high precision to target sites.

Accordingly, the invention features a cell-compatible and optionally, cell-adhesive, highly crosslinked hydrogel (e.g., cryogel) polymer composition comprising open interconnected pores, wherein the hydrogel (e.g., cryogel) is characterized by shape memory following deformation by compression or dehydration. The device has a high density of open interconnected pores. Also, the hydrogel (e.g., cryogel) comprises a crosslinked gelatin polymer or a crosslinked alginate polymer.

Examples of polymer compositions from which the cryogel is fabricated include alginate, hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), or Poly(acrylic acid) (PAAc). For example, the composition comprises an alginate-based hydrogel/cryogel. In another example, the composition comprises a gelatin-based hydrogel/cryogel.

In some embodiments, the invention also features gelatin scaffolds, e.g., gelatin hydrogels such as gelatin cryogels, which are a cell-responsive platform for biomaterial-based therapy. Gelatin is a mixture of polypeptides that is derived from collagen by partial hydrolysis. These gelatin scaffolds have distinct advantages over other types of scaffolds and hydrogels/cryogels. For example, the gelatin scaffolds of the invention support attachment, proliferation, and survival of cells and are degraded by cells, e.g., by the action of enzymes such as matrix metalloproteinases (MMPs) (e.g., recombinant matrix metalloproteinase-2 and -9).

Prefabricated gelatin cryogels rapidly reassume their original shape ("shape memory") when injected subcutaneously into a subject (e.g., a mammal such as a human, dog, cat, pig, or horse) and elicit little or no harmful host immune response (e g, immune rejection) following injection. In some examples, gelatin hydrogels are loaded with granulocyte-macrophage colony-stimulating factor (GM-CSF). Controlled release of GM-CSF from gelatin cryogels results in significant infiltration of the scaffold by immune cells and promotes matrix metalloproteinase production, leading to cell-mediated degradation of the cryogel matrix.

In some embodiments, the hydrogel (e.g., cryogel) comprises polymers that are modified, e.g., sites on the polymer molecule are modified with a methacrylic acid group (methacrylate (MA)) or an acrylic acid group (acrylate). Exemplary modified hydrogels/cryogels are MA-alginate (methacrylated alginate) or MA-gelatin. In the case of MA-alginate or MA-gelatin, 50% corresponds to the degree of methacrylation of alginate or gelatin. This means that every other repeat unit contains a methacrylated group. The degree of methacrylation can be varied from 1% to 90%. Above 90%, the chemical modification may reduce solubility of the polymer water-solubility.

Polymers can also be modified with acrylated groups instead of methacrylated groups. The product would then be referred to as an acrylated-polymer. The degree of methacrylation (or acrylation) can be varied for most polymers. However, some polymers (e.g. PEG) maintain their water-solubility properties even at 100% chemical modification. After crosslinking, polymers normally reach near complete methacrylate group conversion indicating approximately 100% of cross-linking efficiency. For example, the polymers in the hydrogel are 50-100% crosslinked (covalent bonds). The extent of crosslinking correlates with the durability of the hydrogel. Thus, a high level of crosslinking (90-100%) of the modified polymers is desirable.

For example, the highly crosslinked hydrogel/cryogel polymer composition is characterized by at least 50% polymer crosslinking (e.g., 75%, 80%, 85%, 90%, 95%, 98%). The high level of crosslinking confers mechanical robustness to the structure. However, the % crosslinking is generally less than 100%. The composition is formed using a free radical polymerization process and a cryogelation process. For example, the cryogel is formed by cryopolymerization of methacrylated gelatin or methacrylated alginate. In some cases, the cryogel comprises a methacrylated gelatin macromonomer or a methacrylated alginate macromonomer concentration of 1.5% (w/v) or less (e.g., 1.5%, 1.4%, 1.3%, 1.2%, 1.1%, 1% 0.9%, 0.8%, 0.7%, 0.6%, 0.5%, 0.4%, 0.3%, 0.2% or less). For example, the methacrylated gelatin or alginate macromonomer concentration is about 1% (w/v).

In some embodiments, crosslinked gelatin hydrogels/cryogels are formed by modification of gelatin with pendant methacrylate groups. For example, crosslinking occurs via radical polymerization. In some examples, 2-6% (e.g., 3-4%) of the amino acid composition of gelatin is lysine. In some cases, lysine in the gelatin is converted to reactive methacrylate groups. In some cases, 70-90% (e.g., 80%) of the lysine in the gelatin is converted to reactive methacrylate groups. These reactive methacrylate groups on the gelatin are then crosslinked, e.g., by radical polymerization. In some embodiments, the gelatin polymers of the invention (e.g., crosslinked by radical polymerization) contain a greater number of crosslinks compared to a gelatin polymer incubated at room temperature without radical polymerization (e.g., without modification by methacrylate).

The cryogel comprises at least 75% pores, e.g., 80%, 85%, 90%, 91%, 92%, 93%, 94%, 95%, 96%, 97%, 98%, or 99% or more pores. The pores are interconnected. Interconnectivity is important to the function of the composition, as without interconnectivity, water would become trapped within the gel. Interconnectivity of the pores permits passage of water (and other compositions such as cells and compounds) in and out of the structure. In a fully hydrated state, the composition comprises at least 90% water (e.g., between 90-99%, at least 92%, 95%, 97%, 99%, or more) water. For example, at least 90% (e.g., at least 92%, 95%, 97%, 99%, or more) of the volume of the cryogel is made of liquid (e.g., water) contained in the pores. In a compressed or dehydrated hydrogel, up to 50%, 60%, 70% of that water is absent, e.g., the cryogel comprises less than 25% (20%, 15%, 10%, 5%, or less) water.

The cryogels of the invention comprises pores large enough for a cell to travel through. For example, the cryogel contains pores of 20-500 μm in diameter, e.g., 20-300 μm, 30-150 μm, 50-500 μm, 50-450 μm, 100-400 μm, 200-500 μm. In some cases, the hydrated pore size is 1-500 μm (e.g., 10-400 μm, 20-300 μm, 50-250 μm).

Injectable cryogels can also be produced in a form in which pharmaceuticals or other bioactive substances (e.g. growth factors, DNA, enzymes, peptides, drugs, etc) are incorporated for controlled drug delivery.

In some embodiments, injectable cryogels are further functionalized by addition of a functional group chosen from the group consisting of: amino, vinyl, aldehyde, thiol, silane, carboxyl, azide, alkyne. Alternatively, the cryogel is further functionalized by the addition of a further cross-linker agent (e.g. multiple arms polymers, salts, aldehydes, etc). The solvent can be aqueous, and in particular acidic or alkaline. The aqueous solvent can comprise a water-miscible solvent (e.g. methanol, ethanol, DMF, DMSO, acetone, dioxane, etc).

The cryo-crosslinking takes place in a mold and the injectable cryogels can be degradable. The pore size can be controlled by the selection of the main solvent used, the incorporation of a porogen, the freezing temperature and rate applied, the cross-linking conditions (e.g. polymer concentration), and also the type and molecule weight of the polymer used.

In some examples, the composition comprises a cell adhesion composition chemically linked, e.g., covalently attached, to the polymer. For example, the cell adhesion composition comprises a peptide comprising an RGD amino acid sequence. In other examples, the cryogel composition (e.g., gelatin) has cell-adhesive properties. In some cases, the cryogel (e.g., gelatin cryogel) is not modified with a cell adhesive molecule, such as arginine-glycine-aspartate (RGD).

For cell therapy, the composition comprises a eukaryotic cell in one or more of the open interconnected pores. For example, the eukaryotic cell comprises a live attenuated cancer cell (e.g., irradiated cell acts as cancer antigen). Exemplary cancer cells include but are not limited to melanoma cells, breast cancer cells, central nervous system (CNS) cancer cells, lung cancer cells, leukemia cells, multiple myeloma cells, renal cancer cells, malignant glioma cells, medulloblastoma cells, colon cancer cells, stomach cancer cells, sarcoma cells, cervical cancer cells, ovarian cancer cells, lymphoma cells (e.g., Non-Hodgkin's lymphoma cells), pancreatic cancer cells, prostate cancer cells, thyroid cancer cells, rectal cancer cells, endometrial cancer cells, and bladder cancer cells. In another example, the cell is a stem cell, progenitor, or other cell that contributes to tissue repair or regeneration.

The hydrogel/cryogel, if to be used to transplant cells, comprises pores to permit the structure to be seeded with cells and to allow the cells to proliferate and migrate out to the structure to relocate to bodily tissues such as the injured or diseased muscle in need of repair or regeneration. For example, cells are seeded at a concentration of about $1\times10^3$ to $1\times10^8$ cells/mL (e.g., about $5\times10^3$ to $5\times10^7$ cells/mL, or about $1\times10^4$ to $1\times10^7$ cells/mL) and are administered dropwise onto a dried hydrogel/cryogel device. For example, the cells are seeded in a cryogel having a volume (when hydrated) of 1-500 uL (e.g., 10-250 uL, 20-100 uL, or 40-60 uL, or about 50 uL). The dose of the gel/device to be delivered to the subject is scaled depending on the magnitude of the injury or diseased area, e.g., one milliliter of gel for a relatively small defect and up to 50 mL of gel for a large wound. Preferably, the hydrogel/cryogel comprises macropores, e.g., pores that are characterized by a diameter of 2 μm-1 mm. The average pore size comprises 200 μm. Cells can move into and out of the cryogel via the open interconnected pores as a typical cell comprises a diameter or about 20 μm. The gel delivery devices are suitable for treatment of human beings, as well as animals such as horses, cats, or dogs.

Optionally, the device comprises a biomolecule in one or more of the open interconnected pores. Biomolecules include small molecule compounds (e.g., less than 1000 daltons in molecular mass), nucleic acids, proteins or fragments thereof, peptides. Biomolecules are purified naturally-occurring, synthetically produced, or recombinant compounds, e.g., polypeptides, nucleic acids, small molecules, or other agents. For example, the compositions include a chemotactic protein, granulocyte macrophage-colony stimulating factor (GM-CSF), pathogen-associated molecular patterns (PAMPs) such as CpG oligodeoxynucleotide (CpG-ODN), and cancer antigens or other antigens. The compositions, e.g., antigens, described herein are purified. Purified compounds/molecules are at least 60% by weight (dry weight) the compound/molecule of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis. Exemplary biomolecules include GM-CSF, large nucleic acid compositions such as plasmid DNA, and smaller nucleic acid compositions such as CpG-ODN. Other exemplary biomolecules include cancer antigens, e.g., derived from one or more of the cancers listed above, e.g., purified cancer antigens.

For example, the cryogel contains 1-10 ug of GM-CSF. In some examples, the cryogel has a volume of 1-500 uL (e.g., 10-250 uL, 20-100 uL, or 40-60 uL, or about 50 uL). In some cases, the nucleic acid biomolecule comprises a CpG nucleic acid oligonucleotide. For example, the CpG ODN is incorporated into the cryogel by mixing free CpG ODN with crosslinked gelatin. In other cases, the CpG ODN is incorporated into the cryogel by i) condensing the CpG ODN into nanoparticles to form CpG ODN condensates, and ii) crosslinking the gelatin with the CPG ODN condensates. Alternatively, the CpG ODN is covalently bound to the cryogel or the CpG ODN is ionically bonded to the cryogel.

In some examples, the device recruits a cell into the cryogel upon and after injection into a subject. The cell is recruited into one or more of the open interconnected pores of the cryogel. For example, the recruited cell comprises an immune cell, e.g., an antigen presenting cell (APC), a granulocyte, a macrophage, T cell (e.g., cytotoxic T cell or regulatory T cell), B cell, natural killer (NK) cell, or dendritic cell (DC). For example, the T cell is a cytotoxic T cell or a regulatory T cell. In some cases, the cryogel is degraded by one or more recruited cells (e.g., by a protease, such as a matrix metalloproteinase, expressed by the recruited cell). The cryogel is degraded at a rate dependent on the number of cells recruited into the cryogel.

Preferably, the cryogel compositions are injectable through a hollow needle. For example, the scaffold composition is injectable through a 16-gauge, an 18-gauge, a 20-gauge, a 22-gauge, a 24-gauge, a 26-gauge, a 28-gauge, a 30-gauge, a 32-gauge, or a 34-gauge needle. Upon compression or dehydration, the composition maintains structural integrity and shape memory properties, i.e., after compression or dehydration, the composition regains its shape after it is rehydrated or the shear forces of compression are removed/relieved. The scaffold composition also maintains structural integrity in that it is flexible (i.e., not brittle) and does not break under sheer pressure.

In some examples, the cryogel/device is between 0.01 $mm^3$ and 100 $mm^3$. For example, the cryogel/device is between 1 $mm^3$ and 75 $mm^3$, between 5 $mm^3$ and 50 $mm^3$, between 10 $mm^3$ and 25 $mm^3$. Preferably, the cryogel/device is between 1 $mm^3$ and 10 $mm^3$ in size.

The shape of the cryogel is dictated by a mold and can thus take on any shape desired by the fabricator, e.g., various sizes and shapes (disc, cylinders, squares, strings, etc.) are prepared by cryogenic polymerization. Injectable cryogels can be prepared in the micrometer-scale to millimeter-scale. Volume varies from a few hundred $μm^3$ (e.g., 100 $um^3$) to over 100 $mm^3$. An exemplary scaffold composition is between 100 $um^3$ to 100 $mm^3$ in size (e.g., between 1 $mm^3$ and 10 $mm^3$ in size). In another example, the cryogel is defined by volume. For example, the cryogel scaffold composition comprises 5-100 uL (e.g., 25 μL) in volume in a hydrated state. The gels are hydrated in an aqueous medium. Exemplary cryogel compositions are typically in the range of 10-70 μL in volume and may be larger or smaller depending on the use and site to be treated.

The cryogel acts as a sponge. The cryogels are sterilized. In some applications, the cryogels are hydrated, loaded with cells or other compounds (e.g., small molecules and other compounds, nucleic acids, or proteins/peptides) and loaded into a syringe or other delivery apparatus. For example, the syringes are prefilled and refrigerated until use. In another example, the cryogel is dehydrated, e.g., lyophylized, optionally with a drug or other compound loaded in the gel and stored dry or refrigerated. Prior to administration, the cryogel-loaded syringe or apparatus is contacted with a solution containing cells and/or other compounds to be delivered. For example, the barrel of the cryogel pre-loaded syringe is filled with a physiologically-compatible solution, e.g., phosphate-buffered saline (PBS). In practice, the cryogel is administered to a desired anatomical site followed by the volume of solution, optionally containing other ingredients, e.g., cells or therapeutic compounds. For example, a 25 μL cryogel is administered with approximately 200 μL of solution. The cryogel is then rehydrated and regains its shape integrity in situ. The volume of PBS or other physiologic solution administered following cryogel placement is generally about 10 times the volume of the cryogel itself.

Cell viability is minimally affected or unaffected by the shear thinning process, and gel/cell constructs stay fixed at the point of introduction. As such, these gels are useful for the delivery of cells and other compounds to target biological sites in therapeutic methods such as tissue regeneration (cell therapy, drug delivery) efforts.

The cryogel also has the advantage that, upon compression, the cryogel composition maintains structural integrity and shape memory properties. For example, the cryogel is injectable through a hollow needle. For example, the cryogel returns to its original geometry after traveling through a needle (e.g., a 16 gauge (G) needle, e.g., having an 1.65 mm inner diameter). Other exemplary needle sizes are 16-gauge, an 18-gauge, a 20-gauge, a 22-gauge, a 24-gauge, a 26-gauge, a 28-gauge, a 30-gauge, a 32-gauge, or a 34-gauge needle.

The polymer chains of the hydrogel/cryogel are covalently crosslinked and/or oxidized. Such hydrogels are suitable for minimally-invasive delivery. Prior to delivery into the human body, such a hydrogel is lyophilized and compressed prior to administration to a subject for the regeneration of muscle tissue. Minimally-invasive delivery is characterized by making only a small incision into the body. For example, the hydrogel is administered to a muscle of a subject using a needle or angiocatheter.

Injectable cryogels have been designed to pass through a hollow structure, e.g., very fine needles, such as 18-30 G needles, as a tissue filler for applications in cosmetic surgery, for tissue augmentation, and tissue repair which may be due to injury caused by disease and external trauma. The injectable cryogels may be molded to a desired shape, in the form of rods, square, disc, spheres, cubes, fibers, foams. In some situations, the injectable cryogels can be used as scaffolds for cell incorporation. In some cases, the cryogel comprises the shape of a disc, cylinder, square, rectangle, or string. For example, the cryogel composition is between 100 um$^3$ to 100 mm$^3$ in size, e.g., between 1 mm$^3$ to 50 mm$^3$ in size. For example, the cryogel composition is between 1 mm in diameter to 50 mm in diameter (e.g., around 5 mm) Optionally, the thickness of the cryogel is between 0.2 mm to 50 mm (e g, around 2 mm) The formed cryogel is mixed with cells to provide tissue engineered products, or can be used as a bio-matrix to aid tissue repair or tissue augmentation. The incorporated cells can be any mammalian cells (e.g. stem cells, fibroblasts, osteoblasts, chrondrocytes, immune cells, etc).

The cryogel also has the advantage of inducing a minimal adverse host response (e.g., minimal immune rejection and/or minimal harmful acute inflammation) after injection into a subject.

Therapeutic and cosmetic uses are described throughout the specification. Exemplary applications include use as a dermal filler, in drug delivery, as a wound dressing, for post surgical adhesion prevention, and for repair and/or regenerative medical applications such as cell therapy, gene therapy, tissue engineering, immunotherapy.

For example, a method for repairing, regenerating, or restructuring a tissue comprises administering to a subject the device/cryogel composition described above. If the cryogel contains cells, the cells retain their viability after passage through the syringe or delivery apparatus, cells proliferate in the device/cryogel, then leave the cryogel composition to function outside of the gel and in the bodily tissues of the recipient subject. For example, the cryogel is administered subcutaneously as a dermal filler, thereby restructuring the tissue, e.g., dermal tissue. In another example, the cryogel device comprises a stem cell and the composition/device is administered to a damaged or diseased tissue of a subject, thereby repairing or regenerating the tissue, e.g., muscle, bone, kidney, liver, heart, bladder, ocular tissue or other anatomic structures.

In another example, the cryogel compositions are used in a method for delivering genetic material to a tissue, e.g., to deliver plasmid DNA.

The invention also features a method for eliciting an immune response, comprising administering to a subject a cryogel composition described herein, where the composition comprises a microbial pathogen, microbial antigen, cancer cell lysate, cancer antigen, or cancer cell to which an immune response is elicited. For example, cancer cells include but are not limited to cells from a melanoma, a breast cancer, a lung cancer, a lymphoma (e.g., Non-Hodgkin's lymphoma cells), a leukemia, a stomach cancer, a liver cancer, a central nervous system cancer, a sarcoma, a central nervous system (CNS) cancer, a multiple myeloma, a renal cancer, a malignant glioma, a medulloblastoma, a colon cancer, a cervical cancer, an ovarian cancer, a pancreatic cancer, a prostate cancer, a thyroid cancer, a rectal cancer, an endometrial cancer, a uterine cancer, and a bladder cancer. For example, a cancer lysate or cancer antigen is derived from a cancer cell described herein.

For example, a microbial pathogen includes but is not limited to a fungus, a bacterium (e.g., *Staphylococcus* species, *Staphylococcus aureus*, *Streptococcus* species, *Streptococcus pyogenes*, *Pseudomonas aeruginosa*, *Burkholderia cenocepacia*, *Mycobacterium* species, *Mycobacterium tuberculosis*, *Mycobacterium avium*, *Salmonella* species, *Salmonella typhi*, *Salmonella typhimurium*, *Neisseria* species, *Brucella* species, *Bordetella* species, *Borrelia* species, *Campylobacter* species, *Chlamydia* species, *Chlamydophila* species, *Clostrium* species, *Clostrium botulinum*, *Clostridium difficile*, *Clostridium tetani*, *Helicobacter* species, *Helicobacter pylori*, *Mycoplasma* pneumonia, *Corynebacterium* species, *Neisseria gonorrhoeae*, *Neisseria meningitidis Enterococcus* species, *Escherichia* species, *Escherichia coli*, *Listeria* species, *Francisella* species, *Vibrio* species, *Vibrio* cholera, *Legionella* species, or *Yersinia pestis*), a virus (e.g., adenovirus, Epstein-Barr virus, Hepatitis A virus, Hepatitis B virus, Hepatitis C virus, Herpes simplex virus type 1, 2, or 8, human immunodeficiency virus, influenza virus, measles, Mumps, human papillomavirus, poliovirus, rabies, respiratory syncytial virus, rubella virus, or varicella-zoster virus), a parasite or a protozoa (e.g., *Entamoeba histolytica*, *Plasmodium*, *Giardia lamblia*, *Trypanosoma brucei*, or a parasitic protozoa such as malaria-causing *Plasmodium*). For example, a microbial antigen is derived from a microbial cell described herein.

For example, the cancer cell or microbial pathogen cell is a live attenuated (e.g., /irradiated) cell. In the case of microbial pathogens, heat-killed bacteria are optionally used. In some cases, the cell is obtained from the patient to be treated, e.g., by biopsy, attenuated, and then used as a component of the device.

In some examples, the cancer cell is a melanoma cell (e.g., B16-F10 cancer cell or patient-derived, autologous attenuated cell) or a breast cancer cell (e.g., a HER-2/neu-over-expressing breast cancer cell such as a patient-derived, autologous cancer cell). In some examples, the cryogel composition contains a protein or polypeptide (e.g., recombinant protein) or a plasmid DNA encoding for the protein or polypeptide derived from a microbial pathogen or cancer cell described herein. The cryogel composition (e.g., in the form of a device) is administered prophylactically or therapeutically.

In some embodiments, the device is injected into the subject once every day to once every 10 years (e.g., once every day, once every week, once every two weeks, once every month, once every two months, once every 3 months, once every 4 months, once every 5 months, once every 6 months, once every year, once every 2 years, once every 3 years, once every 4 years, once every 5 years, once every 6 years, once every 7 years, once every 8 years, or once every 10 years). In other examples, the device is injected into the subject once to 5 times (e.g., one time, twice, 3 times, 4 times, 5 times, or more as clinically necessary) in the subject's lifetime.

The injected device comprises at least $0.5 \times 10^6$ (e.g., at least $0.75 \times 10^6$, at least $1 \times 10^6$, at least $1.5 \times 10^6$, at least $2 \times 10^6$, at least $5 \times 10^6$, at least $10 \times 10^6$, or more) immune cells at least 1 day (e.g., at least 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or more) after injection into the subject.

In some cases, the injected device induces an increase in the number of immune cells in a lymph node (e.g., draining lymph node) or spleen at least 1 day (e.g., at least 2, 3, 4, 5, 6, 7, 8, 9, 10, 11, 12, 13, 14, 15, 16, 17, 18, 19, 20 or more days) after injection into the subject.

Exemplary immune cells include DC (e.g., CD11b+, CD11c+, plasmacytoid, and CD8+ DC), T cells (e.g., cytotoxic T cells and/or Treg cells), B cells, macrophages, granulocytes, and natural killer cells. For example, the immune cells comprise CD3+ T cells, CD8+ T cells, and/or FoxP3+ Treg cells. In some cases, the ratio of CD8+ effector T cells to FoxP3+ Treg cells is at least 0.5-fold (at least 0.75-fold, at least 1-fold, 2-fold, 3-fold, 4-fold, 5-fold, 7-fold, 10-fold, 15-fold, or more). In some examples, at least 40% (e.g., at least 40%, 45%, 50%, 55%, 60%, 65%, 70%, 75%, 80%, 85%, or more) of the immune cells are plasmacytoid DC. In other examples, at least 20% (e.g., at least 20%, 25%, 30%, 35%, 40%, 45%, 50%, 55%, 60%, 65%, or more) of the immune cells are CD8+ DC, or CD11c+ CD141+ human DC. See, e.g., Bachem et al. J. Exp. Med. 207(2010):1273-81; and Lauterbach et al. J. Exp. Med. 207(2010):2703-17, incorporated herein by reference.

The injected device comprises $10^7$ or fewer (e.g., $1 \times 10^7$, $8 \times 10^6$, $5 \times 10^6$, $4 \times 10^6$, $3 \times 10^6$, $2 \times 10^6$, $1 \times 10^6$, $5 \times 10^5$, $2 \times 10^5$, $1 \times 10^5$, $1 \times 10^4$, or fewer) cells (e.g., immune cells) at least 15 days (e.g., at least 15, 16, 17, 18, 19, 20, 21, 22, 23, 24, 25, 26, 27, 28, 29, 30, or more days) after injection. Exemplary immune cells are described above.

The injected device and/or tissue surrounding the device (e.g., within 10 cm of the injected device, such as within 10 cm, 9 cm, 8 cm, 7 cm, 6 cm, 5 cm, 4 cm, 3 cm, 2 cm, 1 cm, or fewer) comprises an elevated level of a cytokine compared to the level of the cytokine at a site in the subject more than 10 cm away from the injected device (e.g., at a different site in the body), e.g., more than 10 cm away from a boundary, edge, or center of the injected device. Alternatively, the injected device and/or tissue surrounding the device (e.g., within 10 cm of the injected device, such as within 10 cm, 9 cm, 8 cm, 7 cm, 6 cm, 5 cm, 4 cm, 3 cm, 2 cm, 1 cm, or fewer) comprises an elevated level of a cytokine compared to the level of the cytokine in the subject at the site of injection prior to injection. In some examples, the injected device and/or tissue surrounding the device (e.g., within 10 cm of the injected device, such as within 10 cm, 9 cm, 8 cm, 7 cm, 6 cm, 5 cm, 4 cm, 3 cm, 2 cm, 1 cm, or fewer) comprises an elevated level of a cytokine compared to the level of the cytokine in an untreated subject. The level of the cytokine is elevated by at least 1.5-fold (e.g., at least 1.8-fold, 2-fold, 4-fold, 5-fold 7-fold, 10-fold, 15-fold, 20-fold, or more).

The cytokine comprises RANTES (regulated on activation, normal T cell expressed and secreted) (also called Chemokine (C-C motif) ligand 5 (CCL5)), eotaxin, IL-1α, IL-1β, IL-2, IL-3, IL-4, IL-5, IL-6, IL-9, IL-10, IL-12, IL-13, IL-17, GM-CSF, macrophage inflammatory protein-1α (MIP-1α), macrophage inflammatory protein-1β (MIP-1β), keratinocyte-derived chemokine (KC), tumor necrosis factor-α (TNF-α), granulocyte-colony stimulating factor (G-CSF), interferon-α (IFN-α), interferon-γ (IFN-γ), or monocyte chemotactic protein-1 (MCP-1).

In some embodiments, the subject to be administered a cryogel/device of the invention does not have a cancer, has not been diagnosed with a cancer, or has been diagnosed with a cancer.

In some cases, the device increases the survival time of a subject diagnosed with a cancer by at least 1 month (e.g., at least 1, 2, 3, 4, 5, 6, 7, 8, 9, 10, or 11 months or more, or at least 1, 2, 3, 4, 5, 6, 7, 8, 9, 10, 11, 12, 13, 14, or 15 years or more) compared to the survival time of an untreated subject. Increased survival time is determined by comparing the prognosis for survival in the subject from a time period prior to administration of the device to the prognosis for survival in the subject following administration of the device, wherein an increase in predicted survival time indicates that the treatment increased survival of the subject following administration of the device.

In other cases, the device stabilizes the size (e.g., volume, mass, or longest diameter) of an existing tumor, thereby preventing disease progression. For example, the size of an existing tumor after administration of the device remains within 30% (e.g., within 25% 20%, 15%, 10%, 5%, 2.5%, 1%, or less) of the original size before administration of the device. Alternatively, the device decreases the size (e.g., volume, mass, or longest diameter) of an existing tumor. For example, the device decreases the size (e.g., volume, mass, or longest diameter) of an existing tumor by at least 1.5-fold (e.g., at least 2-fold, 3-fold, 4-fold, 5-fold, 6-fold, 7-fold, 8-fold, 9-fold, 10-fold, 15-fold, 20-fold, or more) compared to the size of the tumor prior to injection of the device.

The vaccine device of the invention remains effective in eliciting the immune response at least 100 days (e.g., at least 120 days, 150 days, 180 days, 1 year, 2 years, 3 years, 4 years, 5 years, 6 years, 7 years, 8 years 9 years, 10 years or more) after injection.

The device is injected, e.g., into the subcutis of a subject. In other examples, the device is injected intradermally, intramuscularly, into an organ, or directly into a tumor. The device is injected into at least 1 site (e.g., at least 2, 3, 4, 5, 6, 7, 8, 9, 10, or more sites) in the subject.

In some examples, the device reduces the rate of tumor growth in the subject compared to the rate of tumor growth in an untreated subject. For example, the device reduces the rate of tumor growth in the subject by at least 2-fold compared to the rate of tumor growth in an untreated subject. For example, the device reduces the rate of tumor growth in the subject by at least 2-fold (e.g., at least 2-fold, 3-fold, 4-fold, 5-fold, 7-fold, 10-fold, 15-fold, or more) compared to the rate of tumor growth in a subject administered with a hydrogel lacking cancer cells (e.g., attenuated cancer cells).

Bioactive factors such as polynucleotides, polypeptides, or other agents (e.g., antigens) are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant that a nucleotide, polypeptide, or other compound has been separated from the components that naturally accompany it. Typically, the nucleotides and polypeptides are substantially pure when they are at least 60%, 70%, 80%, 90%, 95%, 99%, or even 100%, by weight, free from the proteins and naturally-occurring organic molecules with they are naturally associated. Examples include synthesized compounds, recombinant compounds (e.g., peptides, proteins, nucleic acids) or purified compounds, e.g., purified by standard procedures including chromatographic methods.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present invention further include molecules produced synthetically, as well as any nucleic acids that have been altered chemically and/or that have modified backbones.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 4A is a photograph showing alginate cryogel scaffolds (white) and rhodamine-labeled alginate scaffolds (pink). Bioluminescence B16-F10 cells were seeded on 1% RGD-modified MA-Alginate cryogels at a concentration of $200 \times 10^3$ cells/scaffold. Luciferase transected melanoma cells were cultured for 6 hr into rhodamine-labeled alginate cryogels before injection into mice. FIG. 4B is a photograph showing optical live imaging to demonstrate that macroporous alginate gels are suitable for homogenous encapsulation and distribution of bioluminescent B16 cells. FIG. 4C is a photograph showing scanning electron microscope (SEM) imaging to demonstrate that macroporous alginate gels are suitable for homogenous encapsulation and distribution of bioluminescent B16 cells. FIG. 4D is a photograph showing live fluorescence imaging of subcutaneous injections of gels. FIG. 4E is a photograph showing live fluorescence imaging of subcutaneous injections of gels at 2 days post-injection. FIG. 4F is a photograph showing live fluorescence imaging of subcutaneous injections of gels at 9 days post-injection. Bioluminescent B16-cells were visualized by live imaging. Arg-Gly-Asp (RGD;

cell-adhering peptide)-Alginate scaffolds significantly promoted target delivery of cells compared to unmodified gels. By contrast, injection of free cells (bolus) did not promote localization of cells (bioluminescent signal absent).

Figure 5:
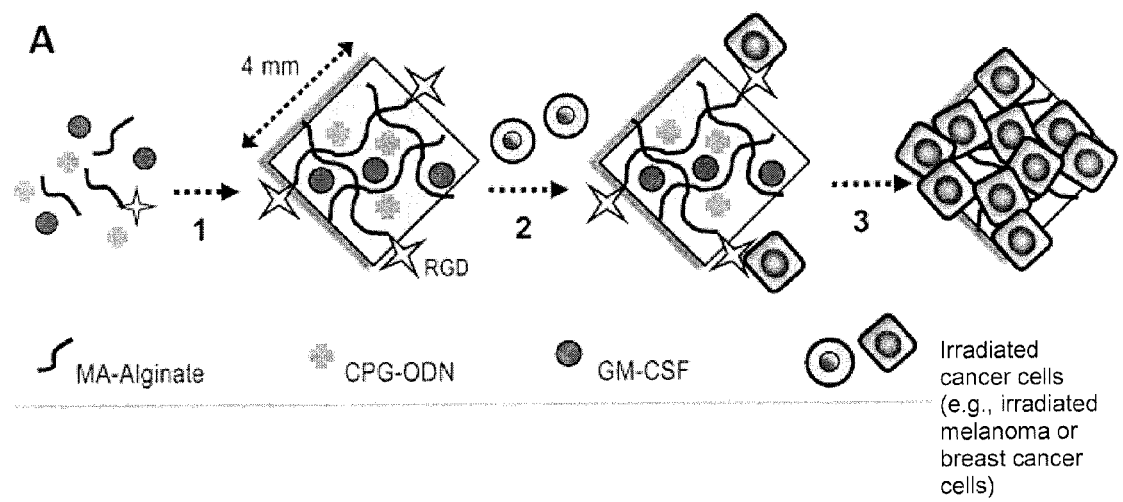
Figure 5:
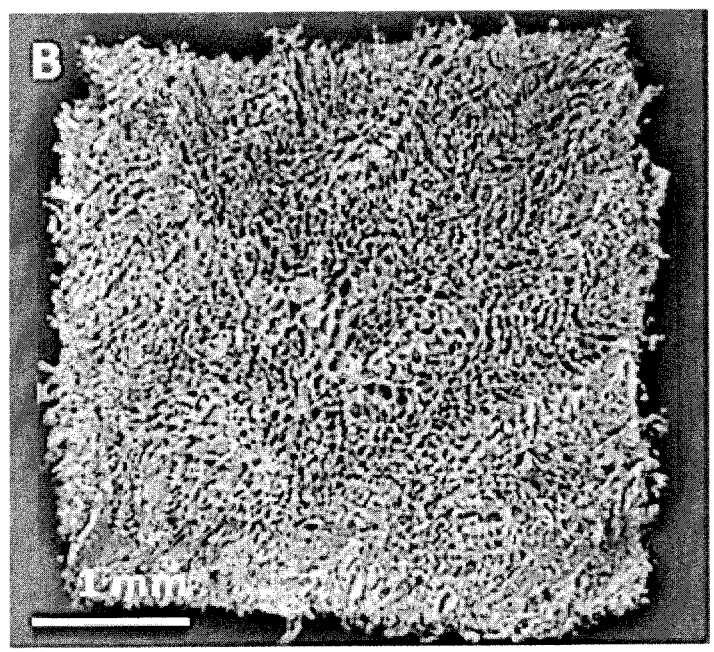
Figure 5:
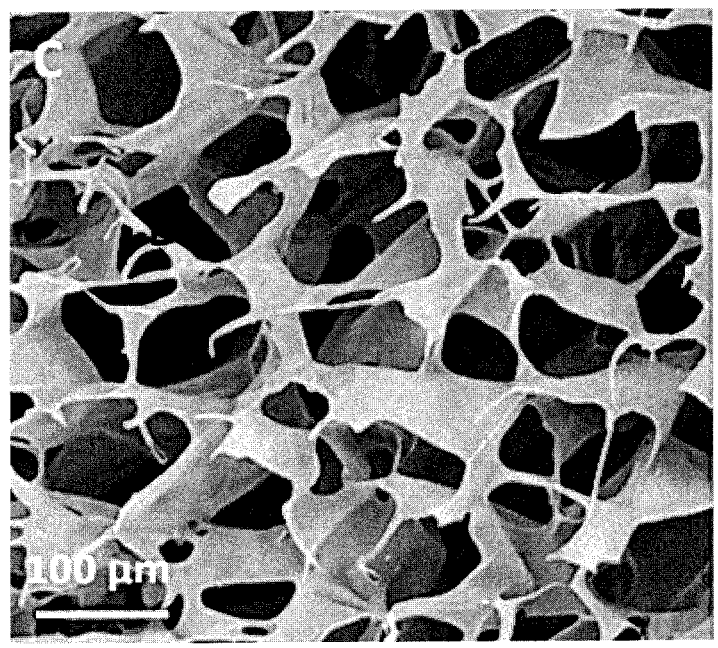
Figure 5:
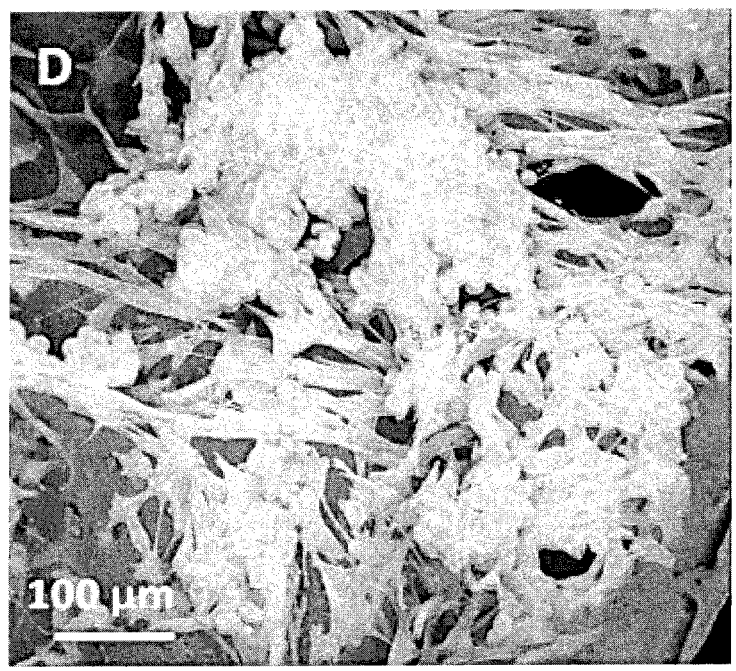
Figure 5:
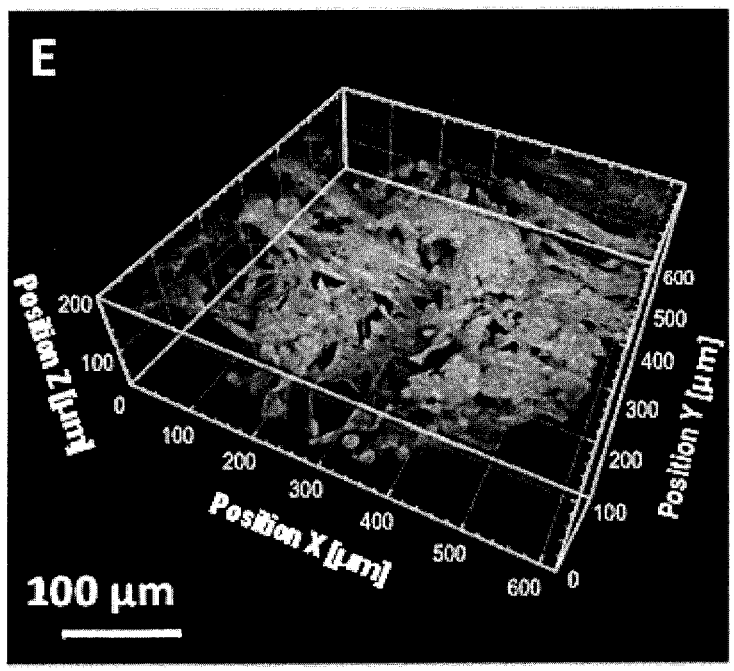

FIG. 5A is a schematic showing preparation of an autologous (e.g., syngeneic) alginate-based active cryogel vaccine containing living attenuated B16-F10 melanoma cells or living attenuated HER-2/neu-overexpressing breast cancer cells for the prophylactic and therapeutic treatments of skin cancer or invasive mammary carcinoma, respectively, in mice (e.g., C57BL/6 mice). CpG-ODN (TLR9-based immune adjuvant) & GM-CSF (cytokine with adjuvant benefits) loaded RGD-modified alginate cryogels prepared by a cryogelation process at subzero temperature were seeded with irradiated B16-F10 cells or irradiated HER-2/neu-overexpressing breast cancer cells and incubated for 6 h prior to animal vaccination via subcutaneous injection. FIG. 5B is a scanning electron microscopy (SEM) image showing homogeneous macroporous microstructure throughout the square-shaped sponge-like gel construct. FIG. 5C is a SEM cross-sectional image of alginate cryogel showing interconnected macroporous network. FIG. 5D is a 2-D confocal micrograph displaying immobilization of irradiated B16-F10 cells on a typical RGD-containing cryogel after 6 h culture. FIG. 5E is a 3-D reconstructed confocal fluorescence micrograph of irradiated B16-F10 cells depicting cell-substratum adhesion, spreading, and elongation after 6 h culture in a cryogel vaccine.

Figure 6:
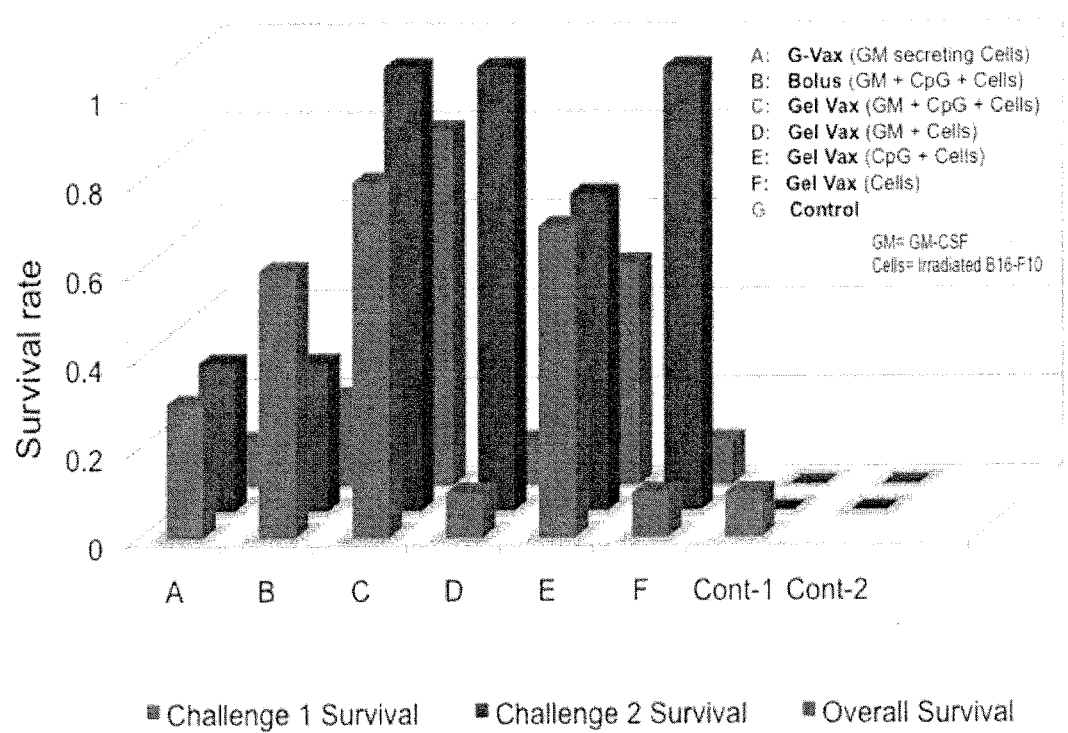

FIG. 6 is a bar graph showing immunity against B16F10 challenge induced by different vaccination protocols. Infection-mimicking microenvironment from injectable alginate-based cryogel conferred potent anti-tumor immunity. A comparison of the survival time in mice treated with Cryogels; (C) antigen+GM-CSF+CpG-ODN ($0.2 \times 10^6$ irradiated B16F10 melanoma cells+3 µg GM 100 µg CpG), antigen+ GM-CSF ($0.4 \times 10^6$-CSF+(D) 6 irradiated B16F10 melanoma cells+3 µg GM), (E) antigen+CpG-ODN ($0.4 \times 10^6$ irradiated B16F10 melanoma cells+100 µg CpG). Animals were also immunized using $0.4 \times 10^6$ B16F10 melanoma cells transduced with the murine GM-CSF gene (A) and bolus injections of $0.4 \times 10^6$ irradiated B16F10 melanoma cells+3 µg GM-CSF+100 µg CpG-ODN (B). Mice were challenged (Day 6) with $10^5$ B16-F10 melanoma tumor cells and monitored for the onset of tumor occurrence. Each group contained 10 mice.

Figure 7:
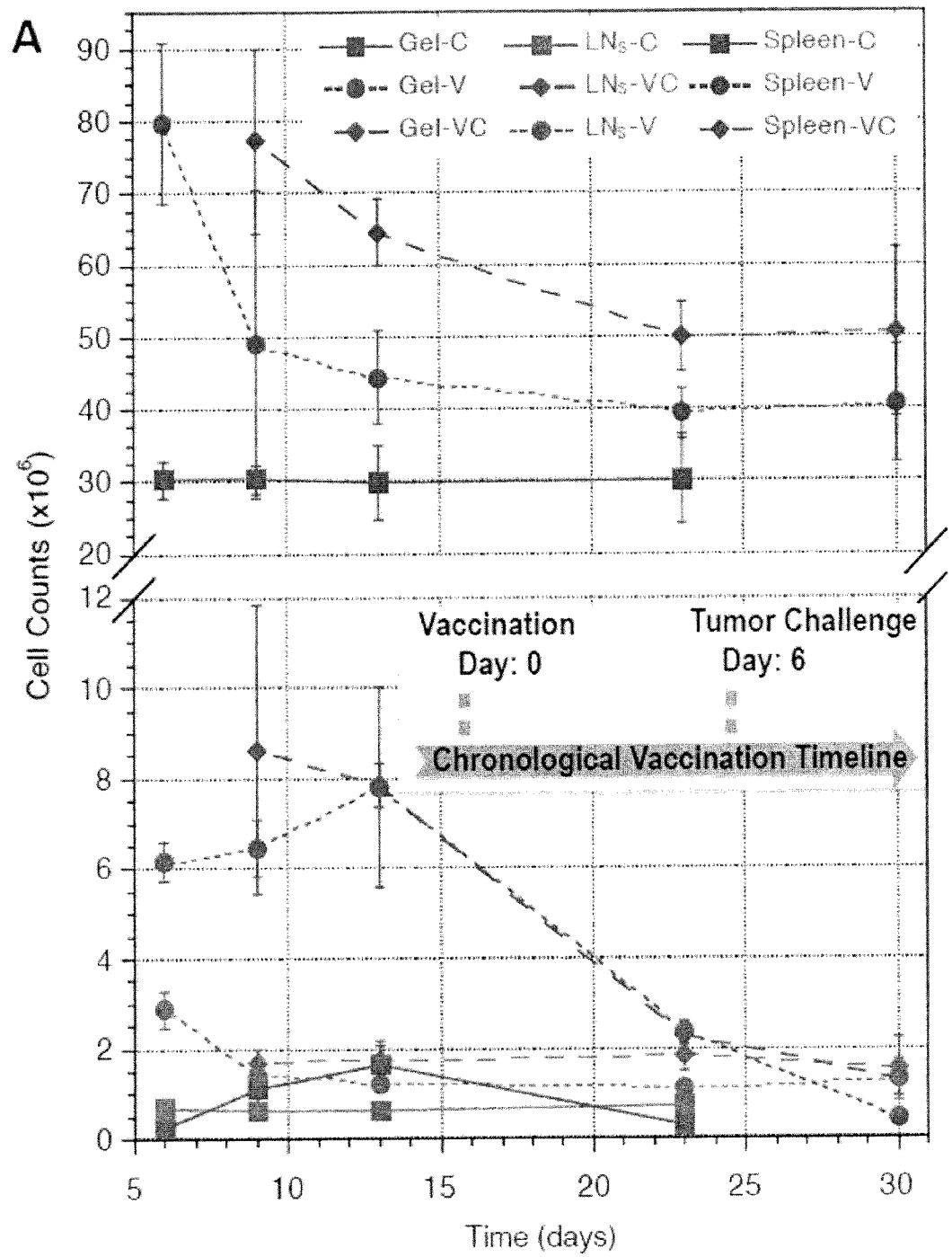
Figure 7:
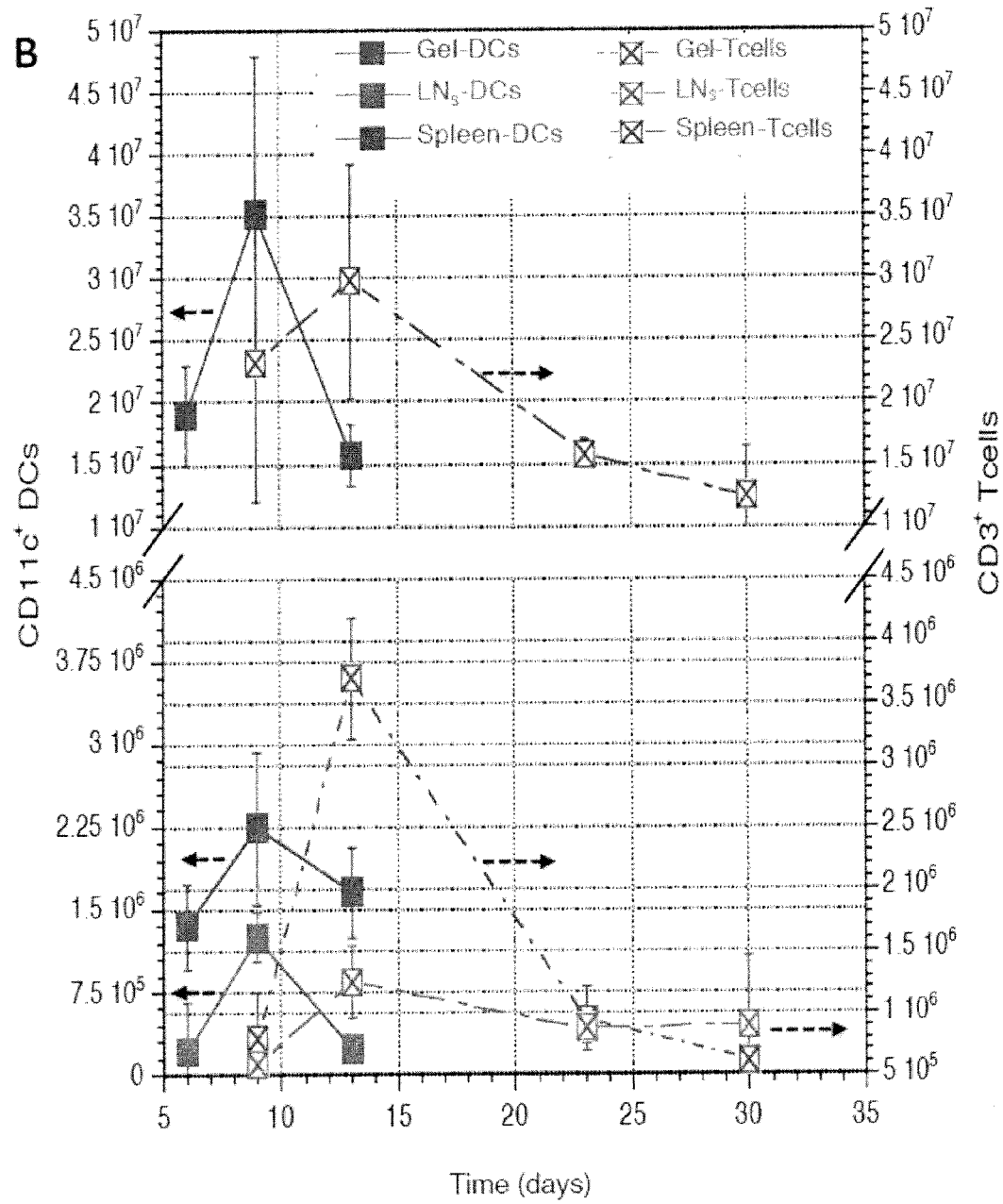

FIG. 7A is a line graph showing the degree of cell recruitment and expansion at the injection site and at secondary lymphoid organs (lymph nodes (LNs) and spleen) in response to cryogel vaccination and challenge. The in vivo proliferative responsiveness of the cells was assessed by cell counting. The inset shows the chronological order of the immunization and tumor challenge. FIG. 7B is a line graph showing that local delivery of cryogel vaccines promotes recruitment of CD11c(+) and proliferation of CD3(+) T cells. Cryogel vaccines co-delivering GM-CSF (1.5 µg), CpG-ODN (50 µg), and presenting attenuated B16F10 melanoma cells stimulate potent local and systemic CD11c(+) DC and CD3(+) T cells in secondary lymphoid organs (LNs and spleen) as well as in the cryogel scaffolds. C, V, and VC groups correspond to mice injected with blank cryogels at day 0 (C), mice immunized with cryogel vaccines at day 0 (V), and mice immunized with cryogel vaccines at day 0+tumor challenged at day 6 (VC), respectively. Values in (FIGS. 7A-B) represent mean and standard deviation (n=5).

Figure 8:
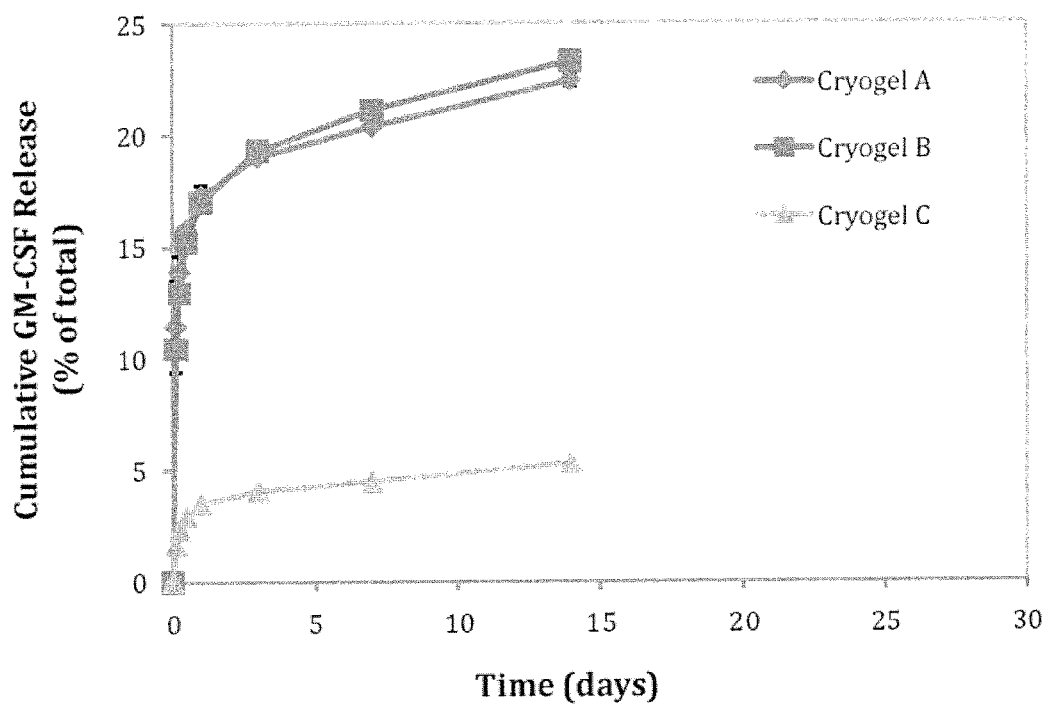

FIG. 8 is a line graph showing controlled release of GM-CSF for DC recruitment and programming. Cumulative release of GM-CSF from Alginate-based cryogel matrices over a period of 2 weeks; (A) 3 µg GM-CSF, (B) 3 µg GM-CSF+100 µg CpG-ODN, (C) PLG microsphere containing 3 µg GM-CSF. Values represent mean and standard deviation (n=5).

Figure 9:
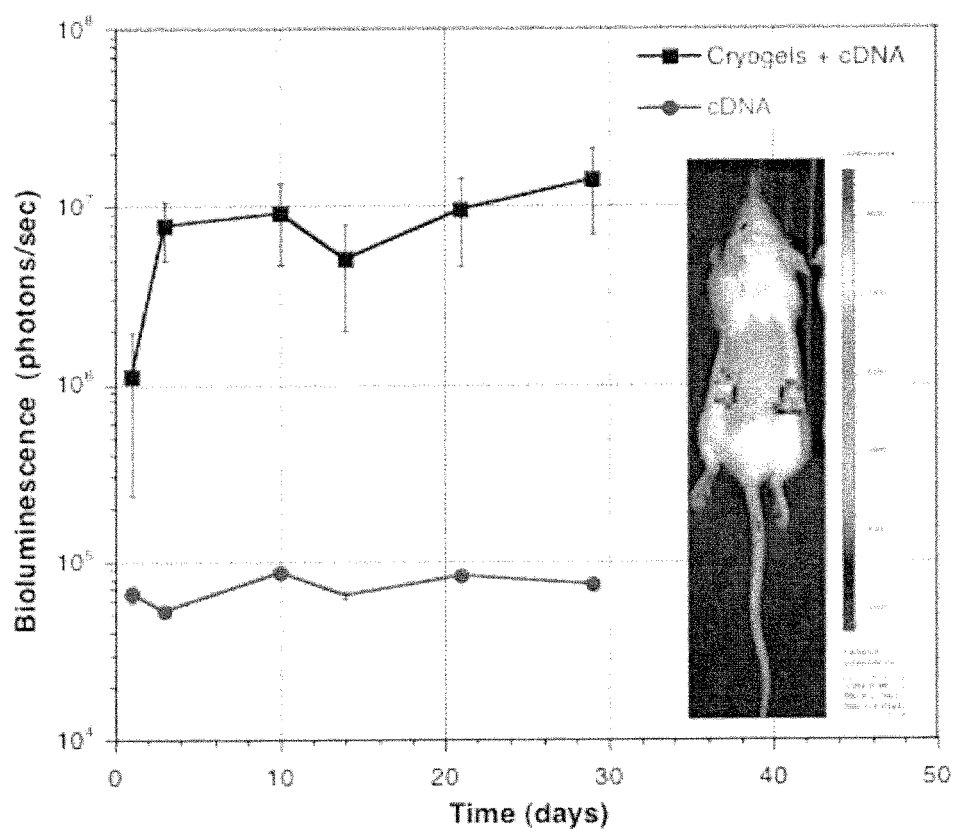

FIG. 9 is a line graph showing cryogel-enhanced plasmid DNA transfection. Relative bioluminescence over time for cells transfected with a luciferase expression plasmid (150 µg/cryogel, 2 injections/animal). Cryogels assist in efficient delivery and cell transfection of polyethylenimine (PEI)/plasmid DNA (blue) when compared to naked PEI/DNA (red). Values represent mean and standard deviation (n=5). The inset is a photograph that shows a representative localized light emission in response to application of firefly luciferin after 29 d post injection in mice inoculated with PEI/DNA-containing cryogels.

Figure 10:
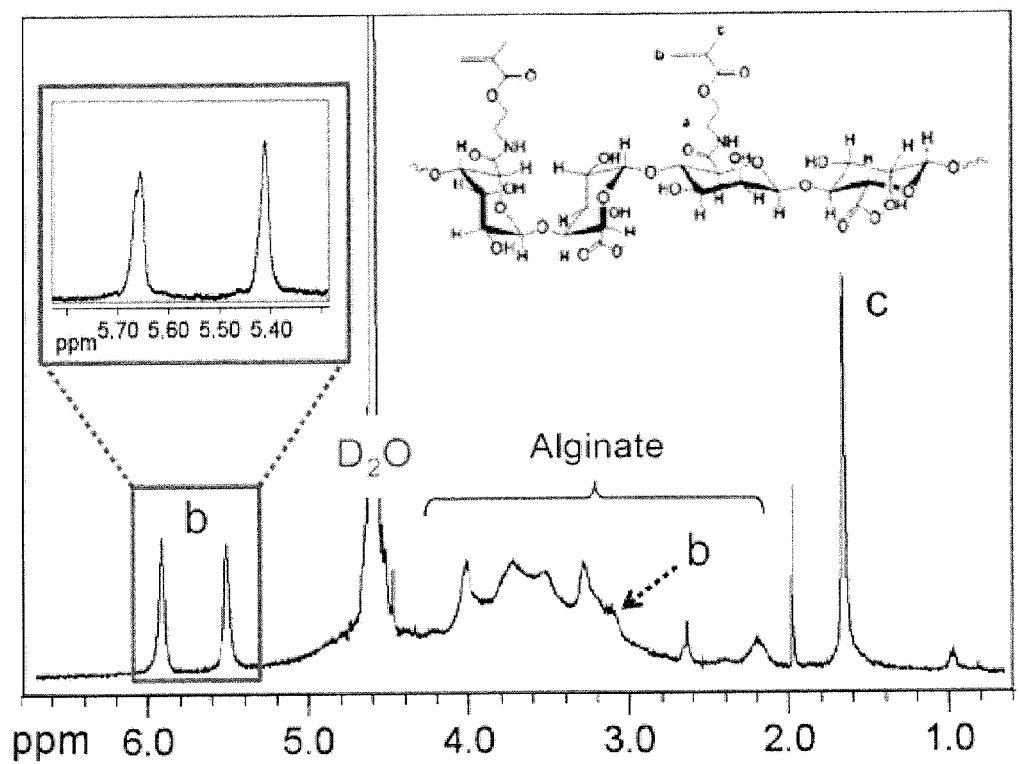

FIG. 10 is a nuclear magnetic resonance (NMR) spectrum showing the $^1$H NMR spectrum of MA-alginate with its characteristic vinylic peaks (~δ5.3-5.8 ppm). Deuterated water ($D_2O$) was used as solvent, and the polymer concentration was 1% (wt/vol). The efficiency of alginate methacrylation was calculated based on the ratio of the integrals for alginate protons to the methylene protons of methacrylate. MA-alginate macromonomer was found to have approximately a degree of methacrylation (DM) of 50%.

Figure 11:
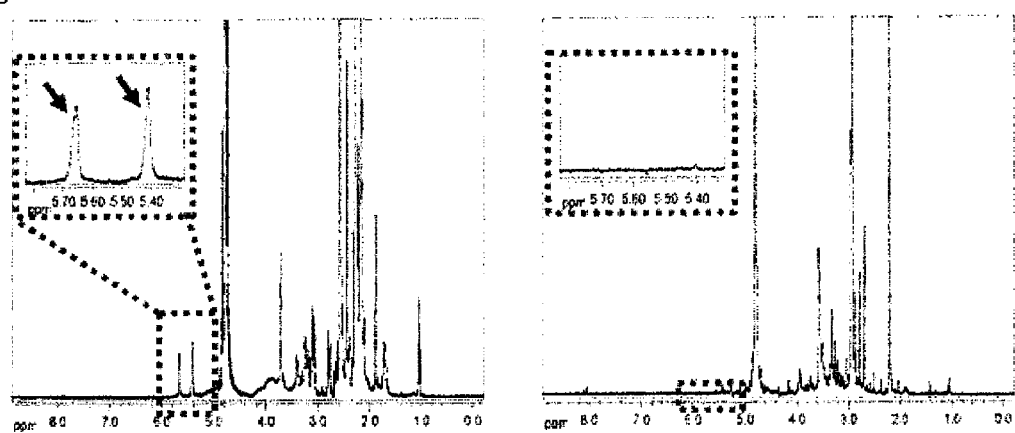

FIG. 11 is a set of two line graphs showing $^1$H NMR of uncross-linked (left) and cryopolymerized (right) 1% wt/vol MA-alginate in $D_2O$. Cryogelation is induced directly in an NMR tube. 1 mL of macromonomer solution containing the initiator system was transferred into the NMR tube before cryogenic treatment at −20° C. for 17 hr. The vinylic peaks (between δ5.3-5.8 ppm) disappeared after cryo-crosslinking. The conversion was evaluated by comparing the relative peaks of uncross-linked and cross-linked methylene protons.

Figure 12:
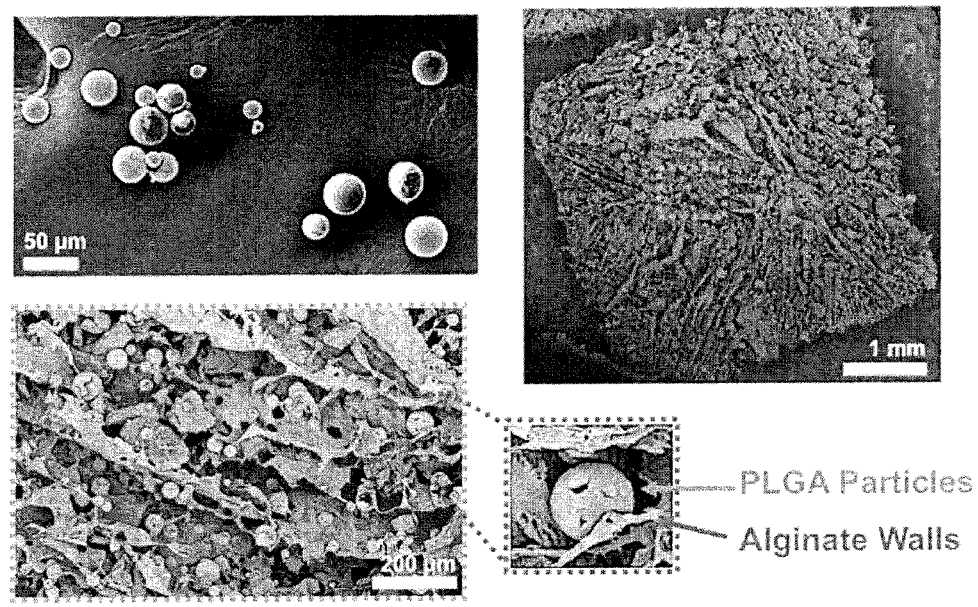

FIG. 12 is a series of four photographs showing scanning electron microscopic images of free PLGA microspheres (top left) and PLGA microspheres dispersed in a alginate square-shaped cryogel (top right and bottom).

Figure 13:
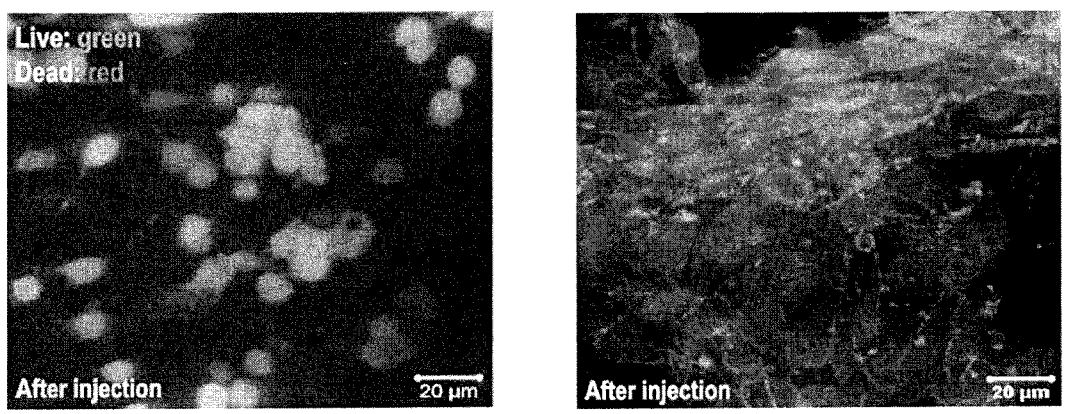

FIG. 13 is a series of two photographs showing that cells injected via the cryogels have a low apoptosis and cell death. In this example, a RGD-containing peptide was chemically attached to the cryogels to improve cell adhesion to the 3D-structure alginate-based scaffolds. Cell viability, spreading, and actin cytoskeleton organization process was assessed by confocal microscopy. Cells colonize the porous structure of the alginate-based cryogel and were observed to be growing inside the pores. (Left) live/dead cell viability assay of D1 mesenchymal stem cells (MSC, 1 d incubation post-injection) and (right) confocal image showing injected D1 MSC (6 d incubation post-injection) in RGD-modified MA-alginate cryogels.

Figure 14:
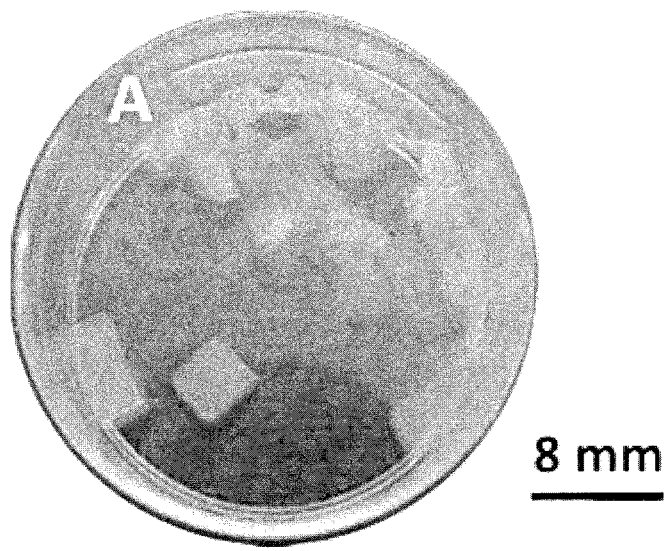
Figure 14:
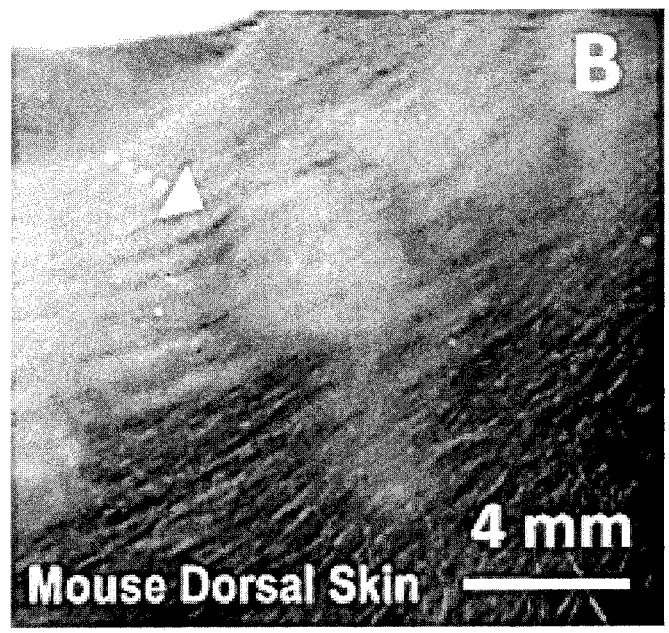

FIGS. 14A-B are a set of photographs depicting cryogel (4×4×1 mm) before (A) and after (B) syringe injection in the subcutis of a mouse. These photographs show that the injectable square-shaped alginate sponge-like cryogels have shape-memory properties.

Figure 15:
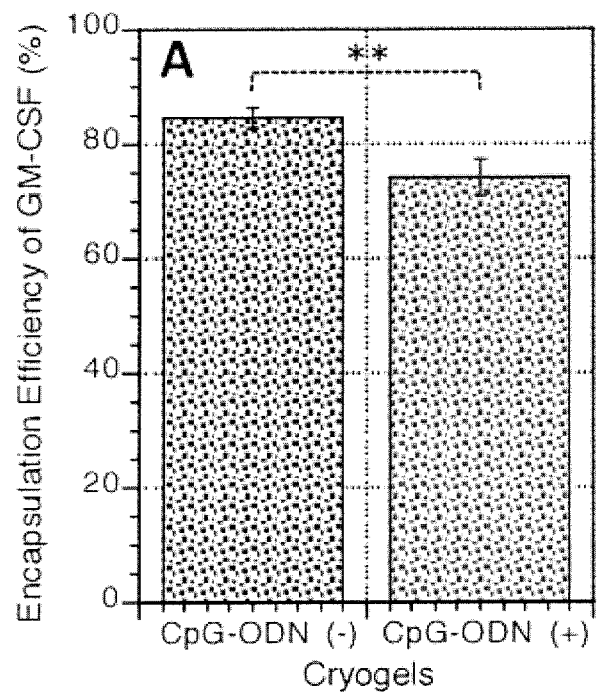
Figure 15:
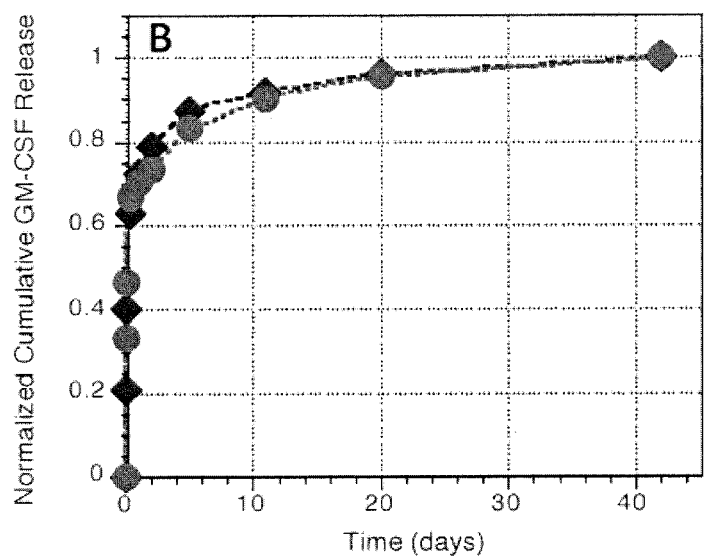
Figure 15:
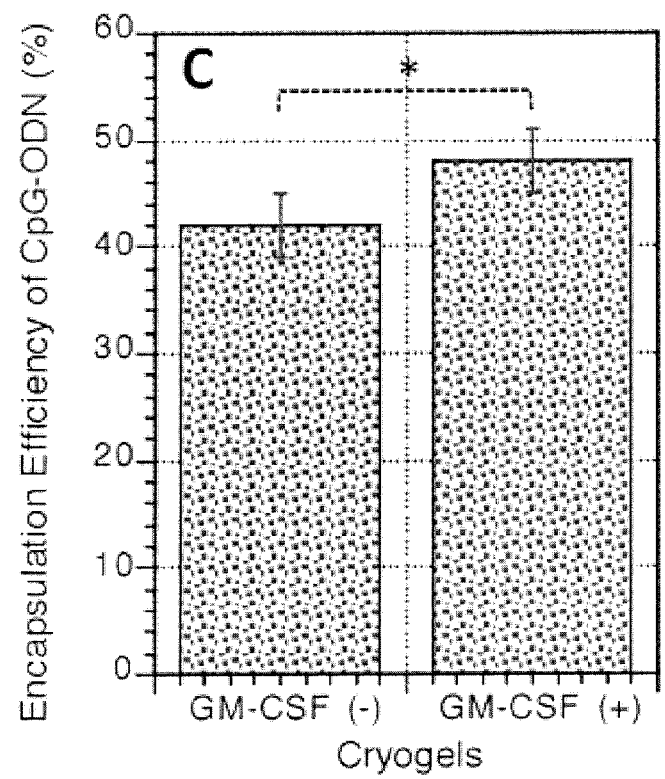
Figure 15:
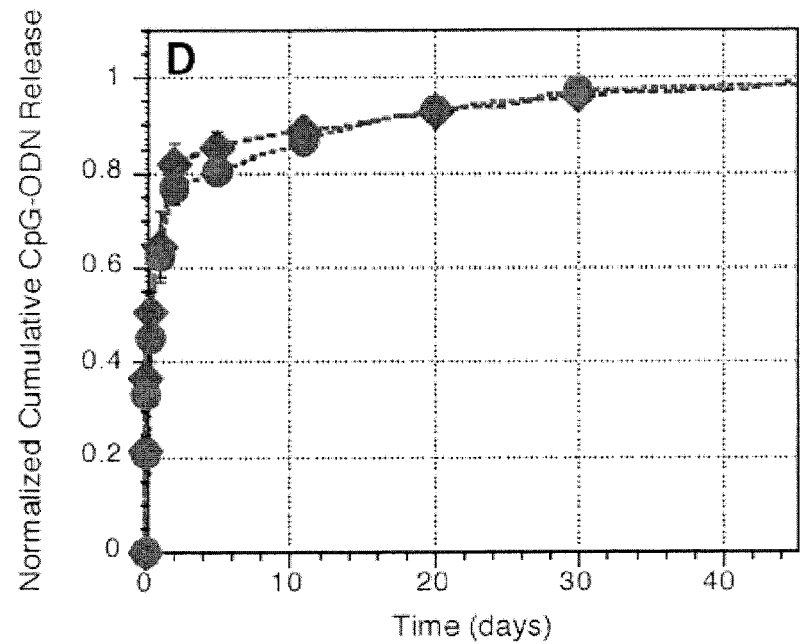

FIGS. 15A-D are a set of graphs showing the controlled release of biologically active immunomodulators from the cryogels. FIG. 15A is a bar graph showing the encapsulation efficiency of GM-CSF in alginate cryogels following polymerization, washing, and sterilization. FIG. 15B is a plot showing the release of GM-CSF for DC recruitment and programming. The cumulative release of GM-CSF from alginate cryogel matrices over a period of 6 weeks is shown. (diamond) 1.5 µg GM-CSF, (circle) 1.5 µg GM-CSF+50 µg CpG-ODN. FIG. 15C is a bar graph showing the encapsulation efficiency of CpG-ODN in alginate cryogels post polymerization, washing, and sterilization. FIG. 15D is a plot showing the release of CpG-ODN for DC activation. The cumulative release of CpG-ODN from alginate cryogel matrices over a period of 6 weeks is shown. (diamond) 50 μg CpG-ODN, (circle) 1.5 μg GM-CSF+50 μg CpG-ODN. Values represent mean and standard deviation (n=5). Differences between groups were statistically significant (* P<0.05, ** P<0.01).

FIGS. 16A-E are a set of photographs depicting representative swelling at the injection vaccination site. FIG. 16A is a set of two photographs showing a typical cryogel vaccine before (left) and after (right) seeding with irradiated B16-F10 cells. FIG. 16B is a photograph of mice, where group C mice were vaccinated with cryogel vaccines. Significant swelling was detected at day 13 only for vaccinated with cryogel vaccines (group C). FIG. 16C is a zoomed in photograph of a representative mouse from group C, with arrows pointing to sites of swelling. FIG. 16D is a close-up photograph of swelling in a mouse vaccinated with cryogel vaccines. FIG. 16E is another photograph of a representative mouse from group C with arrows pointing to sites of swelling.

Figure 17:
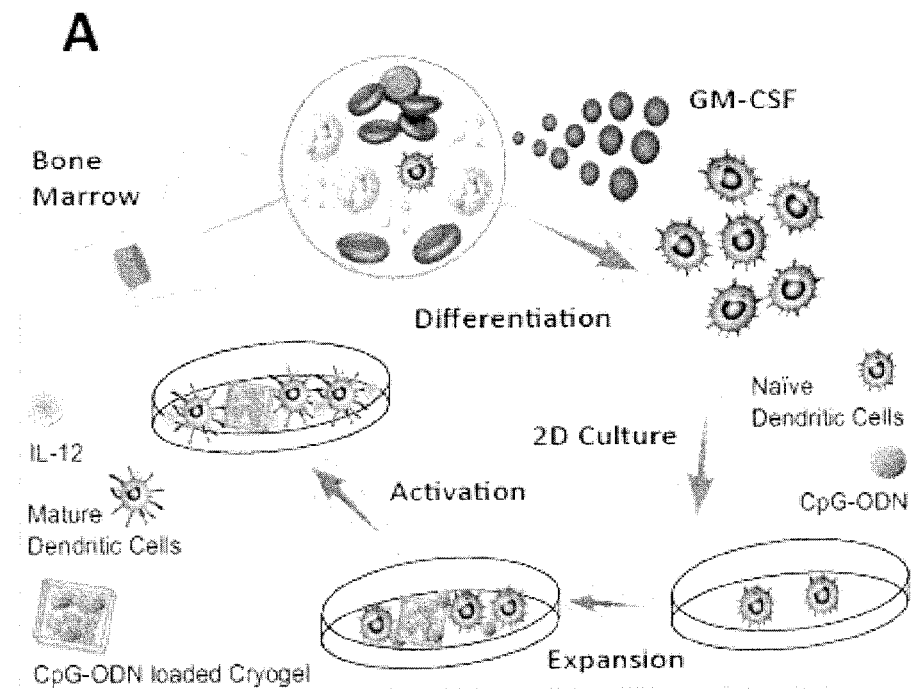
Figure 17:
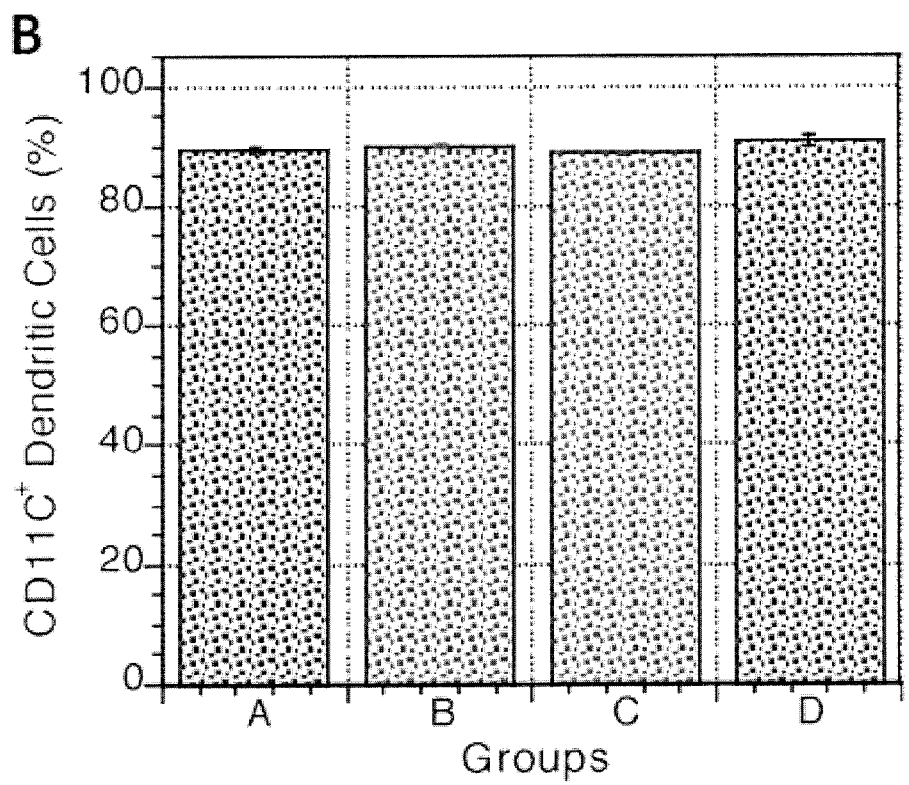
Figure 17:
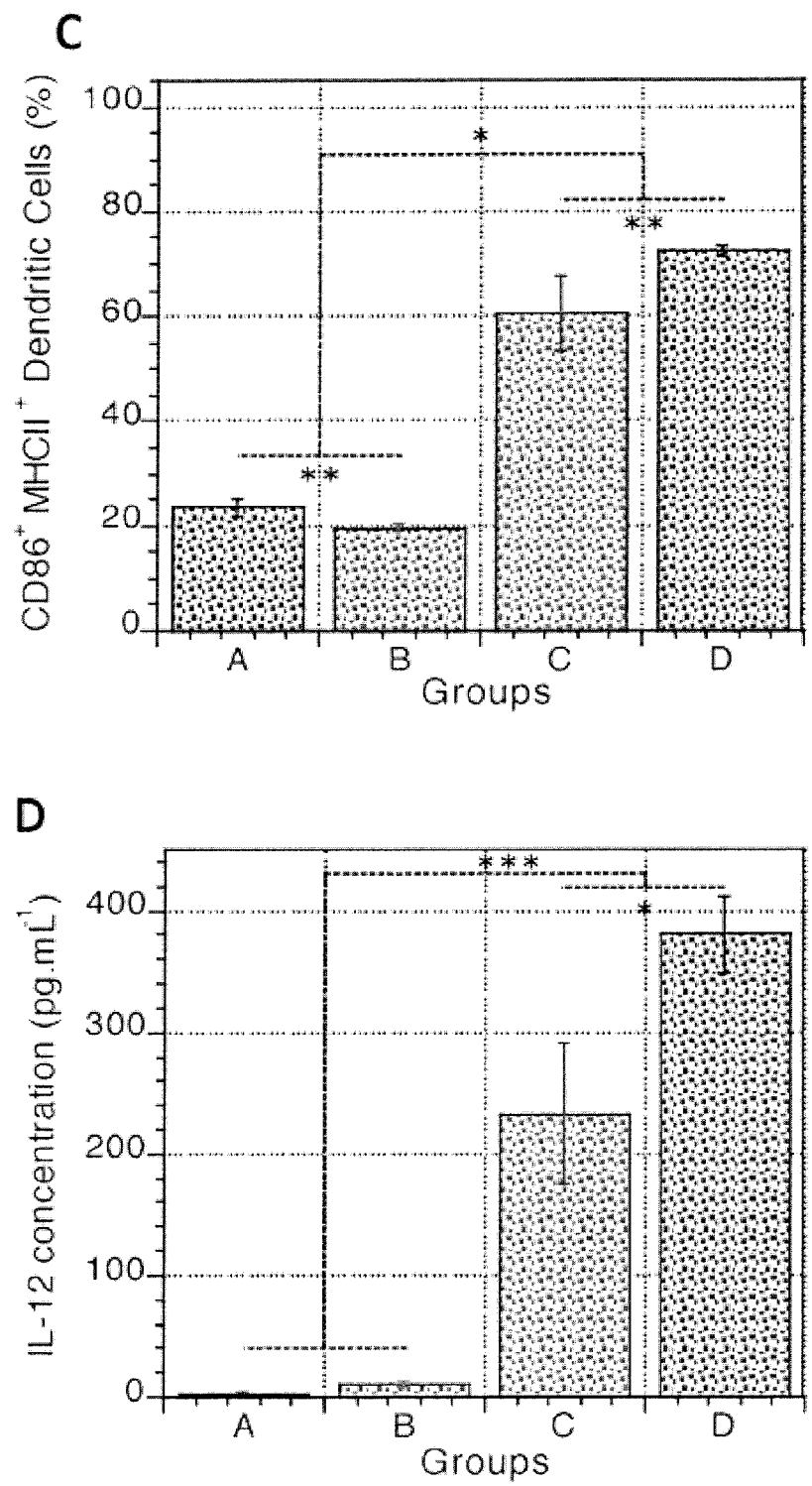

FIGS. 17A-D are a set of schematics and graphs showing the in vitro activation of differentiated bone marrow derived dendritic cells (BMDC) in response to CpG-ODN-loaded cryogels. BMDC were cultured for 24 h in contact with medium (group A, negative control), blank cryogels/medium (group B), CpG-ODN loaded cryogels/medium (group C), or CpG-ODN/medium (group D, positive control). FIG. 17A is a cartoon depicting the process of bone marrow isolation from murine tibias and femurs, differentiation, and expansion of BMDC to assess their activation in response of released CpG-ODN from cryogel vaccines. FIG. 17B is a bar graph showing the fraction of CD11C(+) BMDC used in each condition. FIG. 17C is a bar graph showing the fraction of activated CD86(+) MHCII(+) BMDC in each condition. FIG. 17D is a bar graph showing the production of IL-12 in culture media in response to DC stimulated by CpG-ODN in each condition. Values represent mean and standard deviation (n=5). Differences between groups were statistically significant (* P<0.05,  P<0.01, * P<0.001).

Figure 18:
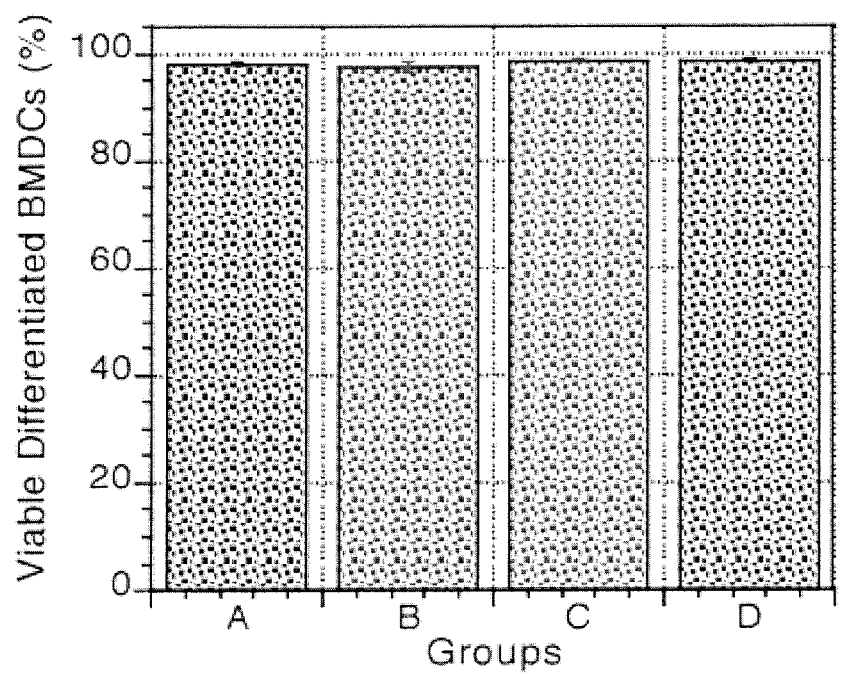

FIG. 18 is a bar graph showing the viability of differentiated BMDCs isolated from murine tibias and femurs used in each of four conditions tested (groups A-D). Differentiated bone marrow-derived dendritic cells (BMDCs) were cultured for 24 h in contact with medium (group A, negative control), blank cryogels/medium (group B), CpG-ODN loaded cryogels/medium (group C), or CpG-ODN/medium (group D, positive control).

Figure 19:
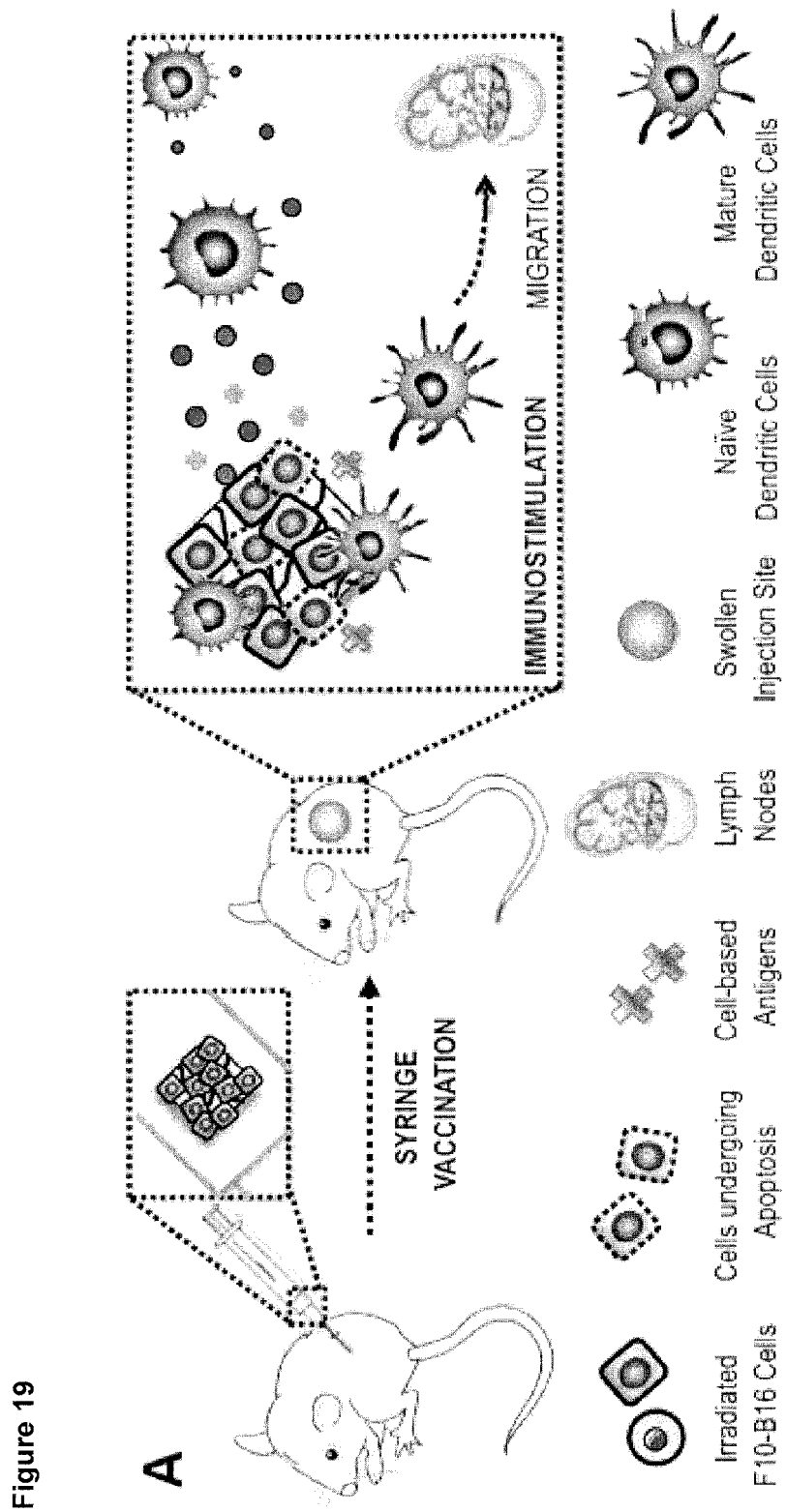
Figure 19:
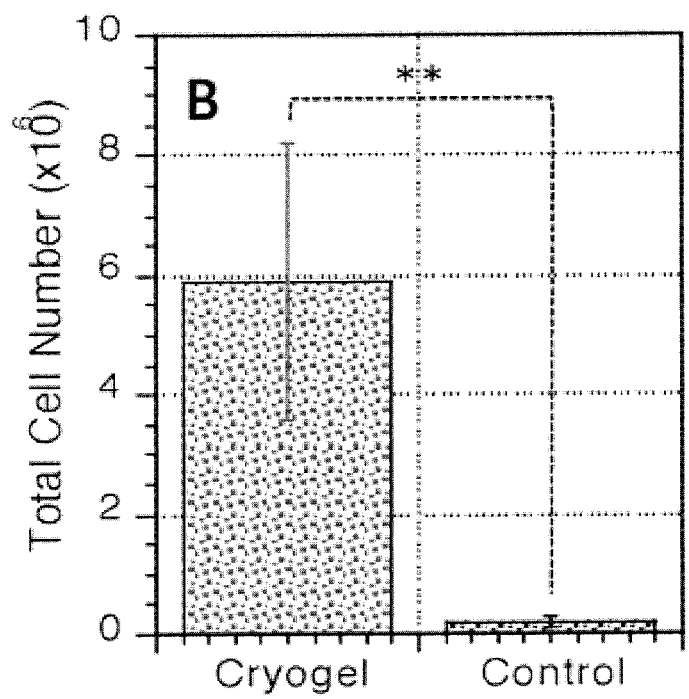
Figure 19:
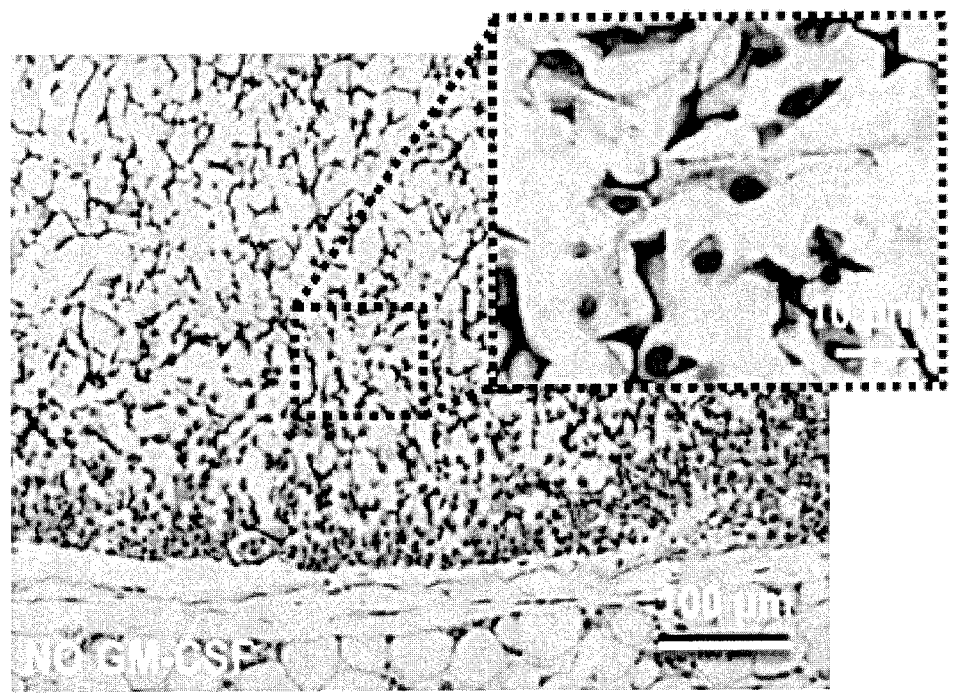
Figure 19:
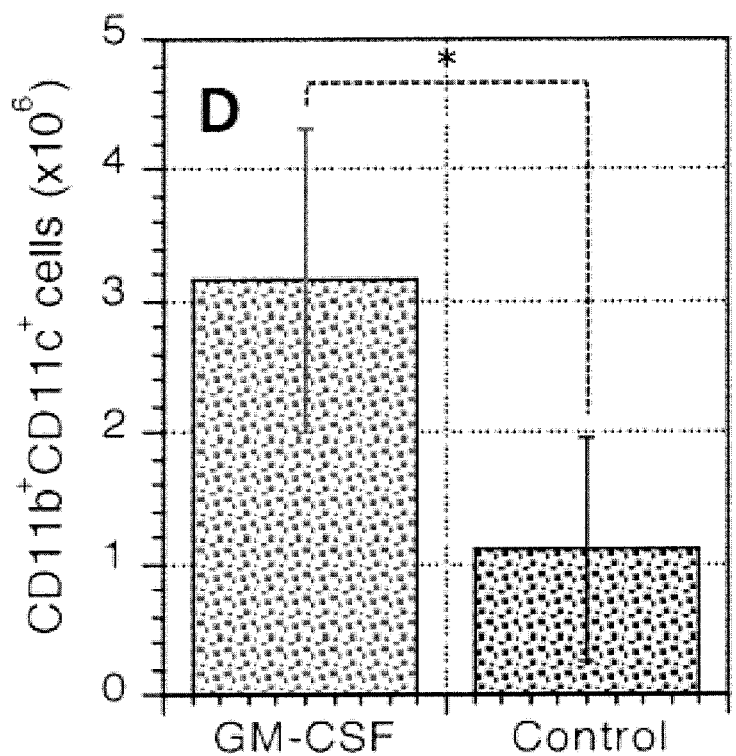
Figure 19:
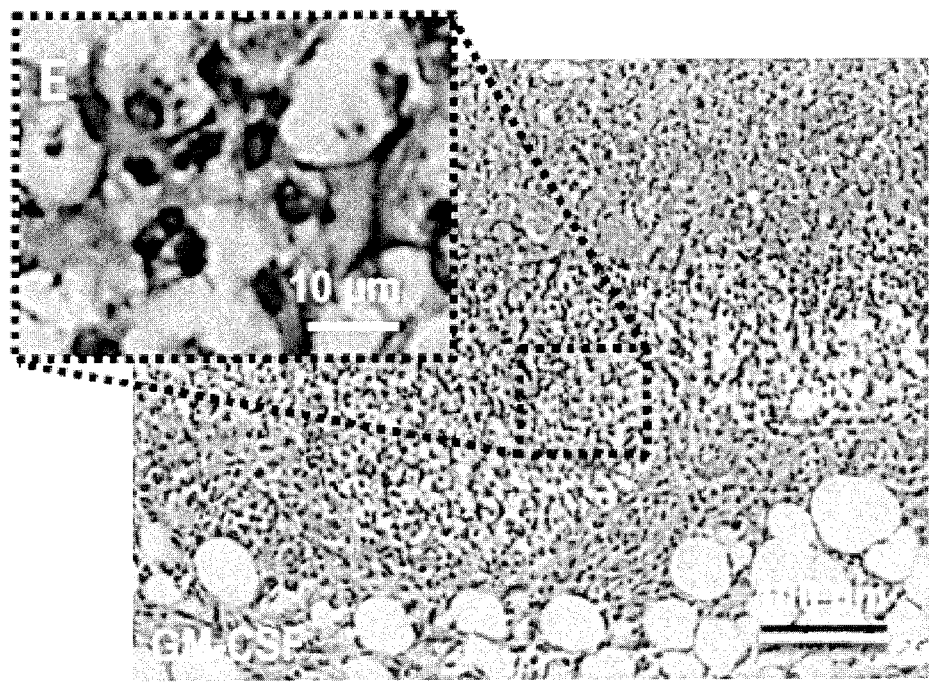

FIGS. 19A-E are a schematic, bar graphs, and images depicting that the cryogel vaccines promote cellular infiltration and leukocytes recruitment. FIG. 19A is a schematic representation displaying the subcutaneous injection of cryogel vaccines in mice using a standard gauge needle, as well as local edema and induration at the injection site and the recruitment and activation of naïve DC. FIG. 19B is a bar graph showing the enhancement of cellular infiltration in macroporous cryogel sponges versus conventional nanoporous hydrogels. The differences between the macroporous cryogel sponges of the invention and conventional nanoporous hydrogels arise from their methods of formation. The cryogels are formed when the solution is in a partially frozen state, while the conventional nanoporous gels are not—this results in formation of large interconnected pores in cryogels, versus nanometer scale pores in conventional gels. These differences in formation lead to differences in the mechanical properties of these gels, e.g., shape memory. FIG. 19D is a bar graph showing that GM-CSF delivery from cryogel sponge promotes CD11b(+)CD11c(+) DC recruitment to the cryogel sponges. FIGS. 19C and E are H&E stainings of sectioned cryogel scaffolds injected subcutaneously in the backs of C57BL/6J mice after 1 day: blank scaffolds (C) and GM-CSF (1.5 μg)-loaded scaffolds (E). Values represent mean and standard deviation (n=5). Differences between groups were statistically significant (* P<0.05, ** P<0.01).

Figure 20:
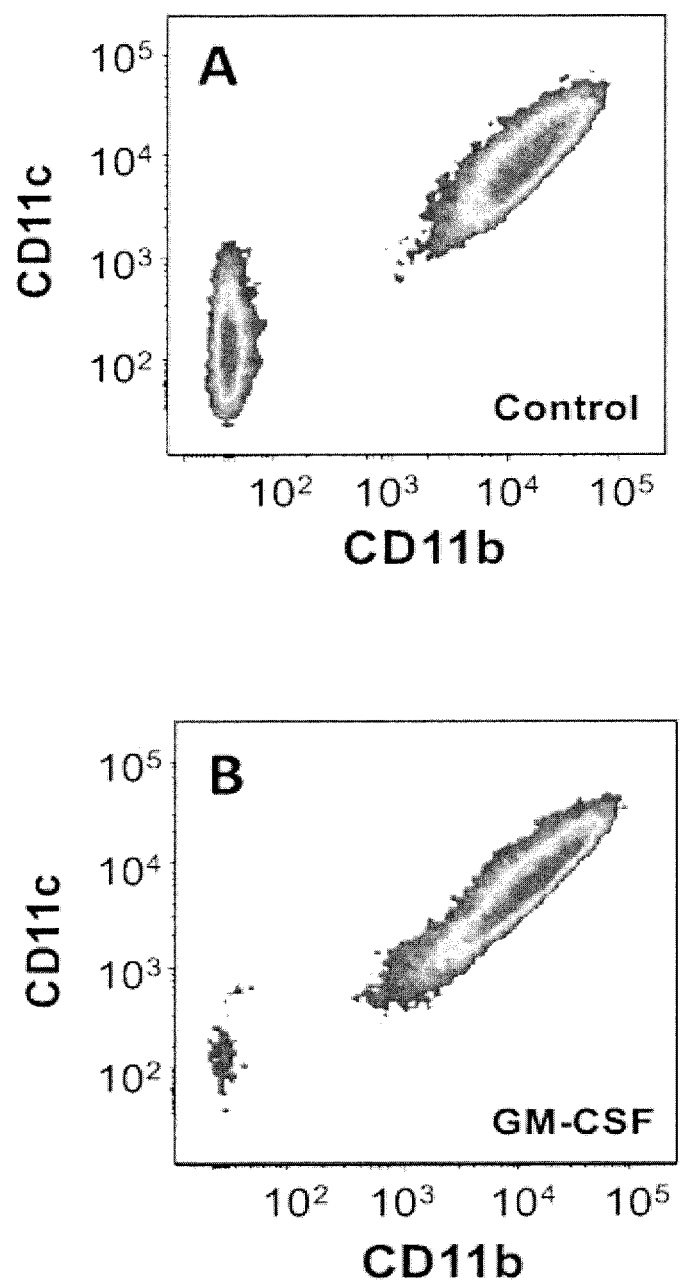

FIGS. 20A-B are a set of flow cytometry plots showing an enhanced recruitment of CD11b+ CD11c+ DC from GM-CSF loaded cryogels. Unlike blank cryogels (A, control), FACS analysis for CD11b+ CD11c+ DC showed that cryogel vaccines increased the fraction of infiltrated dendritic cells (B, GM-CSF loaded cryogel scaffolds).

Figure 21:
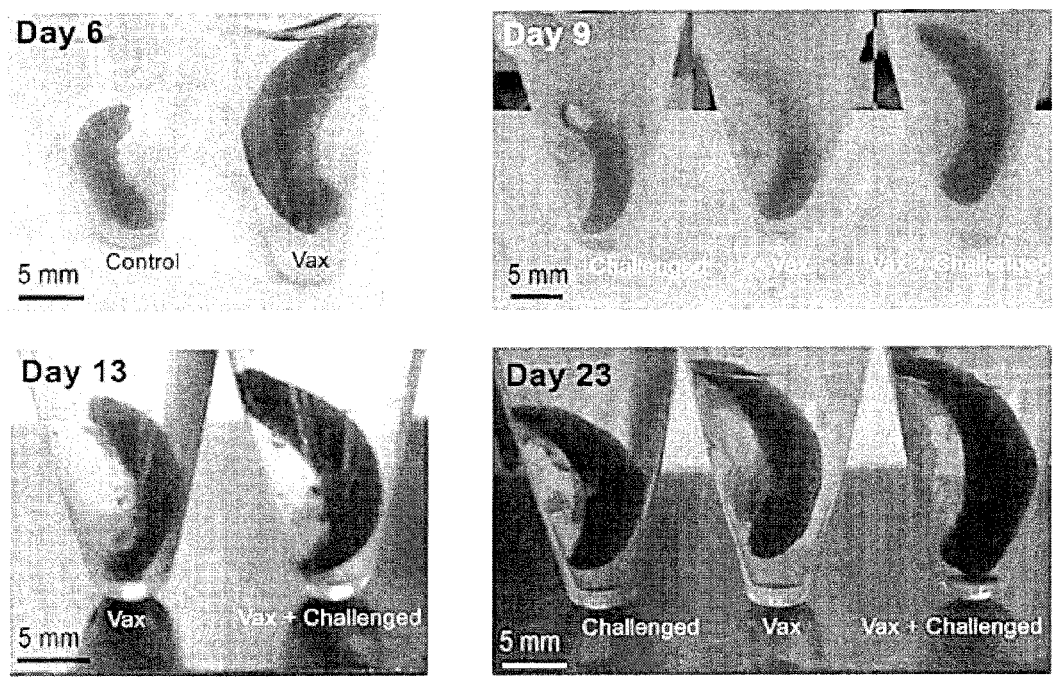

FIG. 21 is a set of four photographs showing the magnitude of the immune response elicited by the infection mimic-containing cryogel vaccines. In particular, the lymph nodes of vaccinated mice were markedly enlarged. Mice were vaccinated at day 0, and mice were euthanized and spleens explanted at different time points. Control (naïve mice), Challenged (naïve mice challenged at day 6), Vax (naïve mice vaccinated at day 0), Vax+Challenged (naïve mice vaccinated at day 0 and subsequently challenged at day 6).

Figure 22:
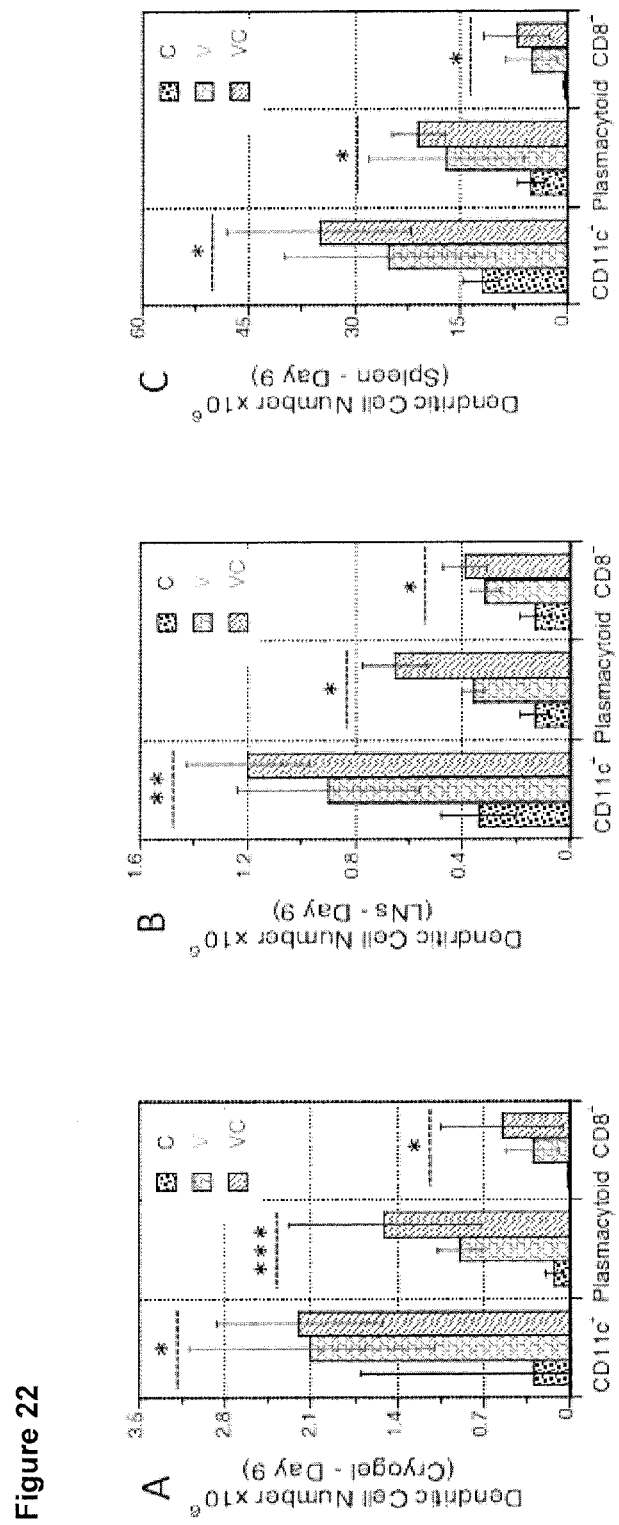
Figure 22:
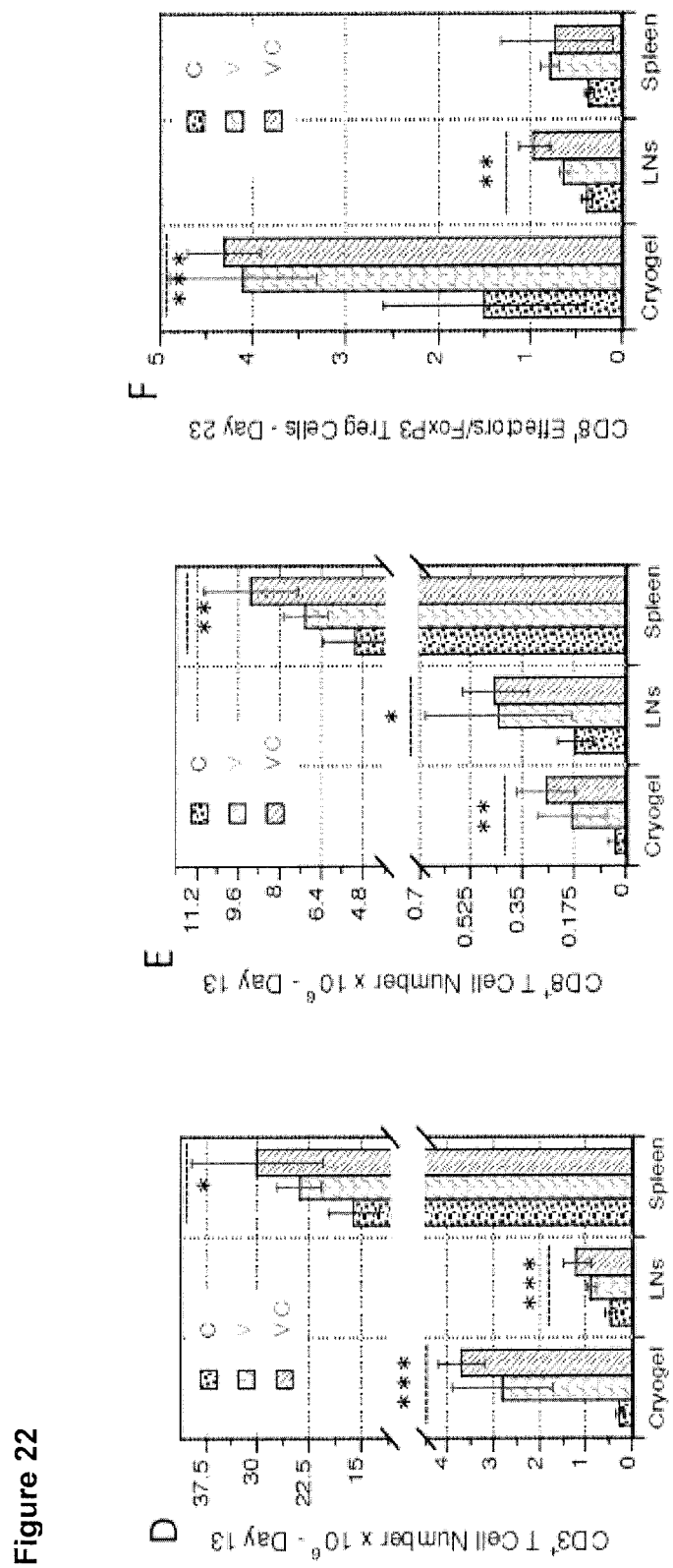
Figure 22:
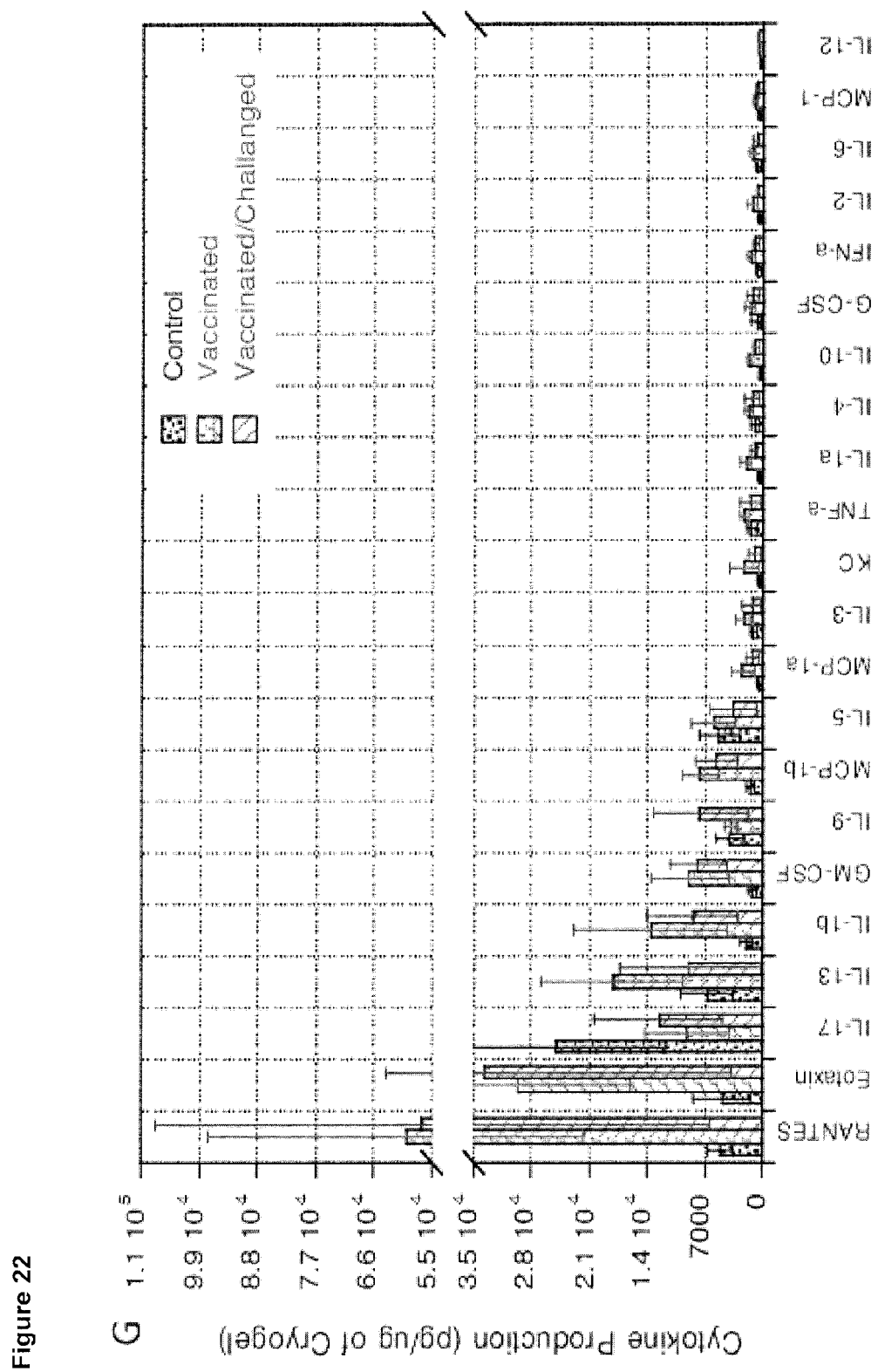

FIGS. 22A-G are a set a bar graphs showing that co-delivery of immunostimulatory factors (CpG-ODN and GM-CSF) from whole tumor cell-seeded cryogel vaccines stimulate recruitment and activation of DC, amplify CD8(+) cytotoxic T cells, and attenuate FoxP3(+) Treg cells. FIGS. 22A-C are bar graphs showing the numbers of CD11c(+), pDC, and CD8(+) at day 9 post-immunization isolated from explanted cryogel vaccines (FIG. 22A), LNs (FIG. 22B), and spleen (FIG. 22C). FIGS. 22D-E are bar graphs showing the numbers of CD3(+) T cells (FIG. 22D) and CD8(+) T cells (FIG. 22E) at day 13 post-immunization isolated from explanted cryogel vaccines, LNs, and spleen. FIG. 22F is a bar graph showing the ratio of CD8(+) T cells versus FoxP3(+) Treg cells residing within cryogel vaccines, LNs, and at day 23 after immunization. FIG. 22G is a bar graph showing the in vivo concentrations of mouse cytokines (IL-1α, IL-1β, IL-2, IL-3, IL-4, IL-5, IL-6, IL-9, IL-10, IL-12, IL-13, IL-17A, Eotaxin, G-CSF, GM-CSF, IFN-γ, KC, MCP-1, MCP-1α, MCP-1β, RANTES, TNF-α) from explanted cryogels at day 13. C, V, and VC groups correspond to mice injected with blank cryogels at day 0 (group C), mice immunized with cryogel vaccines at day 0 (group V), and mice immunized with cryogel vaccines at day 0+tumor challenged at day 6 (group VC), respectively. Values in FIGS. 22A, B, C, D, F, and G represent mean and SD (n=5). *P<0.05, P<0.01, *P<0.001 versus all other experimental conditions unless otherwise noted.

Figure 23:
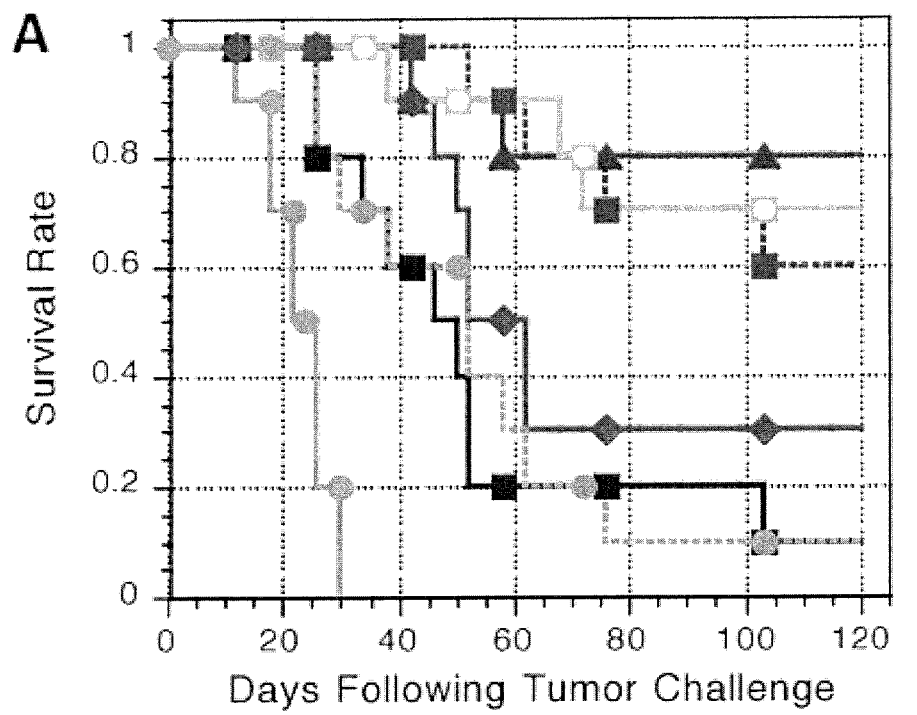
Figure 23:
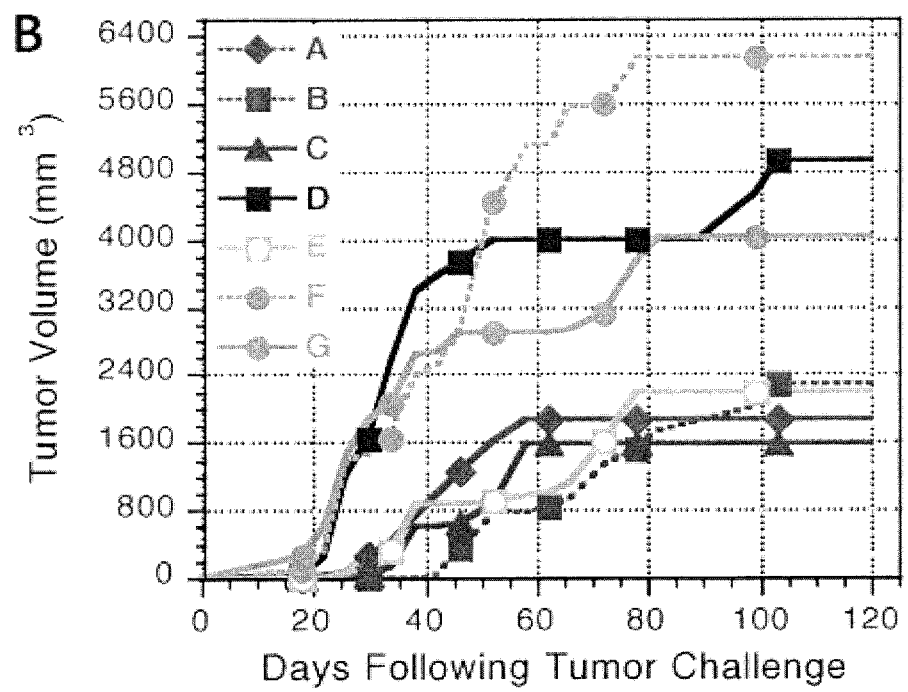
Figure 23:
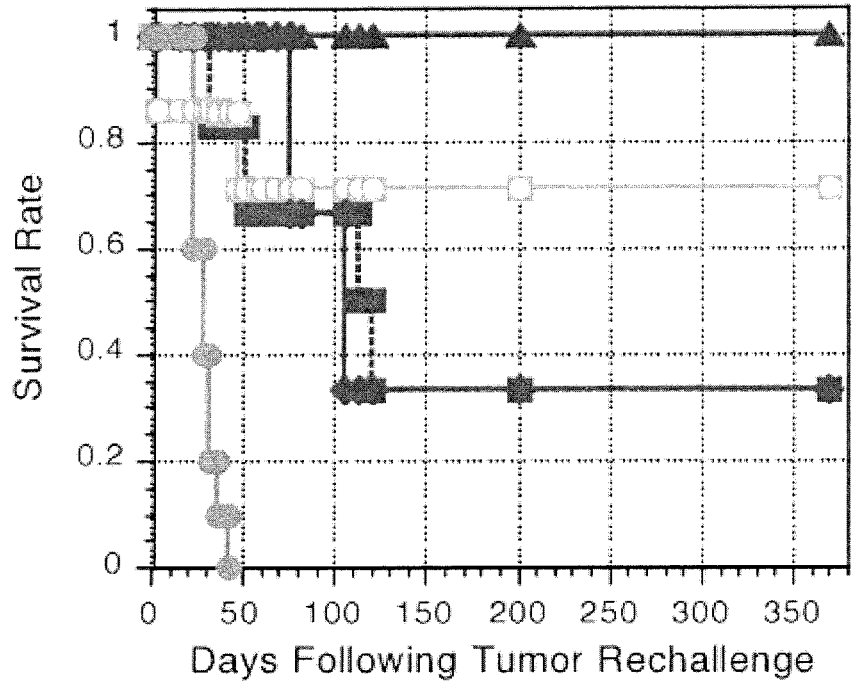
Figure 23:
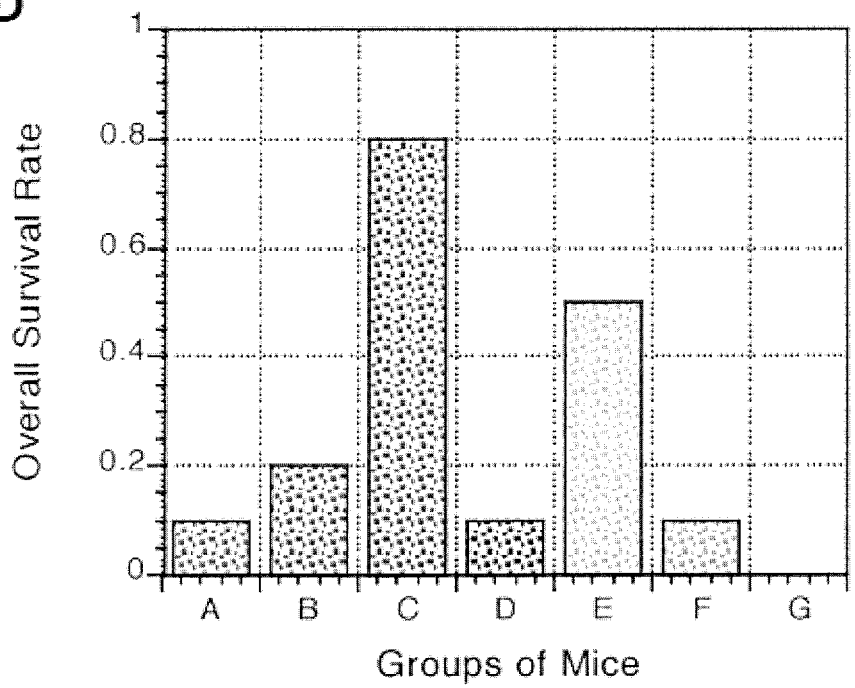

FIGS. 23A-D are a set of graphs showing the prophylactic efficacy of cryogel vaccines and long term protection against melanoma cancer. The infection-mimicking cryogel microenvironment confers potent anti-tumour immunity. FIG. 23A is a Kaplar meier plot showing the comparison of the survival rate in challenged C57BL/6 mice treated with (group A): Bolus G-Vax injection (irradiated GM-CSF secreting B16-F10 cells; positive control); (group B): Bolus injection (irradiated B16-F10 cells+CpG-ODN+GM-CSF); (group C): Cryogel vaccine (irradiated B16-F10 cells+CpG-ODN+GM-CSF; vaccine of interest); (group D): Cryogel vaccine (irradiated B16-F10 cells+GM-CSF); (group E): Cryogel vaccine (irradiated B16-F10 cells+CpG-ODN); (group F): Blank cryogel (control; negative control); or (group G): naïve mice (no immunization). At day 6 following immunization, C57BL/6J mice (10 mice/group) were challenged with 10$^5$ B16-F10 tumor cells and monitored for animal survival. FIG. 23B is a tumor growth curve after the 1st tumor challenge (5×10$^5$ cells) following one single cryogel vaccination 6 days prior to the challenge. FIG. 23C is a Kaplar meier plot showing a comparison of the survival rate in re-challenged mice treated with (group A): Bolus G-Vax injection (irradiated GM-CSF secreting B16-F10 cells; positive control); (group B): Bolus injection (irradiated B16-F10 cells+CpG-ODN+GM-CSF); (group C): Cryogel vaccine (irradiated B16-F10 cells+CpG-ODN+GM-CSF; vaccine of interest); (group D): Cryogel vaccine (irradiated B16-F10 cells+GM-CSF); (group E): Cryogel vaccine (irradiated B16-F10 cells+CpG-ODN); (group F): Blank cryogel (control; negative control); (group G): naïve mice (no immunization). At day 126 following immunization, C57BL/6J mice (10 mice/group) from the first challenge study were challenged a second time with 10$^5$ B16-F10 tumor cells and monitored for survival. FIG. 23D is a bar graph showing the overall survival rate after two consecutive tumor-challenges in mice to evaluate long-term immunological protection in the context of melanoma. Values represent mean and SD (n=10 per condition).

Figure 24:
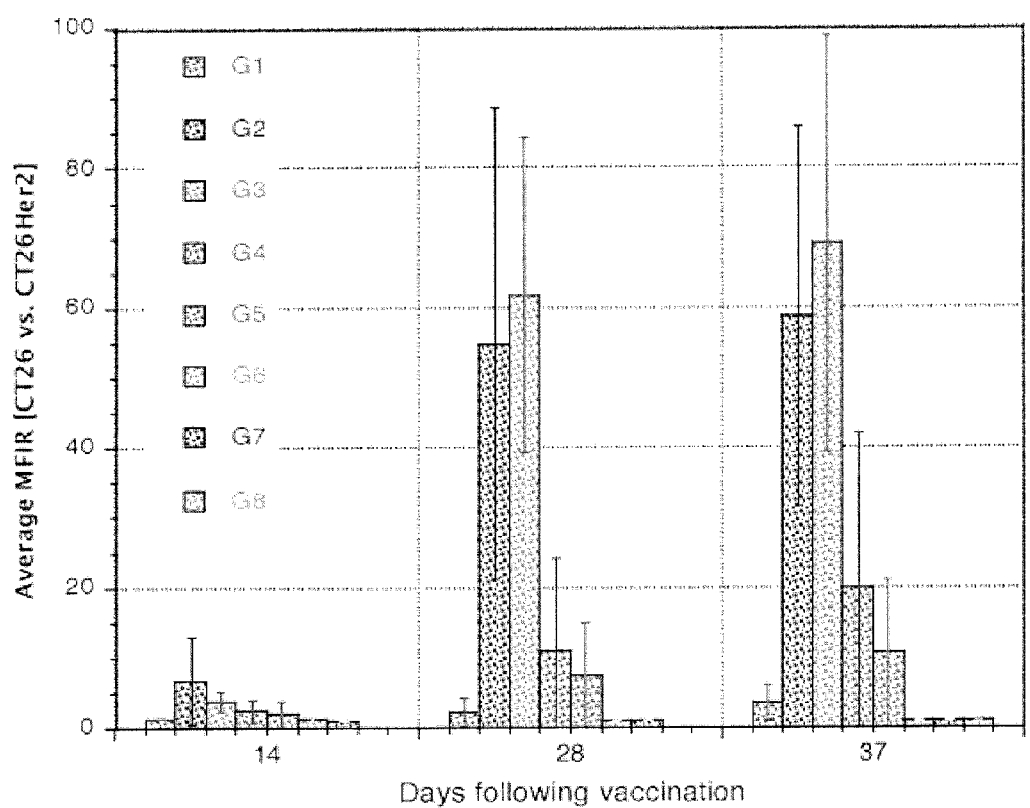

FIG. 24 is a bar graph showing that vaccination of mice with syringe-injectable cryogels elicits a strong humoral antitumor immune response against invasive HER-2/neu-overexpressing breast cancer cells. BALB/c mice (n=5) were immunized with (G1) cryogels (CpG-ODN+GM-CSF+breast tumor lysates); (G2) cryogels (CpG-ODN+attenuated GM-CSF secreting HER-2/neu-overexpressing breast cancer cells); (G3) cryogels (CpG-ODN+GM-CSF)+attenuated HER-2/neu-overexpressing breast cancer cells); (G4) CpG-ODN+attenuated GM-CSF secreting HER-2/neu-overexpressing breast cancer cells; (G5) attenuated GM-CSF secreting HER-2/neu-overexpressing breast cancer cells; (G6) blank cryogels; (G7) naïve mice; (G8) challenged naïve mice. At day 30 following immunization, the mice were challenged subcutaneously with 10$^5$ HER-2/neu-overexpressing breast tumor cells.

Figure 25:
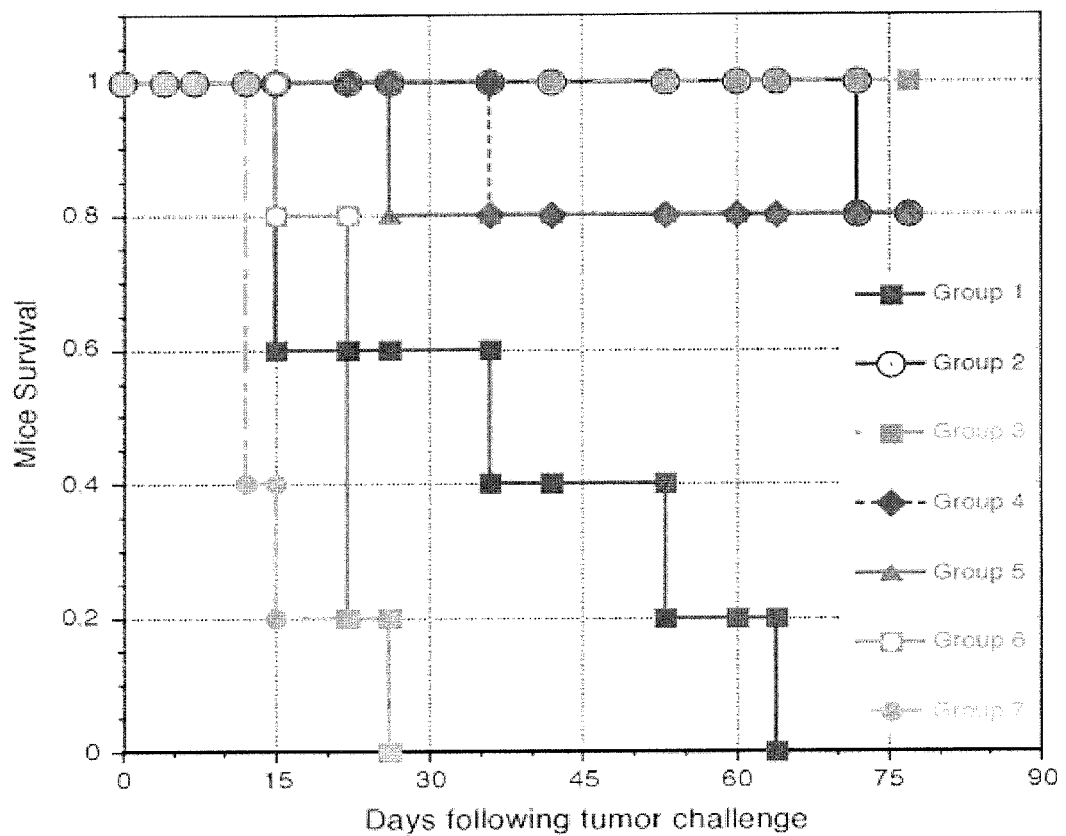

FIG. 25 is a Kaplar meier curve showing survival of mice immunized using HER-2/neu protein-specific vaccines. Autologous attenuated HER-2/neu-overexpressing breast cancer cell-based cryogel vaccine confers potent anti-tumour immunity. A comparison of the survival rate in challenged mice treated with (Group 1): Alginate-based cryogel vaccine (Lysates+CpG-ODN+GM-CSF); (Group 2): Alginate-based cryogel vaccine (GM-CSF secreting cells+CpG-ODN); (Group 3): Alginate-based cryogel vaccine (cells+CpG-ODN+GM-CSF; vaccine of interest); (Group 4): Bolus G-Vax injection (GM-CSF secreting cells; positive control); (Group 5): Bolus injection (GM-CSF secreting cells+CpG); (Group 6): Blank alginate-based cryogel (control; negative control); (Groups G, and E): naïve mice (no immunization). At day 30 following immunization, BALB/c mice (5 mice/group) were challenged with 10$^5$ HER-2/neu-overexpressing breast tumor cells and monitored for animal survival.

Figure 26:
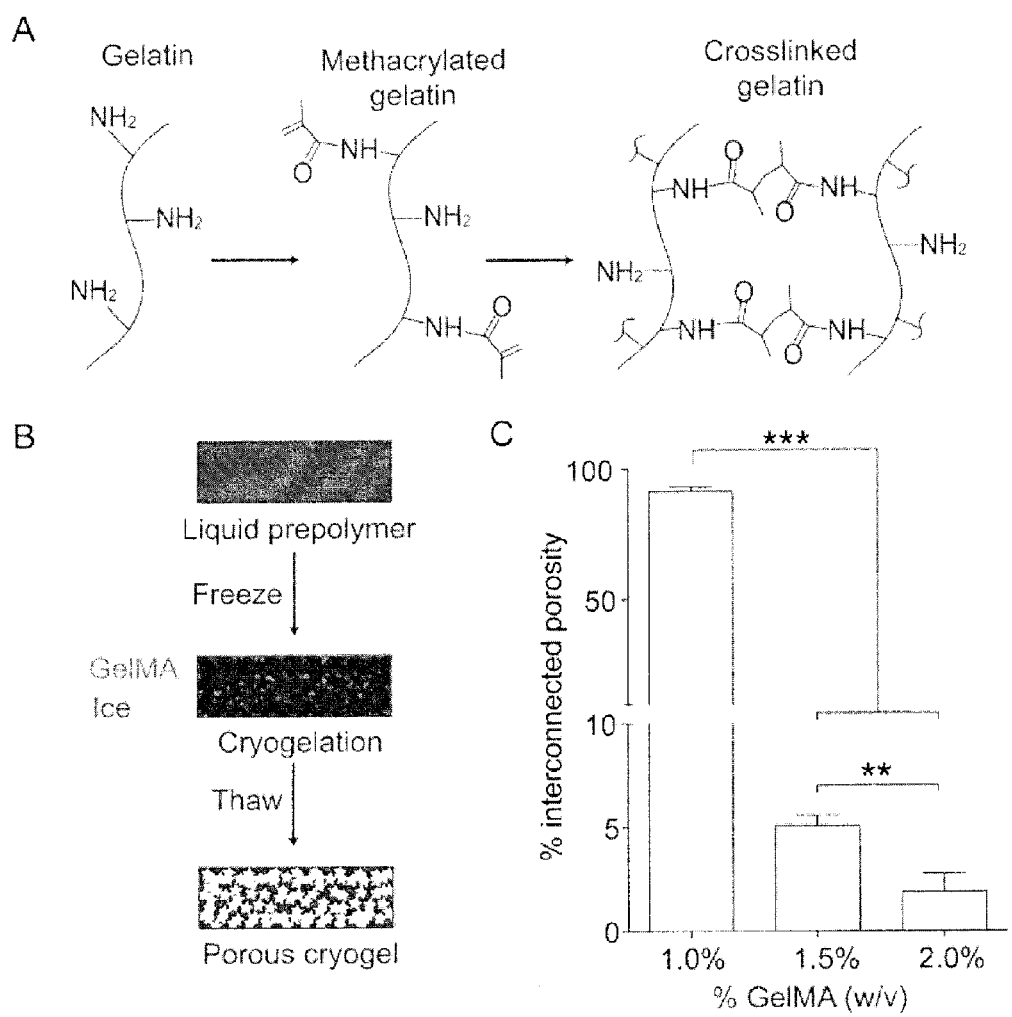

FIGS. 26A-C depict the fabrication of gelatin cryogels with highly interconnected pores. FIG. 26A is a schematic of methacrylated gelatin (GelMA) synthesis and crosslinking. Pendant methacrylate groups are added primarily to the free amines of gelatin by reaction with methacrylic anhydride. Free radical polymerization results in crosslink formation between methacrylate groups. FIG. 26B is a schematic showing cryopolymerization of methacrylated gelatin. Freezing of methacrylated gelatin in the presence of radical initiators (ammonium persulfate (APS) and N,N,N',N'-tetramethylethylenediamine (TEMED)) allows polymerization to occur in the partially frozen state (cryopolymerization). Ice crystals formed during the freezing process and thawing after cryopolymerization results in the formation of a hydrogel with micron-scale pores. FIG. 26C is a graph showing the % interconnected porosity of the gelatin cryogel when various concentrations of GelMA are used. Volume of interconnected pores in gelatin cryogels (normalized to total gel volume). Values represent mean and standard deviation (n=10). Data were compared using Analysis of variance (ANOVA) with Bonferroni's post-hoc test (p<0.01, *p<0.001).

Figure 27:
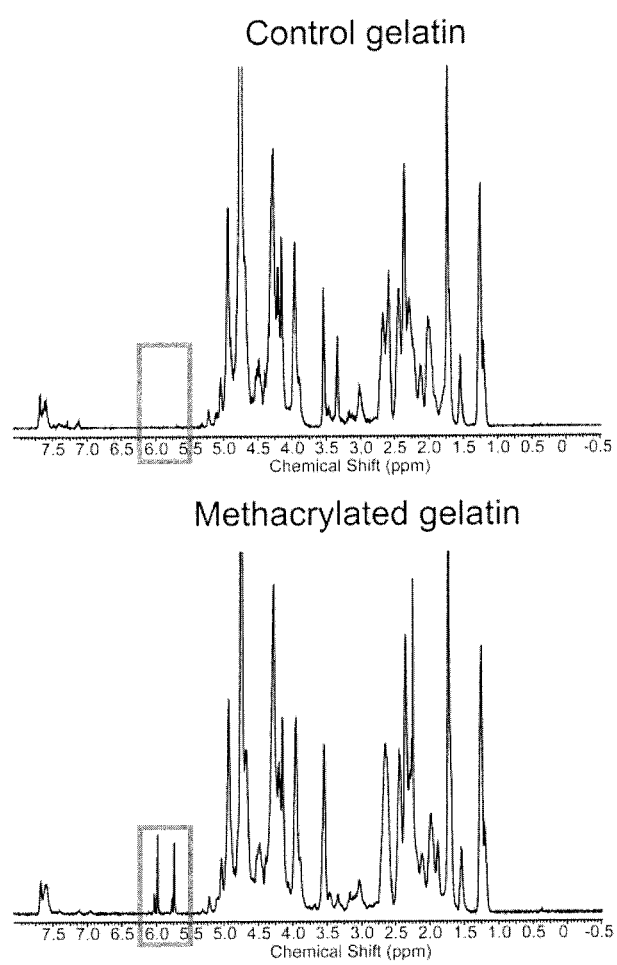

FIG. 27 is a pair of nuclear magnetic resonance (NMR) spectra comparing control gelatin (top) and methacrylate modified gelatin (bottom). $^1$H-NMR spectra of unmodified (top) and methacrylated (bottom) gelatin shows the appearance of the vinylene protons (red box) of the methacrylate pendant group after reaction of gelatin with methacrylic anhydride.

Figure 28:
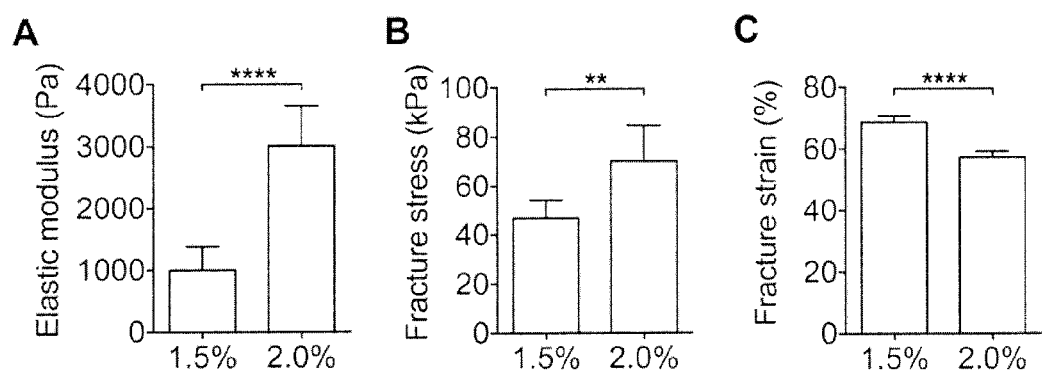

FIGS. 28A-C depict mechanical properties of gelatin cryogels. Hydrated 1.5% and 2% cryogels were tested in compression at 1 mm/min. The resulting stress-strain curves were used to calculate the (A) elastic modulus, (B) fracture stress, and (C) fracture strain. FIG. 28A is a graph depicting the elastic modulus. FIG. 28B is a graph depicting the fracture stress. FIG. 28C is a graph depicting the % fracture strain. Error bars represent the standard deviation from measurements of 10 gels tested per condition. Data were compared using a two-tailed unpaired Student's t-test with Welch's correction (p<0.01, **p<0.0001). The mechanical properties of 1.0% cryogels could not be measured using compressive mechanical testing.

Figure 29:
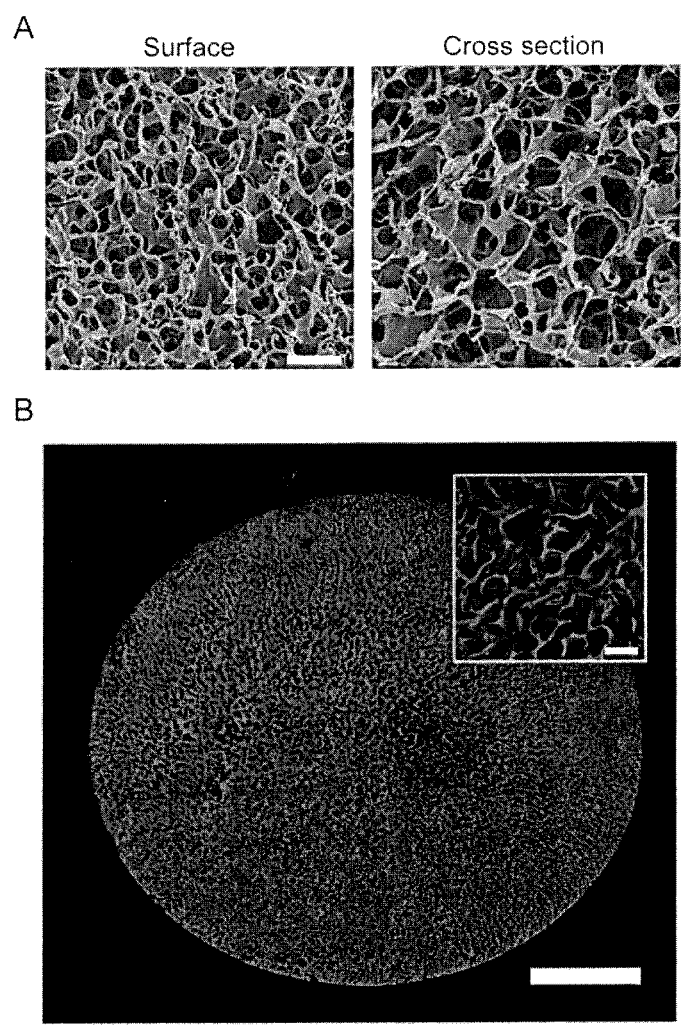

FIGS. 29A-B are a series of images showing the microarchitecture of gelatin cryogels. FIG. 29A is a set of images showing the surface and cross-sectional scanning electron microscopy (SEM) micrographs of highly porous 1.0% (w/v) gelatin cryogels (scale bar=50 μm). FIG. 29B is an image using 2-photon imaging at a depth of 150 μm below the surface of a rhodamine-gelatin cryogel (scale bar=1 mm) The inset shows a magnified view at the center of the scaffold diameter (scale bar=100 μm). Images are representative of at least 5 gels imaged using each modality.

Figure 30:
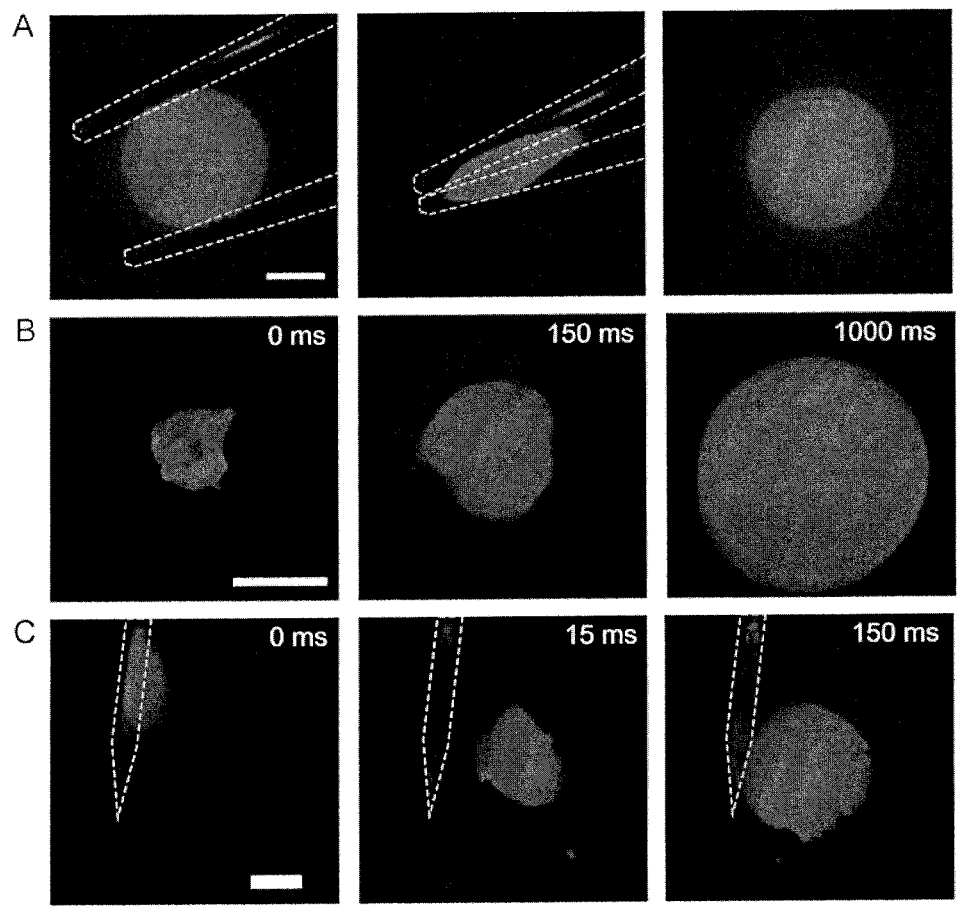

FIGS. 30A-C are a series of images depicting bulk mechanical behavior and injectability of gelatin cryogels. FIG. 30A is a panel of images demonstrating the ability of an individual rhodamine-gelatin cryogel to be compressed between forceps (dashed white line) to large strain, followed by release and resumption of its original shape. FIG. 30B is a panel of images showing Rhodamine-gelatin cryogel following collapse due to wicking of free water (0 ms), and rapid rehydration following exposure to excess DPBS. FIG. 30C is a panel of images showing Rhodamine-gelatin cryogel exiting the bore of a 16 G needle (0 ms, outer needle wall outlined with dashed line), and its expansion to original size and shape after injection. All scale bars=2 mm.

Figure 31:
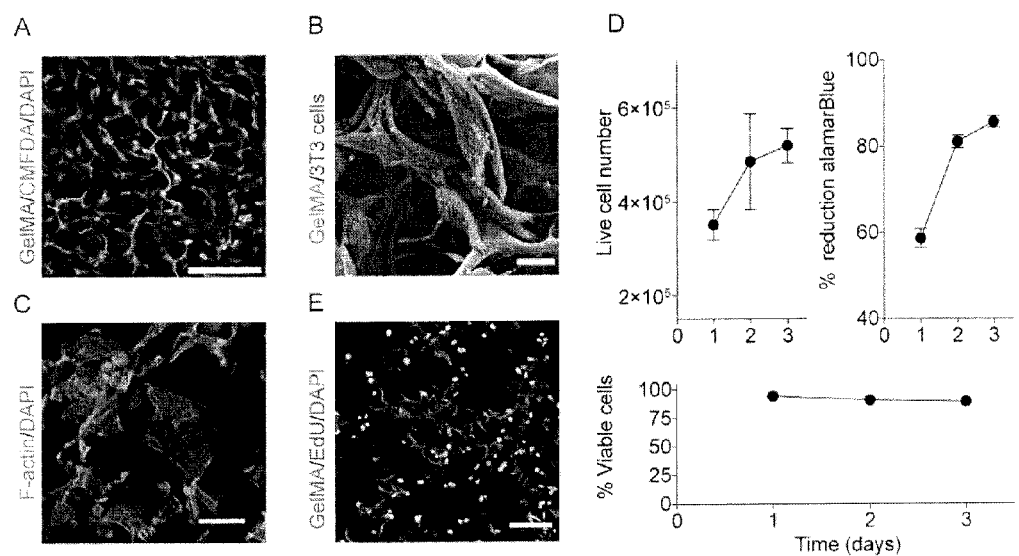

FIGS. 31A-E depict cell attachment, survival, and proliferation on gelatin cryogels in vitro. FIG. 31A is a representative 2-photon microscopy image of 5-Chloromethylfluorescein Diacetate (CMFDA)-labeled cells at 150 μm depth below the surface of a rhodamine-gelatin cryogel 2 h after seeding (n=5, scale bar=200 μm). FIG. 31B is a SEM micrograph of 3T3 cells spread on cryogel surface at 1 d post-seeding (n=5, scale bar=10 μm). Cells are false-colored for emphasis. FIG. 31C is a staining of F-actin on histological sections showing cell spreading within scaffolds after one day of culture (n=3, scale bar=25 μm). FIG. 31D is a graph showing an analysis of the number of live cells, overall metabolic activity as measured by alamarBlue reduction, and viability of cells recovered from gelatin cryogels over time in culture. Values represent the mean and standard deviation (n=3). FIG. 31E is a staining for new DNA synthesis within the scaffold using 5-ethynyl-2'-deoxyuridine (EdU) incorporation (n=3, scale bar=100 μm).

Figure 32:
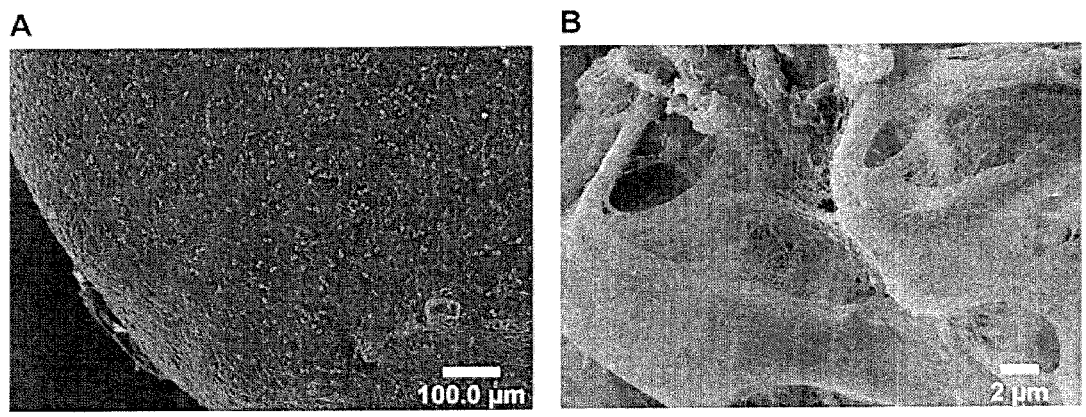

FIGS. 32A-B are a set of SEM images of cryoGelMA gels three days after 3T3 cell seeding. FIG. 32A is a SEM image showing a monolayer of 3T3 cells after three days of culture on cryoGelMA. FIG. 32B is a SEM image showing extracellular matrix deposition on the cryoGelMA surface seen after mechanically disrupting the cell monolayer.

Figure 33:
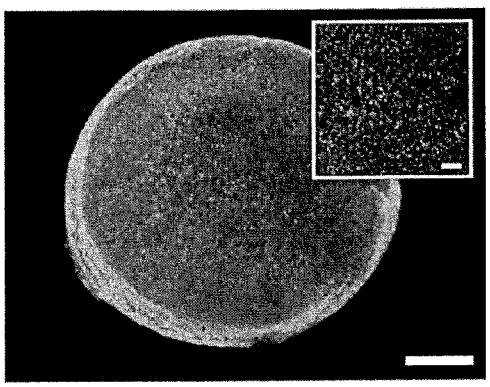
Figure 33:
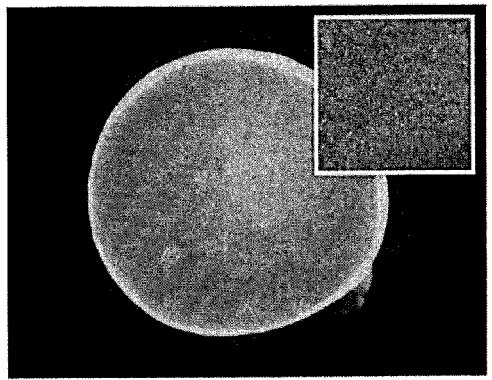

FIGS. 33A-B are live dead imaging of 3T3 cells following seeding on gelatin cryogels. Gelatin cryogels were labeled with a Live/Dead staining kit (green=live, red=dead) to assess viability. FIG. 33A is a bulk image at 1 day after seeding. FIG. 33B is a bulk images at 3 days after seeding. Magnified image of the cellular coverage of the cryogel surface over the culture period (insets). Scale bar=1 mm, inset scale bar=200 μm.

Figure 34:
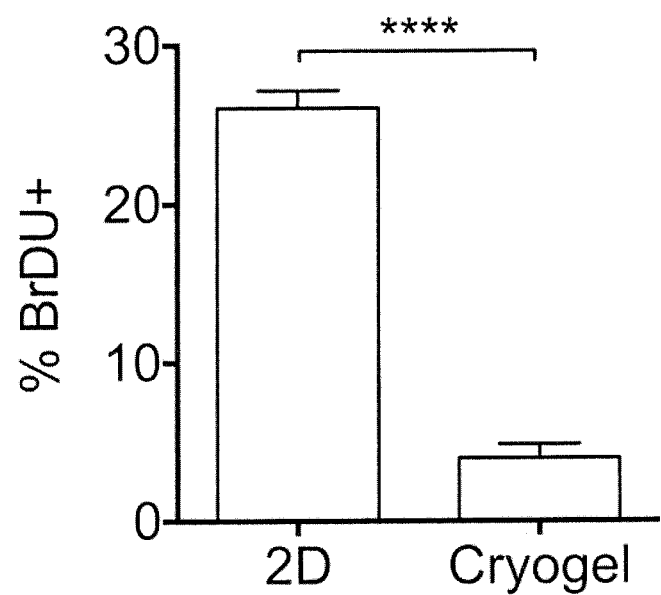

FIG. 34 is a graph showing bromodeoxyuridine (BrDU) incorporation into 3T3 cells. 3T3 cells seeded on tissue culture polystyrene (~50% confluency) and for one day on cryoGelMA (n=3) were pulsed with 30 μm BrDU for 4 h and analyzed by flow cytometry for BrDU incorporation. Values represent percentage of total cells that exhibited positive BrDU staining. Data were compared using a two-tailed unpaired Student's t-test with Welch's correction (***$p<0.001$).

Figure 35:
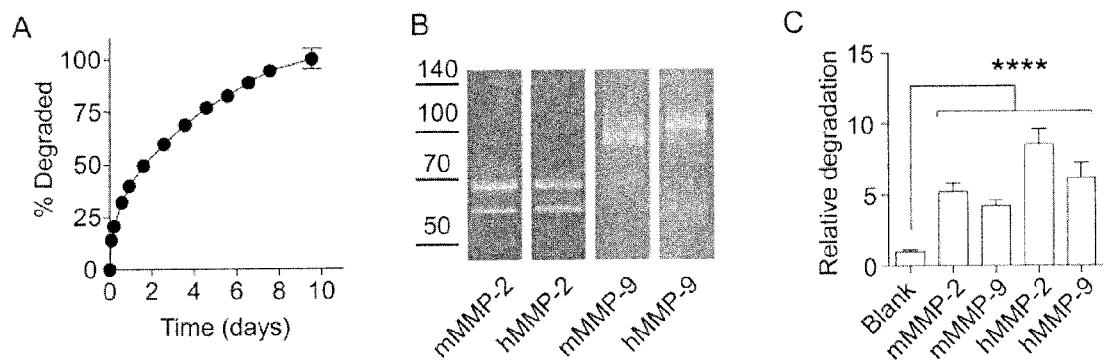

FIGS. 35A-C depict enzymatic degradation of gelatin cryogels in vitro. FIG. 35A is a graph showing in vitro degradation of rhodamine-gelatin cryogels (n=3) in the presence of 25 U/ml collagenase type II. FIG. 35B shows Zymography with mouse and human pro-MMP-2 and pro-MMP-9 using GelMA-polyacrylamide gels. FIG. 35C is a graph showing the quantification of degradation of rhodamine-gelatin cryogels (n=4) in the presence of 10 μg/ml recombinant mouse and human MMP-2 and -9 for 18 hours. One-way ANOVA with Dunnett's test was performed to compare all MMP-treated conditions with the control gels incubated in buffer alone (n=4, ****$p<0.0001$). Values represent the mean and standard deviation in all plots.

Figure 36:
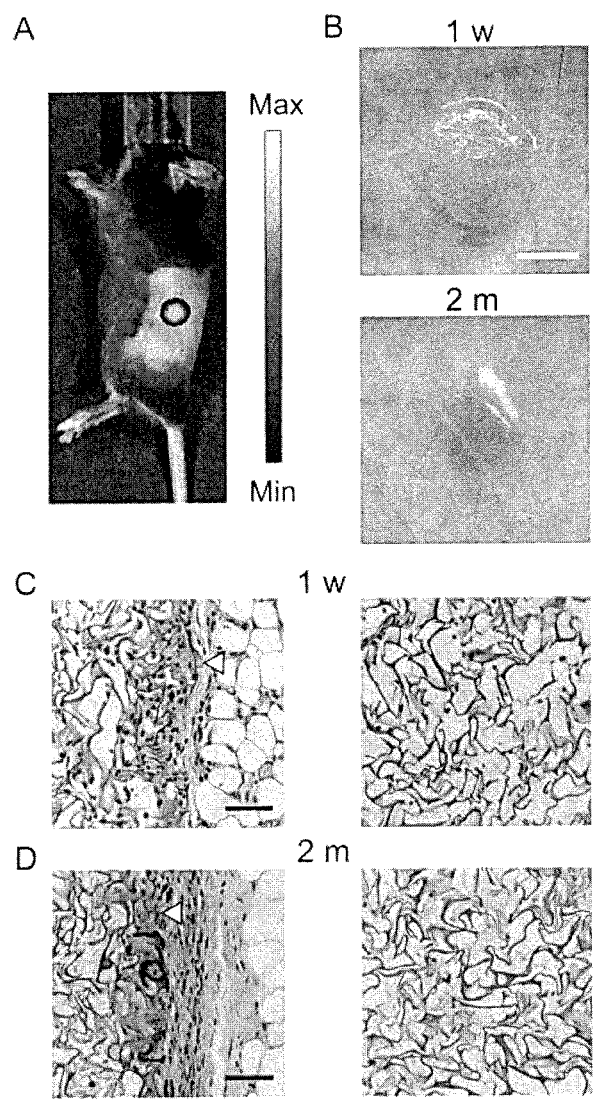

FIGS. 36A-D are a set of images depicting in vivo injection of gelatin cryogels. FIG. 36A is an in vivo fluorescence image of rhodamine-gelatin cryogel in a C57Bl/6J mouse immediately following subcutaneous injection. FIG. 36B is an in situ image of rhodamine-gelatin cryogel under the skin at 1 w and 2 m following implant. FIG. 36C is an Hematoxylin and eosin (H&E) stain at 1 w following implant at the cryogel-tissue interface (left) and the cryogel interior (right) (n=3, scale bar=50 μm). Arrows indicate the cryogel-host border. FIG. 36D is an H&E stain at 2 m following implant at the cryogel-tissue interface (left) and the cryogel interior (right) (n=3, scale bar=50 μm). Arrows indicate the cryogel-host border.

Figure 37:
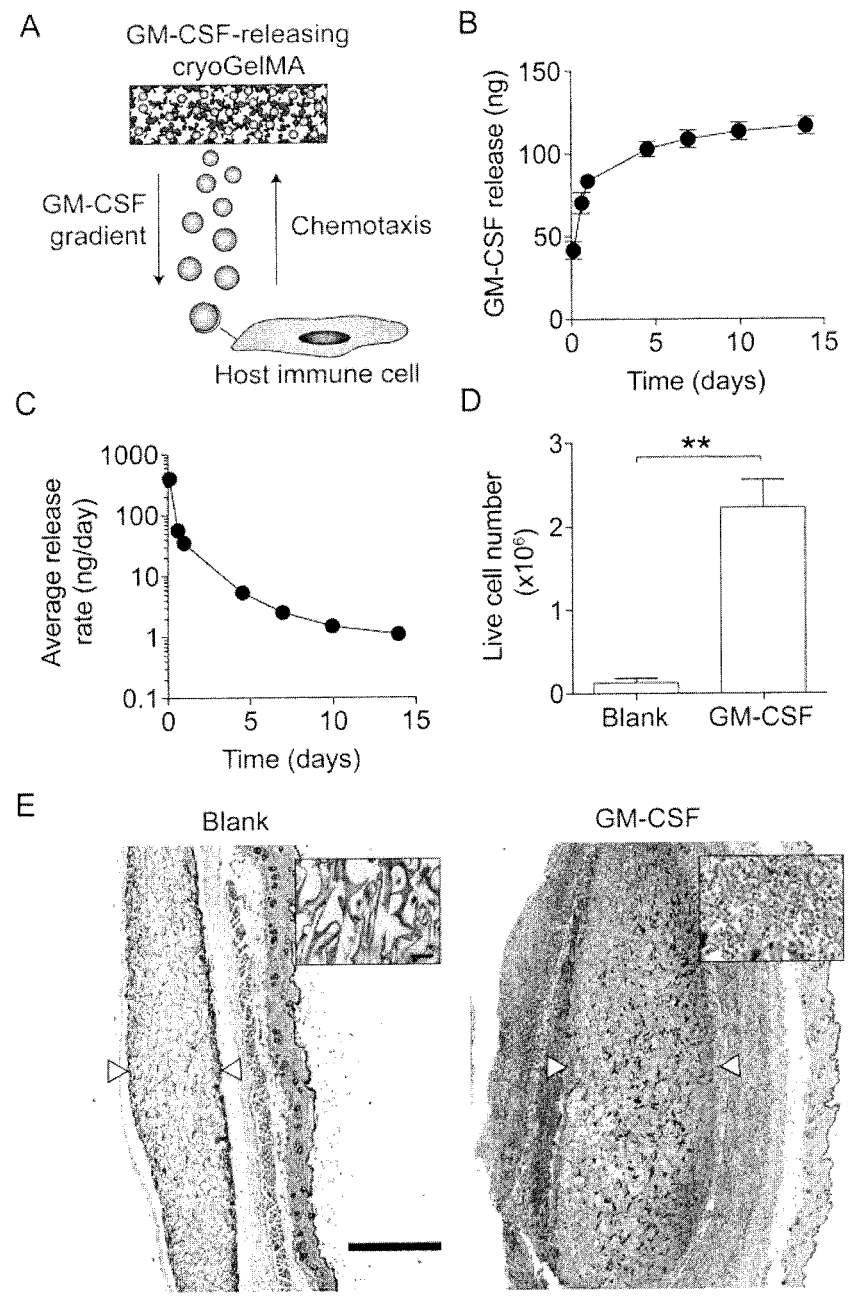

FIG. 37A-E depicts in vivo cell recruitment to gelatin cryogels by sustained release of GM-CSF. FIG. 37A is a schematic of cell recruitment to GM-CSF-releasing gelatin cryogels. Sustained release of GM-CSF from the cryogel implant creates a chemoattractant gradient to attract host immune cells. FIG. 37B is a graph showing in vitro cumulative GM-CSF release from gelatin cryogels. FIG. 37C is a graph showing the average release rate of GM-CSF from gelatin cryogels. FIG. 37D is a graph showing recruited cell numbers in blank and GM-CSF-releasing gelatin cryogels at 14 d post-implant (Student's t-test, n=3 mice, **$p<0.01$). FIG. 37E is a set of representative H&E stainings from blank and GM-CSF-releasing cryogels 14 d after implantation in C57/B16J mice (n=3, scale bar=500 μm). Inset shows a magnified view of the scaffold interior (scale bar=20 μm). Arrows indicate the cryogel-tissue borders. Values represent the mean and standard deviation in all plots.

Figure 38:
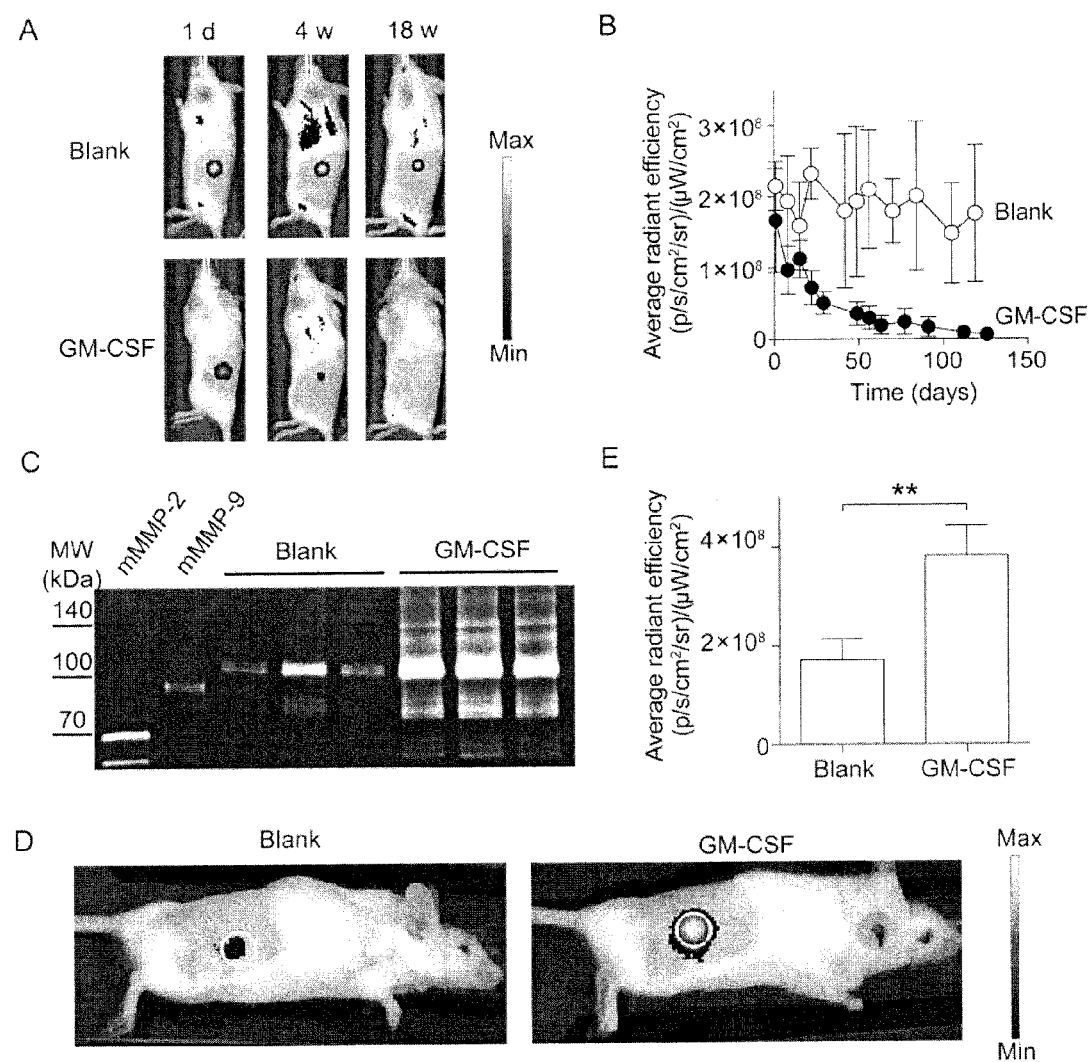

FIGS. 38A-E depict gelatin cryogel degradation by recruited cells in vivo. FIG. 38A is a set of images from longitudinal in vivo imaging of the degradation of blank and GM-CSF-releasing rhodamine-gelatin cryogels in C57Bl/6J-Tyr$^{c-2J}$ mice (n=5). FIG. 38B is a graph showing the quantification of fluorescence signal from longitudinal in vivo imaging of the degradation of blank and GM-CSF-releasing rhodamine-gelatin cryogels in C57Bl/6J-Tyr$^{c-2J}$ mice (n=5). FIG. 38C is an image showing gelatin zymography of cellular lysates from 1 w implanted blank and GM-CSF-releasing rhodamine-gelatin cryogels (n=3). FIG. 38D is a representative in vivo fluorescence image of MMPSense 750 FAST activation in mice 7 d following injection in opposite flanks with blank and GM-CSF-releasing rhodamine-gelatin cryogels. Scaffold borders are outlined in white. FIG. 38E is a graph depicting quantitation (paired t-test, n=3, **$p<0.01$) of MMPSense 750 FAST activation in mice 7 d following injection in opposite flanks with blank and GM-CSF-releasing rhodamine-gelatin cryogels. Scaffold borders are outlined in white. Values represent the mean and standard deviation in all plots.

Figure 39:
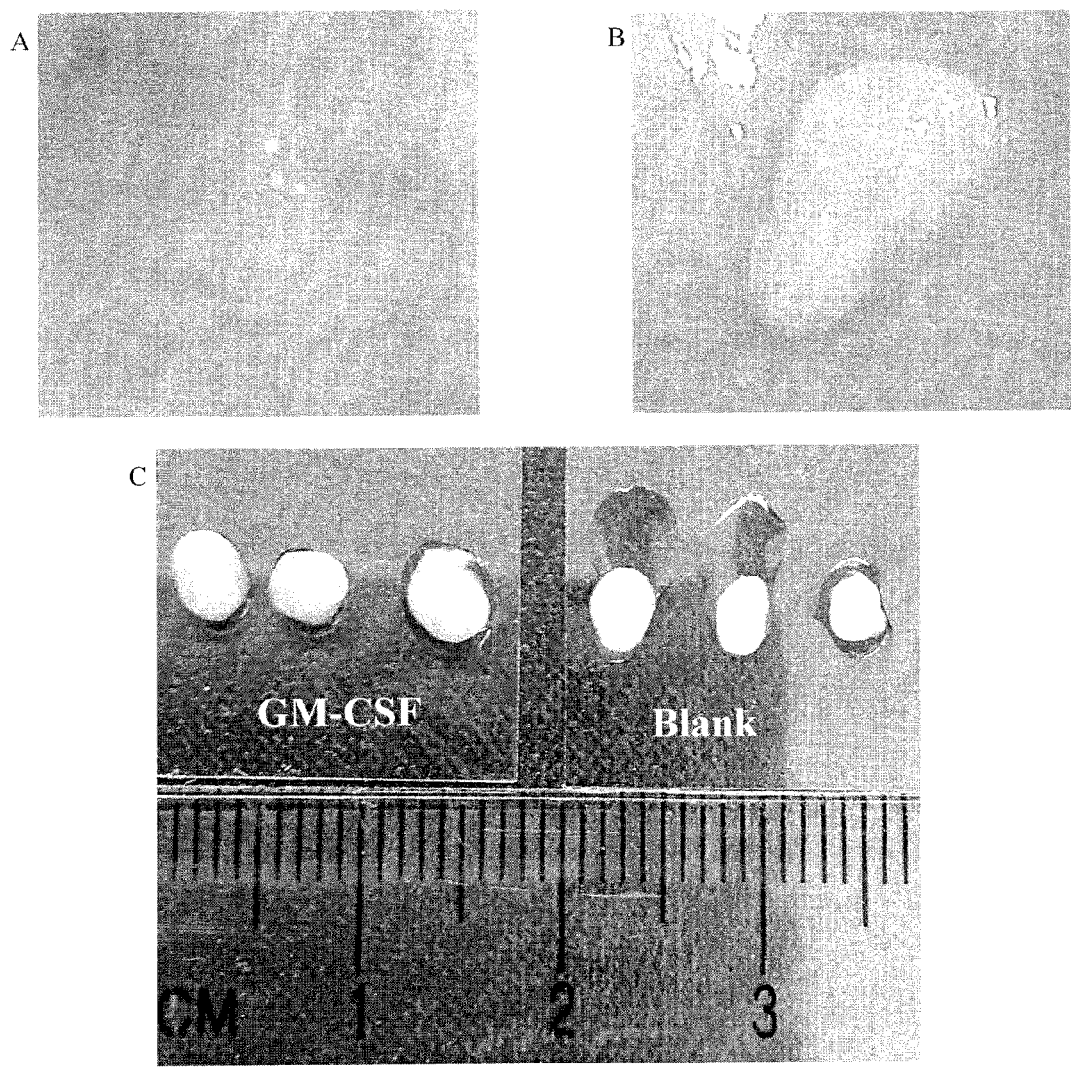

FIGS. 39A-C are images of cryoGelMA gels implanted for 17 days. FIG. 39A is an image of a blank cryoGelMA gel. FIG. 39B is an image of a GM-CSF releasing cryoGelMA gel. FIG. 39C depicts the sizes of recovered blank versus GM-CSF releasing cryoGelMA gels after injection into mice.

Figure 40:
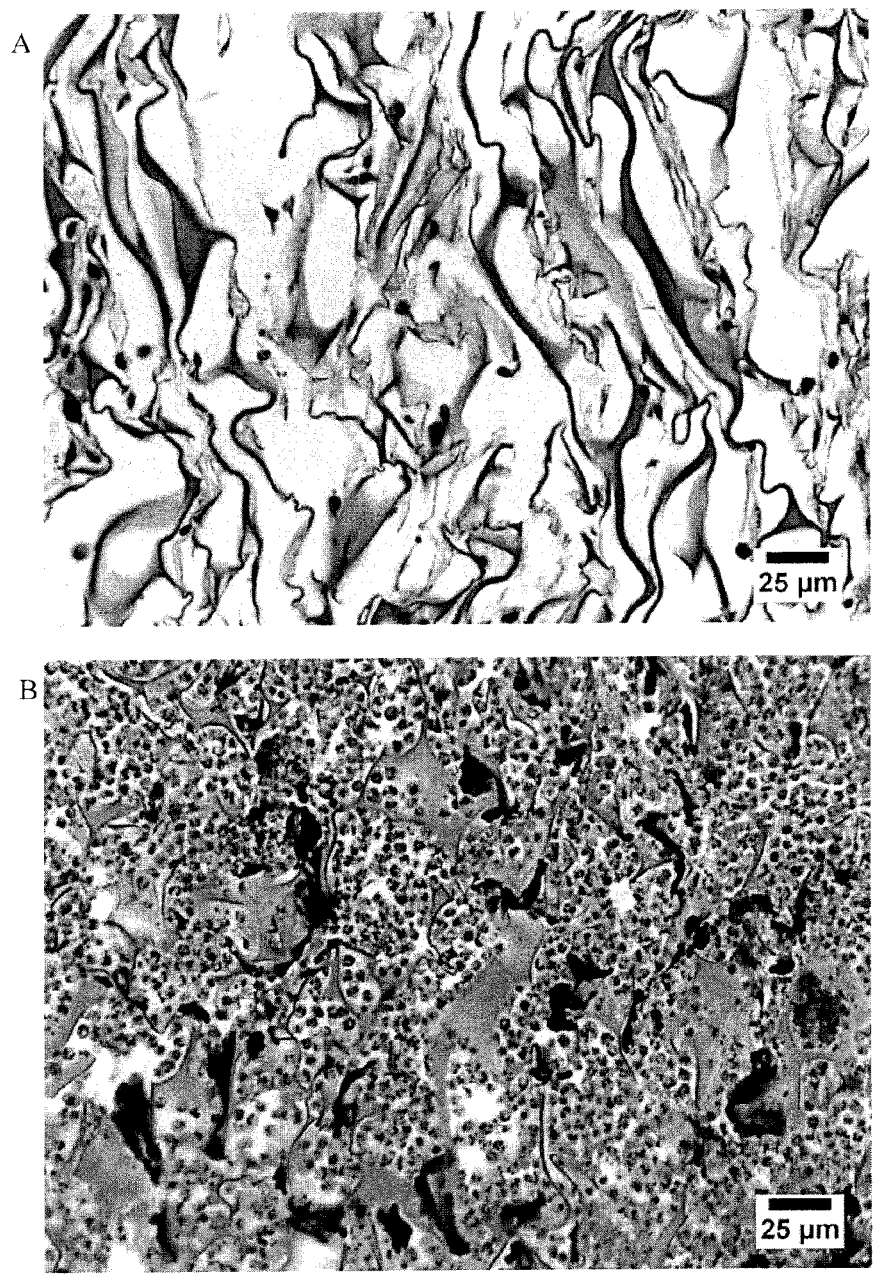

FIG. 40A is a histological image of the center of a blank cryoGelMA scaffold 14 days after subcutaneous injection into mice. FIG. 40B is a histological image of the center of a GM-CSF releasing cryoGelMA scaffold 14 days after subcutaneous injection in mice.

Figure 41:
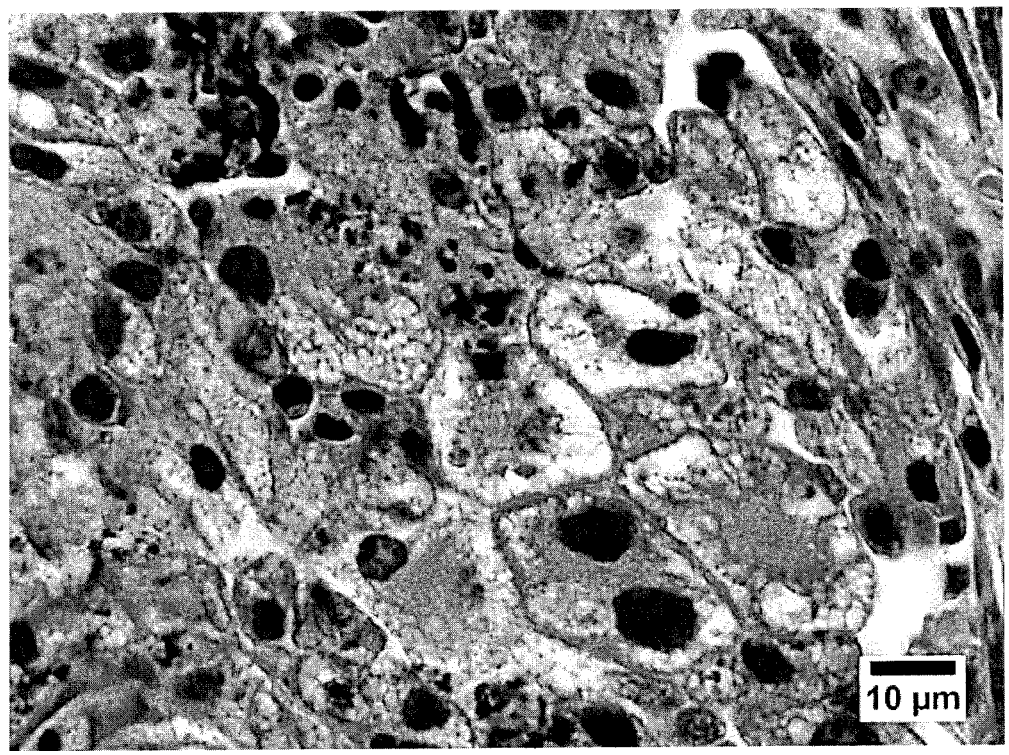

FIG. 41 is a histological image of the injection site of GM-CSF releasing cryoGelMA in a mouse, depicting the presence of macrophages.

Figure 42:
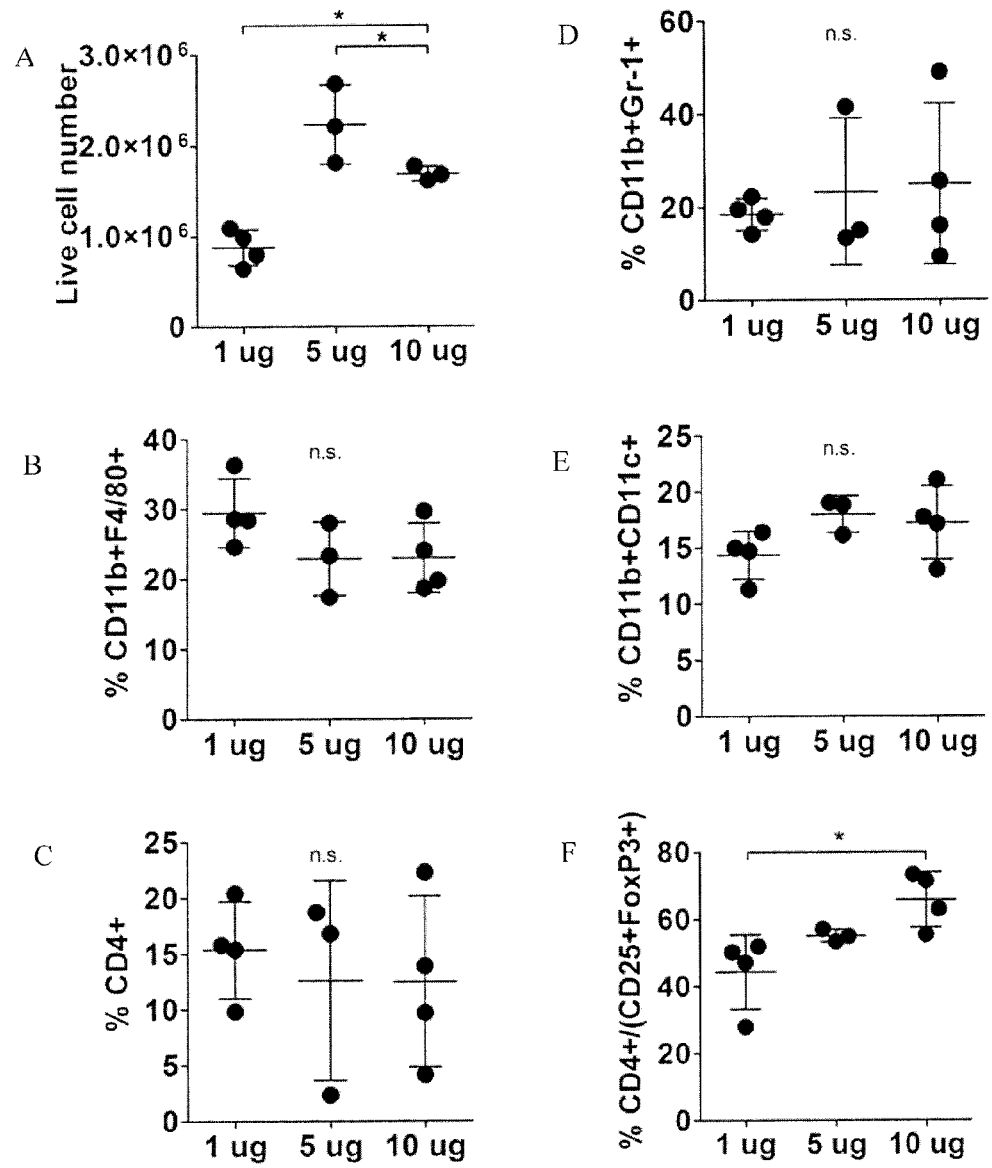

FIGS. 42A-F are a set of graphs indicating the number of cells of various types recruited to the cryoGelMA at various doses of GM-CSF. Error bars represent the standard deviation of the mean. Data were compared using ANOVA with Bonferroni's post-hoc test (*$p<0.05$). FIG. 42A shows the number of live cells recruited to the cryoGelMA. FIG. 42B shows the percent of cells that are macrophages (CD11b+F4/80+). FIG. 42C shows the percent of cells that are CD4+. FIG. 42D shows the percent of cells that are granulocytes (CD11b+Gr-1+). FIG. 42E shows the percent of cells that are dendritic cells/macrophages (CD11b+CD11c+). FIG. 42F shows the percent of cells that are CD4+ regulatory T cells (CD4+/(CD25+FoxP3+).

Figure 43:
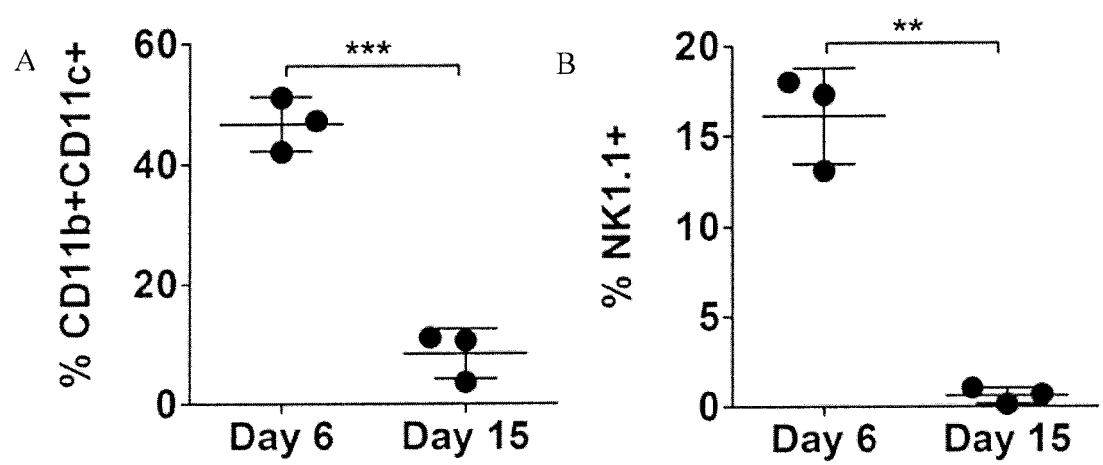

FIGS. 43A-B are a set of graphs showing the proportion of various cell types as a percentage of all live cells resident in cryoGelMA gels on day 6 and 15 after injection into mice. Error bars represent the standard deviation of the mean. Data were compared using a two-tailed unpaired Student's t-test with Welch's correction ($p<0.01$, *$p<0.001$). FIG. 43A shows the percentage of cells that are CD11b+CD11c+. FIG. 43B shows the percentage of cells that are NK1.1+.

Figure 44:
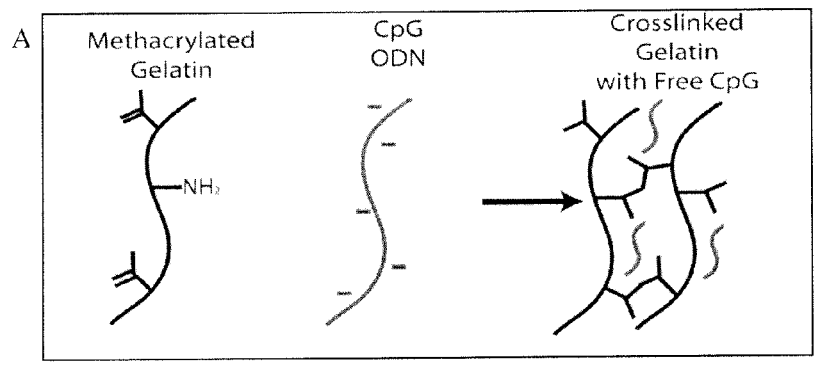
Figure 44:
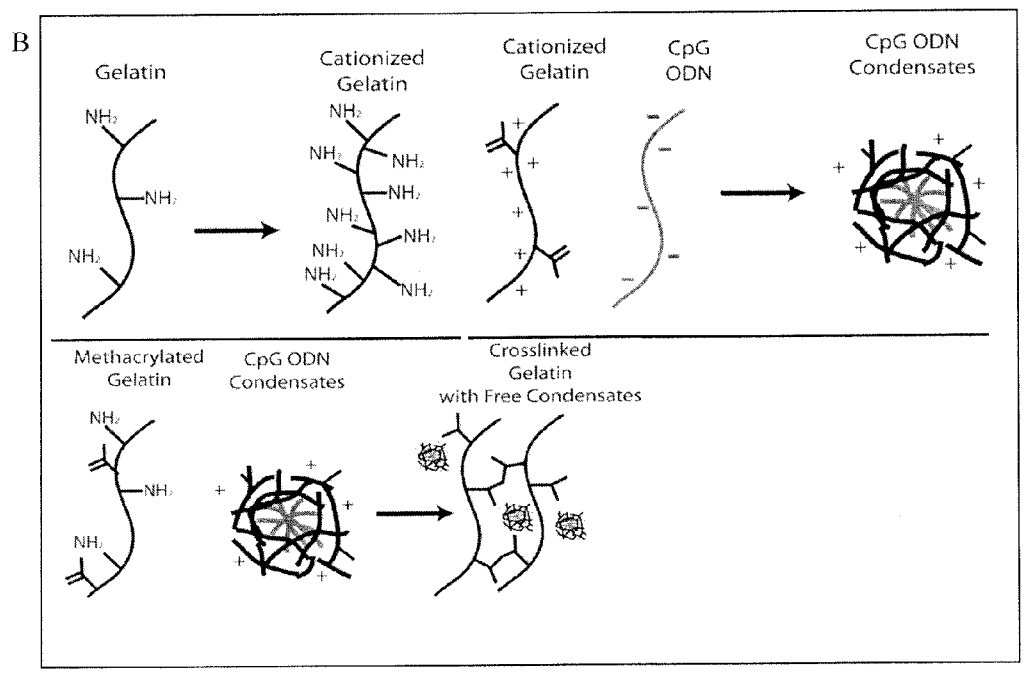

FIGS. 44A-B are schematics of various CpG incorporation strategies into cryoGelMA gels.

Figure 45:
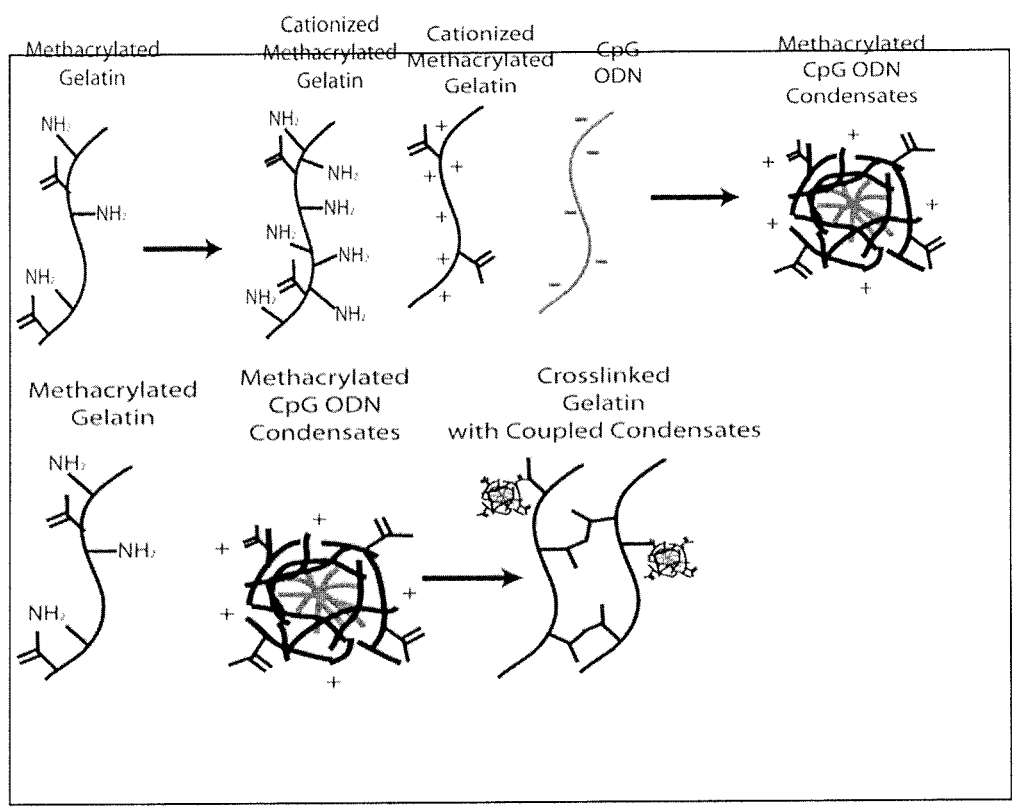

FIG. 45 is a schematic of a CpG incorporation strategy into cryoGelMA gels.

Figure 46:
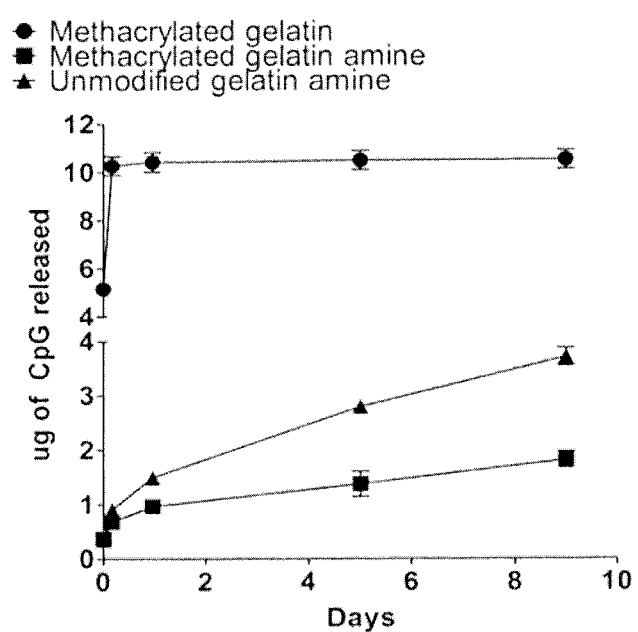

FIG. 46 is a graph showing the rate of CpG release from various cryoGelMA gels.

Figure 47:
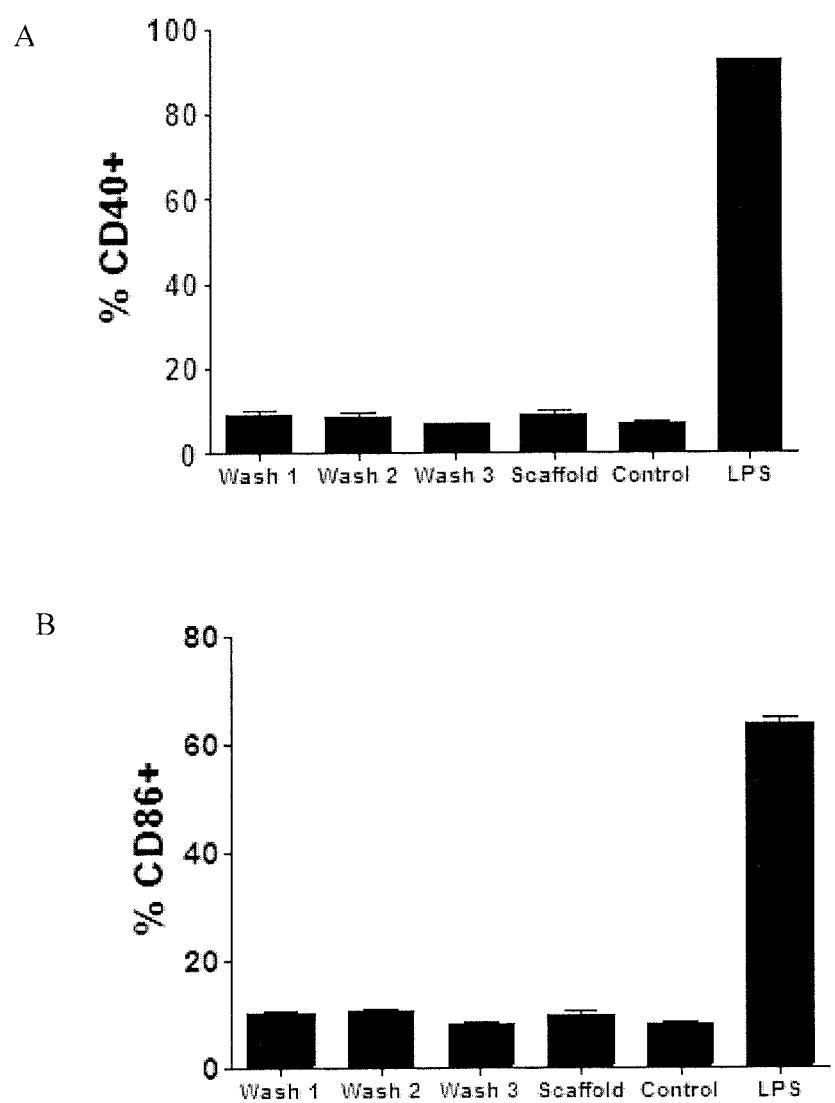

FIG. 47A is a bar graph showing the percentage of mouse bone marrow derived dendritic cells that are CD40+ after culturing in cryoGelMA conditioned media. FIG. 47B is a bar graph showing the percentage of mouse bone marrow derived dendritic cells that are CD86+ after culturing in cryoGelMA conditioned media.

Figure 48:
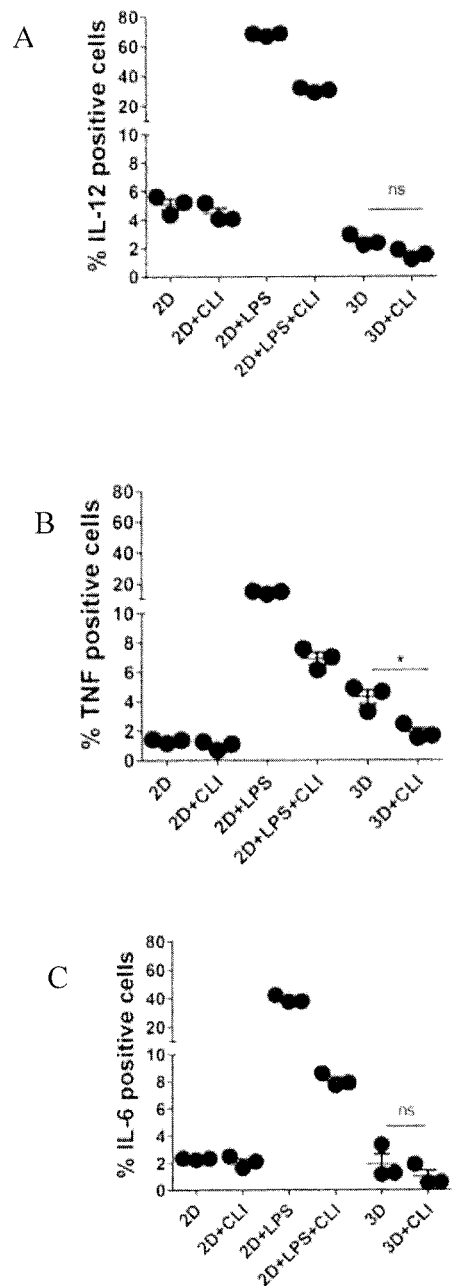

FIG. 48A is a graph showing the percentage of IL-12 positive dendritic cells after culturing in various conditions. FIG. 48B is a graph showing the percentage of TNF positive cells after culturing in various conditions. FIG. 48C is a graph showing the percentage of IL-6 positive cells after culturing in various conditions.

Figure 49:
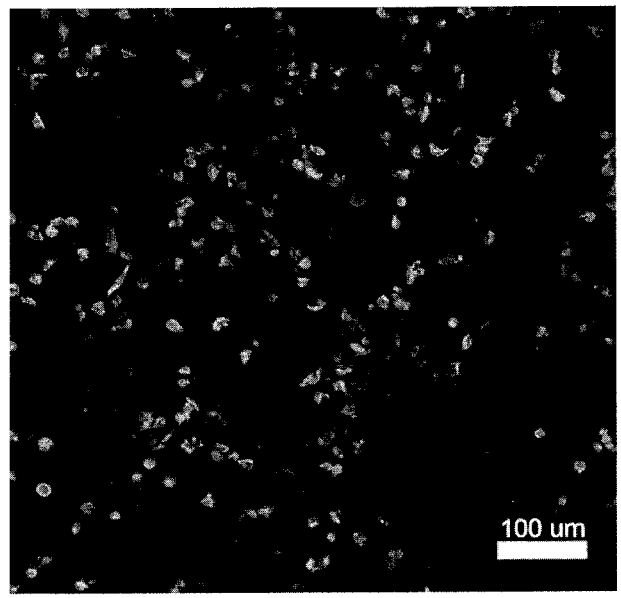

FIG. 49 is a fluorescence microscopy image of a histological section from a cryoGelMA gel after seeding with mouse bone marrow derived dendritic cells. Sections were stained for F actin (green) and nuclei (blue) 48 hours after seeding.

DETAILED DESCRIPTION

A major drawback in today's surgical implantation of three dimensional scaffolds is the trauma created by physicians while administering the scaffolds/devices. The compositions and methods described herein reduce the cost and invasiveness of the cell therapy and/or tissue engineering approach. Prior to the invention described herein, tissue engineering and cell therapy often used devices and polymer scaffolds that required surgical implantation. Implantation of polymer scaffolds at a surgical site requires anesthesia and incisions, each of which treatment methods have undesirable side effects. Described herein are compositions and methods that allow tissue engineers, physicians, and surgeons to engage in cell therapy and tissue engineering applications in a less invasive manner, thereby removing the need for surgical implantation. As described in detail below, injectable gel devices were developed to reduce the invasiveness of a cell therapy or tissue engineering system, thereby eliminating the need for, or reduce the size of, any incisions required to implant the material. For a system to be injectable, it must be capable of flowing through a hollow small-bore needle. Methods of implantation of a gel device or injection of a liquid for polymerization in situ presented a number of challenges including short response time, proper gelation conditions, appropriate mechanical strength and persistence time, biocompatibility, and the likelihood to protect protein drugs or cells in some adverse environments. In order to overcome these limitations, deformable fully-crosslinked and pre-shaped porous gel devices that are easily prepared, processed, and injected through the needle of a syringe was developed.

Earlier injectable hydrogels (e.g., U.S. Pat. No. 6,129,761) allowed for the formation of scaffolds in situ but had several major drawbacks. First, potential problems occur with in situ polymerization including heat generation and un-reacted toxic chemicals. Additionally, slow gelation kinetics and in vivo biofluid dynamics involve dispersion of pre-gel solution leading to poor cell entrapment and physical integrity of the gel. Finally, nanosized pore architecture of scaffolds impedes efficient oxygen delivery, nutrient exchange, cell-movement, and long-term survivability of tissue cells.

The invention described herein provides a minimally-invasive method of injecting preformed macroporous hydrogels that are loaded with cells and/or therapeutics. Cells are optionally implanted and cultured onto the polymeric matrix before or after administration to a subject. Food and Drug Administration (FDA)-approved polymer-based scaffolds that support the attachment and proliferation of cells, degradable and capable of releasing drugs (e.g., proteins) at a controlled rate in vivo are designed in any desirable size and shape, and injected in situ as a safe, preformed, fully characterized, and sterile controlled delivery device. Described in detail below are biologically active cell-seeded injectable scaffolds with structural integrity within the body that controllably deliver growth factors while providing cellular building blocks to enhance tissue formation. Seeding and organizing cells prior to administration of macroscopic injectable matrices enhance in vivo cell engraftment and provide cell support and guidance in the initial tissue formation stage. This invention is useful for clinical applications including artificial extracellular matrix for tissue engineering, dermal filler in cosmetic surgery, controlled release reservoir for drug and cell delivery, and immune cell reprogramming for cancer vaccines. Additional benefits include less injection pain, less bleeding/bruising and higher levels of patient satisfaction.

The present invention describes a non invasive strategy to administer large-size macroporous biodegradable hydrogels as a 3-D scaffold and a drug delivery platform. Any biocompatible polymers or monomers undergoing cryopolymerization are utilized. Suitable polymers and monomers include naturally derived polymers (alginate, hyaluronic acid, heparin, gelatin, carob gum, collagen, etc.) and synthetic polymers (poly(ethylene glycol) (PEG), PEGylated glutaminase (PEG-PGA), PEG-poly(L-lactide; PLA), poly (2-hydroxyethyl methacrylate) (pHEMA), PAAm, poly(N-isopropylacrylamide) (PNIPAAm), etc.). This ability to use different materials is useful in different applications and adds a further degree of versatility to the compositions and methods described herein. The highly elastic macroscopic scaffolds with spongy-like morphology are prepared by cryogelation, a technique used to produce polymeric materials with large interconnected pores, high volume fraction porosity within soft, mechanically stable and high water absorbing capacity. As described below, the cryogels allow for the injectability of preformed large-size scaffolds through a needle without the need of an invasive implantation. Flowable material can fill any defect due to the sponginess of the network. Elastic deformation of cryogels by external forces (mechanical deformation) led to abrupt gel shrinkage with full shape recovery capability, which is useful in the design of injectable preformed scaffolds for cell delivery in a minimally-invasive fashion for tissue engineering and regenerative medicine.

The use of large-size preformed scaffolds (>1 mm) mimicking the extracellular matrix was evaluated. Described herein is the design of large biomaterials with various shapes and sizes ranging from 2 mm up to 8 mm that are employed as injectable cell-laden scaffold cryogels. Injectable macroscopic hydrogels are supplied in individual treatment syringes for single patient use and ready for injection (implantation). The gel, consisting of crosslinked alginate suspended in a physiologic buffer, is a sterile, biodegradable, non-pyrogenic, elastic, clear, colorless, homogenized scaffold implant. The injectable gels are packaged in proprietary luer-lock syringes that are injected via a 16-gauge or smaller diameter needle depending on the size of the gel.

The strategies described herein are for delivery of preformed biomaterials suitable for minimally invasive therapies. Injectable macroscopic biomaterials are useful as surgical tissue adhesives, space-filling injectable materials for hard and soft tissue repair, drug delivery, and tissue engineering. Described herein is an approach of pure alginate scaffolds fabrication, which resulted in the formation of, interconnected, superporous network (pore size in the range of 10 $\mu$m-600 $\mu$m). These spongy-like gels are highly flexible and squeezable, capable of releasing up to 70% of their water content without altering the gel microstructure. Optionally, the gel further includes a large range of purified polymers such as hyaluronic acid, heparin, carob gum, gelatin etc; or a cell adhesive molecule such as fibronectin, or integrin binding peptide. In addition, the hydrogel is used as a drug reservoir for the controlled delivery of one or more therapeutic agents. Alginate-based gels have excellent mechanical properties, elongation, and fast shape recovery by elasticity. The shape of the gels, which was deformed by an external force (e.g., shear stress), was recovered by swelling in a very short time (<1 s). This recovery had good persistence and repeatability. The superporous (e.g., greater than 75% porosity) scaffolds described herein offer significant advantages such as injectability and easy and efficient cell encapsulation post-polymerization. For example, the cryogels are characterized by porosities of 80-90% or more. Animal studies were performed to examine the integration of the spongy-like gels with the host tissue show that the alginate-based scaffolds are biocompatible and do not elicit an immune response or rejection when injected in mice.

Over the past few decades, whole cell autologous cancer vaccines have been used for broad, tumor associated antigen presentation and patient-specific cancer immunotherapy. However, only a limited clinical efficacy has been achieved. To improve cell-based cancer vaccines efficacy, the invention features a vaccination system enabling recruitment of dendritic cells while creating an immunogenic microenvironment consisting of irradiated tumor cells along with adjuvant could enhance T-effector responses and therefore protective immunization. To this end, a sponge-like macroporous biomaterial system was prepared by cryogelation and designed to not only to improve tumor cell engraftment, but also to control the release of immunomodulators such as GM-CSF (recruitment factor) and CpG (programming factor), and finally to enhance immune-cell trafficking and activation in situ. Unlike most surgically implantable scaffolds, the injectable cryogel-based vaccine is minimally invasive and can be administrated through a conventional small-bore needle. Upon subcutaneous injection of the vaccine depot into mice, T effector responses were boosted, resulting in protective immunity in the context of melanoma. Protective, safe, and long-term anti-tumor immunity was generated with these materials, as 80% survival was achieved in animals that otherwise die from cancer within 30 days. As described in detail in the Examples below, 100% survival was achieved after tumor rechallenge on vaccinated mice following 4 months post vaccination, demonstrating a specific, strong, and durable immunological protection in the event of tumor recurrence. This injectable material-based vaccination regime holds high promises to replace traditional whole cell vaccination.

Synthesis of Methacrylated-Alginate (MA-Alginate) and Other Modified Polymers

Methacrylated alginate (MA-alginate) was prepared by reacting high molecular weight alginate with aminoethyl methacrylate (AEMA). To synthesize methacrylated alginate with 100% theoretical methacrylation of uronic acid carboxylate groups, high molecular weight sodium alginate (1 g) was dissolved in a buffer solution (0.6% w/v, pH ~6.5) of 100 mM MES containing 0.5 M NaCl. N-Hydroxysuccinimide (NHS, 1.3 g) and N-(3-Dimethylaminopropyl)-N′-ethylcarbodiimide hydrochloride (EDC, 2.8 g) was added to the reaction mixture to activate the carboxylic acid groups of the alginate. After 5 min, AEMA (2.24 g, molar ratio of NHS:EDC:AEMA=1:1.3:1.1) was added to the product and the reaction was maintained at room temperature for 24 h. The mixture was precipitated with the addition of excess of acetone, filtered, and dried in a vacuum oven overnight at room temperature. $^1$H NMR was used to confirm the chemical modification of alginate and characterize the degree of functionalization of MA-alginate (FIG. 10).

Any biocompatible water-soluble polymer or monomer can be used to make injectable cryogels. Several monomers/polymers or a combination of polymers have been used to make the injectable cryogel devices described herein, e.g., hyaluronic acid, gelatin, heparin, dextran, carob gum, PEG, PEG derivatives including PEG-co-PGA and PEG-peptide conjugates. For example, the polymers may be a combination of degradable and non-degradable synthetic polymers and natural polymers (polysaccharides, peptides, proteins, DNA). Biocompatible synthetic polymers include Polyethylene glycol (PEG), Polyvinyl alcohol (PVA), Poly(2-hydroxyethyl methacrylate) (PHEMA), Poly(N-isopropylacrylamide) (PNIPAAm), Poly(acrylic acid) (PAAc), Polyesters (e.g. Polylactide, Polyglycolide, Polycaprolactone), and Polyanhydrides. Naturally-occurring polymers include Carbohydrates (e.g. Starch, Cellulose, Dextrose, Alginate, Hyaluronic Acid, Heparin, Dextran, Gellan Gum, etc), Proteins (e.g. Gelatin, Albumin, Collagen), Peptides, and DNA. All compositions are purified prior to fabrication of the hydrogels.

In addition to the free radical polymerization process to cross-link the polymers and make chemically cross-linked injectable cryogels (polymerization time is about 17 hr), gels are optionally polymerized using other processes. Injectable cryogels can be classified under two main groups according to the nature if their cross-linking mechanism, namely chemically and physically cross-linked gels. Covalent cross-linking processes include radical polymerization (vinyl-vinyl coupling), michael-type addition reaction (vinyl-thiol cross-linking), Condensation (carboxylic acid-alcohol and carboxylic acid-amine cross-linking), Oxidation (thiol-thiol cross-linking), Click chemistry (1,3-dipolar cycloaddition of organic azides and alkynes), Diels-Alder reaction (cycloaddition of dienes and dienophiles), Oxime, Imine and Hydrazone chemistries. Non-covalent cross-linking include Ionic cross-linking (e.g. calcium-crosslinked alginate), Self assembly (phase transition in response to external stimuli, such as Temperature, pH, ion concentration, hydrophobic interactions, light, metabolite, and electric current).

Cryogel Fabrication

Figure 2:
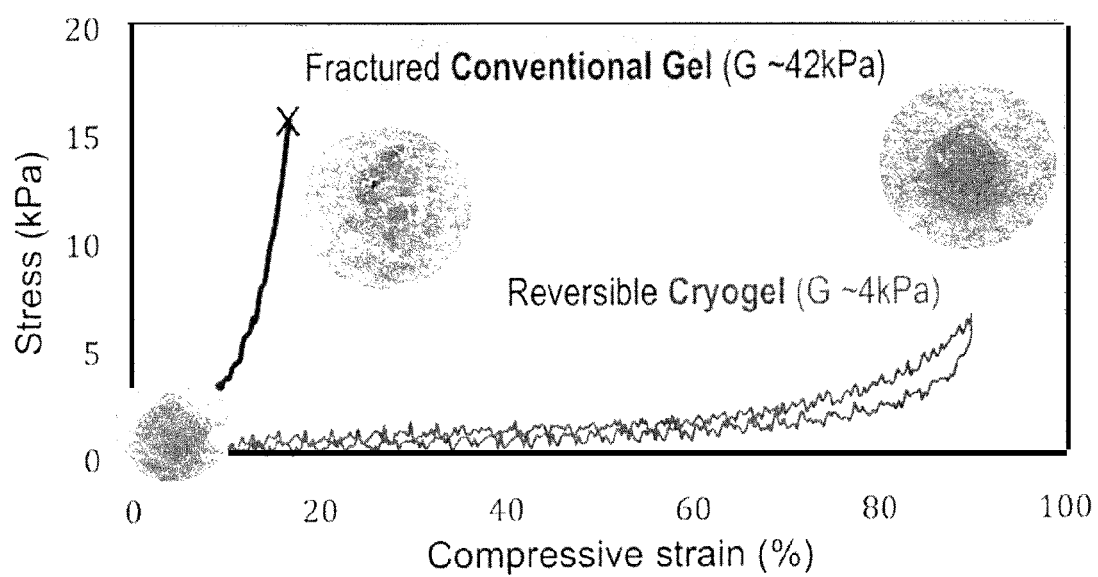
FIG. 2 is a line graph demonstrating stress vs. strain curves for conventional nanoporous and macroporous 1% rhodamine-labeled MA-alginate gels subjected to compression tests. In contrast to the brittle nature of the conventional nanoporous gels, alginate cryogels have the ability to withstand reversibly large deformation while keeping their structural integrity and shape memory properties.

Cryogel matrices were synthesised by redox-induced free radical polymerization of, e.g., MA-alginate in water. Alginate cryogels are synthesized by mixing 10 mg (1% wt/v) of MA-alginate macromonomer in deionized water with TEMED (0.5% wt/v) and APS (0.25% wt/v). The mixture is immediately poured into a pre-cooled Teflon mold and frozen at −20° C. After cryo-crosslinking has finished, gels are heated to room temperature to remove ice crystals, and washed with distilled water. Cell-adhesive cryogels were synthesized using a RGD-containing peptide composition, e.g., ACRL-PEG-G4RGDASSKY (SEQ ID NO: 2) as a comonomer (0.8% wt/v) during the polymerization. (Acryloyl is abbreviated ACRL.) By mixing the RGD-containing peptide composition (monomers) with the alginate, the RGD becomes chemically attached (covalently attached) to the polymer structure. RGD integrin-binding motif was used to promote cell-substrate interactions. NMR spectroscopy was used to characterize vinyl conversion of MA-alginate macromonomer after cryopolymerization. As shown in FIG. 2, full disappearance of methylene protons (between 5.3-5.8 ppm) for MA-alginate macromonomer (1% wt/v) was reached after the cryopolymerization process in the presence of the initiator system (APS/TEMED). This indicates that high vinyl conversions can be achieved for cryogels (see FIG. 11). Injectable cryogels can be prepared at different concentrations depending on the MW and the degree of chemical modification of the polymer itself (1% wt/v was chosen as a proof of concept).

As described above, RGD remains attached to the polymer structure by virtue of covalent bonding (co-polymerization). However, certain biomolecules are to be released following administration of the cryogel to the subject. In this case, the biomolecules are simply mixed with the polymer prior to the cryogelation process.

Cryogelation

Cryogels are a class of materials with a highly porous interconnected structure that are produced using a cryotropic gelation (or cryogelation) technique. Cryogelation is a technique in which the polymerization-crosslinking reactions are conducted in quasi-frozen reaction solution. During freezing of the macromoner (MA-alginate) solution, the macromonomers and initiator system (APS/TEMED) expelled from the ice concentrate within the channels between the ice crystals, so that the reactions only take place in these unfrozen liquid channels. After polymerization and, after melting of ice, a porous material is produced whose microstructure is a negative replica of the ice formed. Ice crystals act as porogens. Pore size is tuned by altering the temperature of the cryogelation process. For example, the cryogelation process is typically carried out by quickly freezing the solution at −20° C. Lowering the temperature to, e.g., −80° C., would result in more ice crystals and lead to smaller pores.

The advantage of these so-called "cryogels" compared to conventional macroporous hydrogels obtained by phase separation is their high mechanical stability. They are very tough, and can withstand high levels of deformations, such as elongation and torsion; they can also be squeezed under mechanical force to drain out their solvent content. The improved mechanical properties of alginate cryogels originate from the high crosslinking density (highly methacrylated alginate polymerizes into cross-linked polymer structures with a relatively high crosslink density) of the unfrozen liquid channels of the reaction system. Thus, after polymerization, the gel channels with high polymer content are perfect materials for building the pore walls.

Biomolecules, e.g., GM-CSF, CpG nucleic acids, are entrapped in the polymer structure but not chemically linked to it. Thus, these molecules are released from the cryogel by diffusion or gel degradation over time. For example, low molecular weight compositions (less than 10 kDa molecular mass), e.g., CpG oligonucleotides, are released by diffusion. Larger entrapped molecules (greater than about 10 kDa, e.g., 10-50 kDa in molecular mass), e.g., proteins, large DNAs, e.g., plasmid DNA, are released primarily by cryogel degradation.

Human Recombinant GM-CSF (e.g., available from Pepro-Tech, Catalog #300-03) is encoded by the following polypeptide sequence (SEQ ID NO:5):

```
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Injectable Hybrid Cryogels

Injectable delivery systems for therapeutic proteins (e.g., hydrogels and microspheres) have attracted wide attention. Conventional hydrogels, however, typically release their hydrophilic contents too rapidly in a large initial burst, and phagocytes may clear microspheres within a relatively short time period after administration.

Microsphere/cryogel combination systems achieve a controlled and sustained release of proteins as an injectable delivery system. PLGA microspheres (size ~10-50 μm) containing a model protein (GM-CSF) were prepared and then mixed with a MA-alginate pre-gel solution prior cryopolymerization. The mixing ratio of the components was optimized to retain injectability and shape memory properties of pure alginate cryogels. As shown in FIG. 12, PLGA microspheres were physically entrapped within the cryogel network (polymeric walls) of cryogels. Also, hybrid cryogel have been created as a carrier for controlled delivery of hydrophobic and/or low molecule weight drugs. The results not only provide a strategy for delivery drugs from an injectable 3-D preformed macroporous scaffolds as a sustained-release drug carrier but also open an avenue for the design of the hybrid injectable hydrogels.

Other examples of hybrid polymer combinations include cryo-ferrogels and polydiacetylene-based cryogels. One class of injectable porous biomaterials for on-demand drug and cell delivery comprises cryo-ferrogels. The magnetic-sensitive scaffolds based on macroporous elastic alginate-based cryo-ferrogels, were fabricated with 3-D connected macropores and coupled with magnetic particles ($Fe_3O_4$ nano- and micro-particles) and cell-binding moieties. Under applied magnetic fields, the loaded macroporous ferrogel with biological agents lead to large and prompt deformation triggering release of drugs and cells in a controlled fashion. In another example, injectable color-changing biomaterials such as polydiacetylene-based cryogels, which change in response to external stimuli such as mechanical forces. The materials contain mechanophore-molecules (e.g., Polydiacetylene Liposome) that undergo a geometric distortion when a certain amount of force is exerted upon it, leading to a color transition. Smart polymers that change color when the material becomes overstressed are very useful to identify cell-substrate interactions and to accurately measure deformations.

Administration of Injectable Cryogels

Syringes and needles are typically used to introducing the cryogels into the body. The term "syringe" technically refers to the reservoir (that holds the liquid) and the plunger (which pushes the liquid out of the reservoir). The "needle" is the part that enters the body, e.g., into a vein, under the skin, or into muscle or other tissue. The word "syringe" is also sometimes used to refer to the entire reservoir/plunger/needle combination. They come in a variety of sizes, e.g., a common reservoir size is 1 cc (1 cubic centimeter (cc)=1 milliliter), with a 25 gauge needle size or smaller.

The needle gauge refers to the size of the bore or hole in the needle. The higher the gauge, the thinner the needle (and the smaller the hole). A 28 gauge needle (abbreviated 28 G) is therefore thinner than a 25 gauge needle, which is in turn thinner than an 18 gauge needle. Insulin needles are typically ½ inch in length and tuberculin needles are typically ⅝ of an inch in length. As inscribed on packaging, needle length appears after the gauge number: "28 G ½" refers to a 28 gauge needle that is ½ inch long.

Larger gauge (frequently 23 G or 21 G), longer needles are often used for intramuscular injections. Muscle syringes are typically 1 cc in volumes, but larger volumes are sometimes, e.g., 2 to 5 ccs syringes, depending on the application. Larger volumes and larger bores are appropriate for delivery of cryogels for larger scale muscle repair or regeneration, e.g., after extensive or traumatic laceration of tissue such as injuries incurred in battle or car/plane accidents. Intravenous injectors or needles are used for fine or delicate tissue therapy, e.g., cosmetic dermal filler administration. Such applications typically use shorter needles no larger than 25 G.

Survivability of Cells after Injection

Reversible compactible behavior enables pre-formed cryogels with desired physical properties, as characterized ex-vivo, to be delivered in-vivo via application of a moderate non-destructive shear stress during injection through a syringe. Studies were carried out to evaluate whether the fluid velocity, dynamic pressure, and shear stress resulting from the injection affects cell viability.

The data indicated that, during the injection, cells integrated in the RGD-modified cryogel were protected by the scaffold from mechanical damage. Although adherent cells may experience some shear stress applied during the injection, cryogels are capable of absorbing most of the energy when the scaffolds are compressed, thereby, maintaining high cell viability (92%) and their proliferative potential as shown in FIG. 13.

Thus, the shear stress (or compression) applied to cells in the cryogel as they pass through the bore of a needle or other delivery apparatus such as a catheter does not measurably hurt or damage the cells within the cryogel. Following passage through a needle or other delivery apparatus, cell viability was routinely 90% or greater.

Cancer Vaccines and Melanoma

Vaccination has been one of the most effective means to increase global health with the power to completely eliminate infectious diseases by activating the immune system. The ability of the immune system to protect from disease extends to cancer, as evidenced early on with bacterial mixtures in treating certain cancers to more recently the therapeutic success of negative co-stimulatory molecule blockade. See, e.g., Mansoor W et al. Br. J. Cancer. 2005; 93(10):1085-91. Thus, by activating immunity through such methods as cancer vaccines, it is possible to boost the immune system to enable it to combat cancer more effectively.

Malignant melanoma is the deadliest form of skin cancer, and its incidence is rising. See, e.g., Miller A J et al. N. Engl. J. Med. 2006; 355:51-65. Despite the recent development of small molecule inhibitors and negative co-stimulatory molecule blockade, the prognosis for late stage melanoma is poor, and many of the agents have small therapeutic windows and result in severe side effects. As more information about immune cells is discovered, researchers have realized that the immune system plays a crucial role in preventing cancer including melanoma. Experimental studies have shown that activation of both innate and adaptive immunity can prevent tumor development; therefore the development of prophylactic vaccine against melanoma may provide long-term protection. A major challenge for designing prophylactic cancer vaccines is to define immunogenic and safe cancer antigens that can serve as targets for effective vaccines, including tumor-specific antigens on the tumor.

Some progress has been made in the development of vaccines against cervical cancer, caused by human papilloma virus. See, e.g., Begue P et al. Bull. Acad. Natl. Med. 2007; 191:1805-16. However, vaccine development of other types of cancers poses more challenges, since most cancers are believed not to be caused by infectious agents, but rather, defects in cellular proteins. Since these proteins are very similar to those found in normal cells, it is difficult to develop vaccines targeting the cancer cells while sparing normal cells. However, some tumor cells display unusual antigens or cell surface receptors that are rare or absent on the surfaces of healthy cells. See, e.g., Sensi M et al. Clin. Cancer Res. 2006; 12:5023-32. Although cancer vaccines with defined antigens are commonly used, the use of whole tumor cells in cancer immunotherapy is a promising approach and can obviate some important limitations in vaccine development. See, e.g., Chiang C L, et al. Semin Immunol. 2010; 22:132-43. Whole tumor cells are a good source of tumor associated antigens and can induce simultaneous Cytotoxic T lymphocytes and T helper cell activation. Whole cell autologous vaccines typically consist of irradiated tumor cells that are often transfected with granulocyte-macrophage colony-stimulating factor (GM-CSF) or the adoptive transfer of pulsed dendritic cells (DC) or transfected T cells. Inflammatory GM-CSF is a cytokine that plays a critical role in immunoregulation. See, e.g., Shi Y et al. Cell Res. 2006; 16:126-33. GM-CSF can overcome tumor-induced immune suppression and promotes the recruitment and maturation of specialized antigen-presenting cells (APC) such as DC. DC are potent antigen-presenting cells and play a pivotal role in T cell-mediated immunity. GM-CSF-mediated activation of APC results in upregulation of MHC class II, co-stimulatory molecules and cytokine production. See, e.g., Caulfield J J et al. Immunology. 1999; 98:104-10. It increases antibody responses and cellular immunity after immunization. These combined features have made GM-CSF a commonly used cytokine to boost anti-tumor immunity. See, e.g., Disis M L et al. Blood. 1996; 88:202-10; Dranoff G et al. Proc Natl Acad Sci USA. 1993; 90:3539-43; and Dranoff G. Immunol Rev. 2002; 188:147-54. In a murine melanoma model, a promising cancer cellular vaccine demonstrated the potency of prophylactic GM-CSF-transduced autologous tumor cell vaccines in prevention of tumor outgrowth. See Dranoff G et al. Proc Natl Acad Sci USA. 1993; 90:3539-43; and Dranoff G. Immunol Rev. 2002; 188:147-54. However, in these studies, cells required a substantial in vitro genetic manipulation, leading to high cost and significant regulatory concerns. More importantly, cellular transplantation have been hampered by poor cell viability (<10%), which may prevent long-term GM-CSF secretion and tumor antigen exposition and ultimately vaccine efficacy. See, e.g., Aguado B A et al. Tissue Eng. Part A. 2012; 18:806-15.

Clinical trials testing the efficacy of whole cell autologous vaccines for the treatment of many cancers including melanoma have been conducted with limited success. An advantage of whole cell irradiated tumor vaccines versus standard peptide or protein vaccination is that a wide diversity of patient-specific, tumor associated antigens are presented on tumor MHC, reducing the concern for cancer immunoediting. However, these techniques present several drawbacks. GM-CSF transfected cells require expensive and laborious gene transfection processes while adoptively transferred cells may fail to engraft. Further, the clinical response has been limited. Many experimental studies have shown that activation of both innate and adaptive immunity can prevent tumor development. The invention overcomes these drawbacks, as the prophylactic vaccine against melanoma provides long-term protection against the disease.

Creating an infection-mimicking microenvironment using an implantable porous scaffold-based device by appropriately presenting exogenous cytokines (for example, GM-CSF) and danger signals for an extended time, in concert with cancer antigens, may provide an avenue to precisely control and enhance the number and timing of dendritic-cell trafficking and activation, in situ. See, e.g., Ali O A et al. N. at Mater. 2009; 8:151-8; and Ali O A et al. Sci. Transl. Med. 2009; 1:8ra19. In addition to GM-CSF, another key element of infection that mobilizes and activates dendritic cells includes 'danger signals' related specifically to the infectious agent. Cytosine-guanosine oligonucleotide (CpG-ODN) sequences, which are uniquely expressed in bacterial DNA, are potent danger signals that stimulate mammalian dendritic-cell activation and dendritic-cell trafficking. See, e.g., Klinman D M. Nat Rev Immunol. 2004; 4:249-58. However, initial studies using implantable tumor lysate-loaded scaffold vaccines required invasive surgeries to be administered to the patient, limiting sequential vaccinations. See, e.g., Ali O A et al. N. at Mater. 2009; 8:151-8; and Ali O A et al. Sci. Transl. Med. 2009; 1:8ra19. Additionally, tumor lysate can be intrinsically suppressive to DC activation and has been associated with a weaker T cell response and tumor protection than vaccinating with whole tumor cells. See Chiang C L et al. Semin Immunol. 2010; 22:132-43; and Buckwalter M et al. The American Association of Immunologists. 2007; 178:48.16.

In order to improve the efficacy of whole cell cancer vaccines while being minimally invasive upon delivery, the invention provides a way to mimic infection and thereby recruit and program immune cells at a distant site away from the tolerogenic milieu of the tumor environment. For this purpose, an injectable polymeric delivery system was designed to enable simultaneously tumor cell-seeding and immunomodulators delivery while serving as a physical, antigen-presenting structure to which the dendritic cells are recruited, homed, and subsequently activated. Additionally, pre-encapsulation of tumor antigen-associated cells within a hydrogel improves viability by providing biomechanical protection, biochemical survival cues, and scaffolding. See Bencherif S A et al. Proc. Natl. Acad. Sci. USA. 2012; 109:19590-5; Bencherif S A et al. Biomacromolecules. 2009; 10:2499-507; Bencherif S A et al. Biomaterials. 2009; 30:5270-8; Bencherif S A et al. Acta Biomater. 2009; 5:1872-83; Bencherif S A et al. J. Biomed. Mater. Res. A. 2009; 90:142-53; Bencherif S A et al. Biomaterials. 2008; 29:1739-49; Siegwart D J et al. J. Biomed. Mater. Res. A. 2008; 87:345-58; and Kennedy S et al. Adv Healthc Mater. 2013.

The development of injectable cell-loaded sponge-based materials is a promising direction towards a safe, minimally-invasive, and patient-compliant vaccine. This is a promising effective cancer vaccine in the prophylactic treatment of melanoma, eliminating the need for invasive surgeries required implantable scaffolds. The injectable cell loaded vaccine presented herein is a major advancement, particularly when the cancer vaccination is achieved without the need for multiple, systemic injections and high total biomolecules loading. The Examples below further describe an exemplary cancer vaccine based on this concept, containing a polysaccharide-based material (alginate) and bioactive molecules (GM-CSF and CpG-ODN) that have previously proven to be successful as immunomodulatory factors in terms of activation of antigen-presenting cells (APCs) and priming of cytotoxic T cells. See Kratky W et al. Proc. Natl. Acad. Sci. USA. 2011; 108:17414-9. For example, a cancer vaccine of the invention, such as RGD-modified sponge-like hydrogels encapsulating simultaneously GM-CSF and CpG-ODN, was first prepared by a cryopolymerization process before being seeded with whole irradiated tumor cells, resulting in the design of the first syringe-injectable scaffold-based cancer vaccine.

As demonstrated by the data presented herein, a cryogel vaccine containing syngeneic tumor cells, GM-CSF, and CpG-ODN could be injected using a large gauge needle, enrich for DC and T cells, and induce potent, and persistent, anti-tumor immunity. The cryogels were designed to be syringe-injectable and deliver CpG (programming factor) and GM-CSF (programming/recruitment factor) locally and allow for the efficient seeding of melanoma cells. In vivo, the vaccine recruited greater than two million DC and three million T cells to the vaccine site and in the prophylactic setting was able to protect 80% of the animals upon initial challenge and 100% in subsequent re-challenges.

Cancer invokes a tolerogenic milieu that prevents immune clearance, thereby requiring an external boost from immunotherapies to override the immunosuppression. The active immunotherapy system described herein stimulates the patient's immune system and promotes an antigen-specific antitumor effect using the body's own immune cells. In addition, the cryogel-vaccine creates a durable antitumor response that protects tumor recurrence. The strategy in the design of this vaccine was based on manipulating in situ, dendritic cells recruitment, activation, and their dispersion to the lymph nodes.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control. However, some tumor cells display unusual antigens or cell surface receptors that are rare or absent on the surfaces of healthy cells, and which may be responsible for activating cellular signal transduction pathways that cause the unregulated growth and division of the tumor cell. See. e.g., Sensi M et al. Clin. Cancer Res. 2006; 12:5023-32. The unique and flexible vaccine system described herein is a promising cell-based immunotherapy approach for the treatment of melanoma cancer using tumor-cells. In some examples, distinct tumor cell-associated antigens are extracted from patients, multiplied if needed, integrated into the alginate cryogels and administered back into patients to treat different types of cancer.

Advantageously improving expansion and transplantation, the devices of the invention improved cell survival while promoting their proliferation (ex- and in-vivo) after subcutaneous injection of bioluminescent B16-F10 cells when integrated to the cryogels, in comparison to free cells (bolus). In addition, in order to increase cellular engraftment within the polymeric construct, cryogels were functionalized with RGD peptide to promote adhesion and encapsulation of cells through specific RGD-integrin binding. By this approach, the mechanically robust tumor-cell loaded sponge-like vaccines had the ability to support tumor cell attachment before inoculation as well as after delivery to facilitate immune cell-trafficking within unfilled void spaces of the large interconnected pores of vaccines.

In some embodiments, whole cells (containing tumor antigens), taken either from the patient (autologous) or from a different patient (allogeneic) are used to stimulate the immune system to mount a response. Since the tumor cells are irradiated, they are not harmful; rather, they stimulate the host immune system to recognize the tumor cells. The advantages of whole-cell vaccination over other types of immunotherapy that target specific antigens is that multiple and unknown tumor antigens do not need to be identified and may be targeted by both the innate and adaptive immune system. Furthermore, immunity against a single antigen may be ineffective in tumors with heterogeneous cell populations and carries the risk of inducing tumor antigen escape variants. See, e.g., Thurner B et al. J. Exp. Med. 1999; 190: 1669-78.

For the cell-based vaccines described herein, cell surface antigens are among the targets naturally accessible to surveillance by the immune system, particularly by the cellular immune response. Thus, the injectable cryogel technology is a suitable system for the whole-cell vaccination, as not only does the matrix increase survivability and retention of antigen-displaying tumor cells at the vaccine site but it also enhances cancer antigen exposure to immune cells. In addition, cultivated tumor cells on the cell-adherent gel vaccines have a different morphology from those trypsinized and injected directly, which likely contributes to the enrichment of cell surface materials and therefore an improvement in the effectiveness of the sponge-like cryogel cancer vaccines. Several studies have reported that trypsinization of cells triggers release of glycoproteins and sugars from the cell surface, thereby leading to a loss of antigenic properties. See, e.g., Cook G et al. Nature. 1960; 188:1011-2; Gasic G et al. Nature. 1962; 196:170; Uhlenbruck G. Nature. 1961; 190:181; David J et al. J. Exp. Med. 1964; 120:1189-200; Weiss L et al. Exp. Cell Res. 1963; 30:331-8; and Osunkoya B et al. Int. J. Cancer. 1969; 4:159-65. In particular, Molinari and Platt described that polyoma virus-transformed cells treated with trypsin failed to induce a delayed hypersensitivity reaction against tumor-specific antigens in footpad swelling assays. See Molinari J et al. Proc. Soc. Exp. Biol. Med. 1975; 148:991-4. Thus, antigenic targets are present on the surface of cancer cells, and the use of scaffold-based vaccines likely prevents removal of molecules from the cell surface and therefore increases the antigenicity. A major drawback of unfractionated tumor antigens is the possibility of inducing an autoimmune reactivity to epitopes that are shared by normal tissues. See, e.g., Ludewig B et al. J. Exp. Med. 2000; 191:795-804. However, in clinical trials using lysate or whole tumor cells as the source of antigen, no clinically relevant autoimmune responses were detected. See, e.g., Li J et al. Cancer Immunol. Immunother. 2001; 50:456-62.

Tumors are recognized by the immune system through unique tumor associated antigens (TAAs). See, e.g., Buonaguro L et al. Clin Vaccine Immunol. 2011; 18:23-34. Although many TAA targets have been identified and added in the design of new immunotherapeutic strategies, painstaking work remains to be done to fully characterize the immunogenicity of these emerging antigens in the human, identify the most immunogenic epitopes, and test their role as bona fide tumor rejection antigens that can cause tumor regression. A promising alternative to individual TAAs is vaccination using whole tumor cells without defining the antigens. Tumor cells express a whole array of TAAs that are both characterized and uncharacterized, and this rich source of antigens contains epitopes of both CD8+ cytotoxic T cells (CTLs) and CD4+ T helper cells. The parallel presentation of both MHC Class I and II restricted antigens can help to generate a stronger overall anti-tumor response and long term CD8+ T cell memory via CD4+ T cell help. In addition, it would greatly diminish the chance of tumor escape compared to using single epitope vaccines. Furthermore, the use of whole tumor cells eliminates the need to define, test, and select for immunodominant epitopes. The tumor cells can be autologous, i.e., obtained from the patients, or allogeneic "off-the-shelf". Allogeneic tumor cell lines that share one or even several of the TAAs as autologous tumor cells provide a simpler method of delivering antigens in tumor immunotherapy. Allogeneic cell lines can be propagated in large quantities in cell factories and the quality can be easily assessed and monitored in good manufacturing practice facilities.

Through the use of distinct tumor cell-associated antigens, the cellular cryogel-based vaccine platform provided by the invention can be adapted to a variety of cancers. In some cases, active specific immunotherapy involves the priming of the immune system in order to generate a T-cell response against tumor-associated antigens. One example of the active specific approach is adoptive T-cell therapy, which involves the ex vivo cultivation of T cells with demonstrated activity against a specific target cancer antigen. The goal is to increase the frequency of these T cells to achieve therapeutic levels and then infuse them back into the patient via injectable alginate-based cryogels. In some embodiments, T cells are extracted from patients, multiplied in large quantities, integrated into the alginate cryogels and administered back into patients to treat different types of cancer. This type of T-cell therapy was recently shown to be able to boost the body's ability to fight cancers such as leukemia, lymphoma, melanoma, and breast cancer. However, prior to this invention, T cells were limited by difficulties in generating enough cells in vitro, T cells usually undergo necrotic death after transplantation, and a cancer can return if an immune response is not sustained. The vaccine devices described herein are surprisingly advantageous, e.g., in improving cell expansion and transplantation, as the devices improve survival of cells while promoting their proliferation (ex- and in-vivo) after subcutaneous injection of bioluminescent B16-F10 cells when integrated to the cryogel, in comparison to free cells (bolus). See, e.g., Bencherif S et al. Proc. Natl. Acad. Sci. USA. 2012; 109:19590-5. This unique and flexible system is a promising cell-based immunotherapy approach for the treatment of cancers (e.g., breast cancer or melanoma) using allogeneic tumor-specific T cells (adoptive T cell therapy).

Cancer Vaccines and Breast Cancer

Breast cancer is a very common disease, affecting approximately one in nine women in the western world at some time in their lives. In recent years, passive immunotherapy has become an effective adjunct for the treatment of HER2/neu-overexpressing breast cancers. Sometimes, these cancer cells respond well to agents, such as trastuzumab (monoclonal anti-HER-2/neu protein antibody drug). However, this therapy is only effective in a subset of breast cancers, and patients with late-stage disease who are often immune-suppressed are unlikely to respond. Furthermore, tumors can evolve to evade the immune response. Therefore, there is a need for a more globally effective, prophylactic vaccine. To this end, the invention provides an injectable polymer-derived prophylactic HER-2/neu-based breast cancer vaccine.

A strategy in the design of this vaccine was based on manipulating in situ dendritic cell recruitment, activation, and their dispersion to the lymph nodes. Cytosine-guanosine oligonucleotide (CpG-ODN) is used as an adjuvant to help stimulate enhanced responses to the vaccine. This active immunotherapy system stimulates the patient's immune system to promote a HER-2/neu-specific antitumor effect using the body's own immune cells. In addition, the cryogel-vaccine creates a durable antitumor response that, in some cases, protects against tumor recurrence.

To create this cryogel vaccine, both components (adjuvant and cytokine) are incorporated into the cryogel matrix (FIG. 5A). These biomolecules are released in a sustained fashion to recruit and host DCs, and subsequently present cancer antigens from attenuated cells by irradiation as well as danger signals to activate resident naïve DCs and promote their homing to the lymph nodes, which is necessary for a robust anti-cancer immune response. As described in the Examples, this cryogel vaccine system is a promising cell-based immunotherapy approach for the treatment of breast cancer using allogeneic tumor cells. The data presented herein demonstrates that the HER-2/neu-based cryogel vaccine provides potent prophylactic protection against mammary cancer.

Injectable Gelatin Cryogels

The performance of biomaterials-based therapies can be hindered by complications associated with surgical implant, motivating the development of materials systems that allow minimally invasive introduction into the host. Implantable biomaterials have been proposed to locally deliver or recruit cells, or provide sustained release of therapeutic molecules for applications such as tissue engineering, drug delivery, gene therapy, and vaccines. The clinical implantation of prefabricated biomaterials for these purposes typically requires trained physicians, causes patient distress, creates potential scarring, poses a risk of infection, and often causes inflammation at the surgical site that may inhibit the performance of the implant. Thus, there is a need for biomaterials that can be introduced in a minimally invasive manner. Such biomaterials would be of great use in many therapeutic applications.

Injectable hydrogels have been used as biomaterial implants without the need for surgery. Many of these materials systems involve the injection of a polymer solution and subsequent crosslinking of the polymer chains by chemical or physical means to form a solid. However, the use of liquid precursors may result in leakage from the implant site to unwanted tissues and poses difficulties in generating the desired implant geometry. Although injectable hydrogels have been used as biomaterial implants without the need for surgery, many of these injectable hydrogel have certain disadvantages, such leakage from the implant site to unwanted tissues and difficulties in generating the desired implant geometry. Other hydrogels scaffolds are not easily remodeled and/or degraded by cells locally—as such, their ability to integrate with host tissue is limited. Some of these hydrogel scaffolds also require modification of the alginate polymer with cell adhesive peptides in order to allow cell attachment, which requires additional synthesis steps. Thus, the hydrogels of the invention have distinct advantages over previously described injectable hydrogels. This invention provides a preformed hydrogel scaffold with a defined geometry and microstructure that can be introduced to the body in a minimally invasive manner through a conventional needle. See, e.g., WO 2012/149358, incorporated herein by reference. These hydrogels are formed by cryopolymerization of a material such as methacrylated alginate using radical polymerization at sub-zero temperatures. These scaffolds are capable of delivering cells and biomolecules in a non-invasive manner. To allow for cell attachment, these alginate hydrogels are modified with cell adhesive peptides.

The cell-adhesive and degradable gelatin cryogel scaffold that can be injected through a conventional needle while maintaining a predefined geometry and architecture. These gelatin cryogels have certain advantages over other hydrogels or cryogels (such as alginate cryogels). Gelatin is a heterogenous mixture of polypeptides that is derived from collagen by partial hydrolysis. Collagen is an insoluble fibrous protein that occurs in vertebrates and is the main component of connective tissues and bones. For example, the collagen used to make gelatin is isolated from the connective tissues and bones of animals, e.g., from skin and bones. Gelatin is commercially available at a pharmaceutical grade. Exemplary types of gelatin include gelatin derived from porcine skin, beef skin, or bone. For example, gelatin is derived by acid treatment of collagenous material (also called Type A gelatin) or alkali treatment of collagenous material (also called Type B gelatin). Other examples of gelatin include recombinant human gelatin (e.g., available from Fibrogen, Inc., http://www.fibrogen.com/recombinant-gelatin) and low endotoxin gelatin preparation from animal origin is another example of a gelatin (e.g., available from Nitta Gelatin NA Inc., http://nitta-gelatin.com/bematrix-low-endotoxin-gelatin/). In some cases, the cryogels of the invention contain Type A gelatin, such as from porcine skin.

The gelatin used in the cryogels has a molecular weight range of 20,000 to 250,000 g/mol (e.g., 20,000 to 200,000 g/mol, 50,000 to 150,000 g/mol, or 75,000 to 100,000 g/mol). The amino acid composition of gelatin contains about 0.1 to about 0.5% (e.g., about 0.2%) tyrosine and about 10% to about 50% (e.g., about 30%) glycine. For example, gelatin contains 20-35% glycine (e.g., 24-32% glycine), 10-20% proline (e.g., 14-18% proline), 10-20% (e.g., 12-16%) hydroxyproline, 8-15% (e.g., 10-12%) glutamic acid, 5-15% (e.g., 8-12%) and alanine. For example, gelatin is water-soluble. In some embodiments, an elemental makeup of gelatin includes 45-55% (e.g., 50%) carbon, 5-10% (e.g., 7%) hydrogen, 15-20% (e.g., 17%) nitrogen, and 20-30% (e.g., 25%) oxygen.

Gelatin is a material with inherent cell-responsive (e.g., cell binding and enzymatically degradable) elements that can improve the performance of cryogel implants by allowing direct cell attachment and local remodeling. Derived from collagen, gelatin contains inherent peptide sequences that facilitate cell adhesion and enzymatic degradation.

Additionally, its low cost, lack of immunogenicity, and safety record in medicine (e.g., as a hemostatic agent or blood volume expander) makes gelatin an attractive implantable biomaterial. Modification of gelatin with pendant methacrylate groups (GelMA) allows crosslinked hydrogels to be formed using radical polymerization, which have been used extensively in cell culture and tissue engineering studies. In some cases, the gelatin (e.g., Type A gelatin) is methacrylated, i.e., pendant methacrylate groups are added primarily to the free amines of gelatin by reaction with methacrylic anhydride. For example, the methylacrylated gelatin contains a degree of substitution of at least 50%, at least 60%, at least 70%, at least 80%, at least 90% (e.g., about 79%).

The fabrication and characterization of scaffolds formed by cryopolymerization of GelMA (cryoGelMA) are described herein. In particular, the bulk mechanical behavior, structure, and degradation of the cryoGelMA gels, as well as the ability of these scaffolds to facilitate cell attachment, proliferation, and survival were characterized. Additionally, the ability of gelatin cryogels to locally deliver a chemoattractant protein, recruit host cells, and undergo cell-mediated degradation in vivo is also reported herein.

The results presented herein show that porous cryoGelMA gels of a defined shape can be injected through a conventional needle and regain their geometry and architecture after ejection from the needle bore. This is a result of the thin-walled and highly porous structure of these gels imparted through cryopolymerization. Application of a mechanical stress during injection causes rapid efflux of water from the interconnected pores and collapse of the scaffold structure. Removal of stress after injection releases stored elastic energy and causes water influx into the hydrophilic gel, resulting in recovery of the cryogel shape. Previously reported injectable gelatin-based gels have relied on liquid prepolymers that require crosslinking agents to allow in situ gelation. See, e.g., Kuwahara K. et al. Tissue Eng Part C Methods 2010; 16:609-18; and Sakai S. et al. Biomaterials 2009; 30:3371-7. The use of a liquid precursor generally does not allow a defined geometry or microarchitecture to be created in the resulting gel, and prepolymer leakage to unwanted tissues may occur prior to gel formation. CryoGelMA gels of predefined shape and porosity can be implanted in a highly localized manner at any site that can be safely accessed with a needle.

Also, cryoGelMA gels are cell and tissue compatible. CryoGelMA gels allowed cell attachment, spreading, proliferation, and sustained viability of fibroblasts in vitro. In vivo implanted gels produced mild acute inflammation followed by a foreign body response at the scaffold periphery, which is typical of many biomaterials. See, e.g., Mikos A. et al. Adv Drug Deliv Rev 1998; 33:111-39. Nanoporous GelMA hydrogels are compatible in cell culture applications for a variety of mouse and human cell types in 2D and 3D. See, e.g., Nichol J. et al. Biomaterials 2010; 31:5536-44; Benton J. et al. Tissue Eng Part A 2009; 15:3221-30; Qi H. et al. Adv Mater 2010; 22:5276-81; Ramon-Azcón J et al. Lab Chip 2012; 12:2959-69; and Aubin H et al. Biomaterials 2010; 31:6941-51. In addition, cell-laden nanoporous GelMA hydrogels introduced into athymic nude mice elicit minimal inflammation and cell infiltration. See, e.g., Nichol J et al. Biomaterials 2010; 31:5536-44; and Lin R-Z et al. Biomaterials 2013; 34:6785-96. The cell and tissue compatible nature of porous cryoGelMA gels are favorable for applications where cell trafficking within the scaffold is important, such as cell delivery and recruitment.

The results of both in vitro and in vivo degradation studies described herein show that cryoGelMA gels are enzymatically degradable. Collagenase preparations, mammalian MMP-2 and -9 were capable of degrading cryoGelMA gels in vitro, indicating that the enzymatic degradability of gelatin was preserved after modification with methacrylate pendant groups and cryopolymerization. Controlled release of GM-CSF from the scaffold resulted in complete scaffold infiltration by immune cells, increased MMP activity, and accelerated scaffold degradation. These results are consistent with the role of GM-CSF as a mediator of immune cell recruitment, and as an inducer of MMP production. CryoGelMA surprisingly degraded at a slower rate in the presence of collagenase type II in vitro than has been previously reported for nanoporous GelMA hydrogels. See, e.g., Hutson C et al. Tissue Eng Part A 2011; 17:1713-23. Also surprisingly, cryoGelMA degradation in vivo was also substantially slower than reported for other implantable gelatin formulations. See, e.g., Chen Y-C et al. Adv Funct Mater 2012; 22:2027-39; Kang H-W et al. J Bioact Compat Pol 1999; 14:331-43; and Tabata Y et al. J Control Release 1994; 31:189-99. This enhanced stability of cryoGelMA may be due to an overall higher degree of crosslinking and entangled polymer network density achieved with cryopolymerization relative to conventional bulk hydrogel formation. CryoGelMA gels can undergo cell-mediated remodeling at the injection site, alleviating the need for surgical explant in certain applications.

CryoGelMA gels also provide localized controlled release of proteins. For example, cryoGelMA releases GM-CSF in a sustained manner, and subcutaneously injected GM-CSF-cryoGelMA releases bioactive GM-CSF, which causes immune cell recruitment to the scaffold. CryoGelMA allows the encapsulation of proteins in a single step that occurs concurrently with gel formation. This is an advantage over commonly used protein-loaded gelatin hydrogel fabrication schemes that use crosslinking agents that cause protein deactivation during direct encapsulation (e.g., glutaraldehyde). See, e.g., Young S et al. J Control Release 2005; 109:256-74. Using gelatin as the scaffold material allows release of molecules of various net charges based on the processing used for gelatin fabrication and/or through chemical modifications to alter the electrostatic properties of gelatin. Additionally, the tightly packed, entangled, and highly crosslinked polymer network formed by phase separation during cryopolymerization provides an increased physical barrier to protein release relative to conventionally formed hydrogels. Enzymatic degradation of the cryogel walls by recruited host cells facilitates release of entrapped proteins. These properties allow cryoGelMA to provide cell-triggered release of therapeutic proteins at sites of disease.

The gelatin cryogels described herein (e.g., the cryoGelMA) are suitable for use as a cryogel vaccine (e.g., to vaccinate against a cancer or infectious disease) as described in detail herein. For example, the gelatin cryogels are loaded with GM-CSF and CpG-ODN as well as an antigen (e.g., a cancer cell antigen, such as an irradiated or attenuated cancer cell).

The following experimental methods were used to characterize the cryogel vaccines for melanoma described herein.

Materials

UP LVG sodium alginate with high gluronate content was purchased from ProNova Biomedical; 2-morpholinoethane-sulfonic acid (MES), sodium chloride (NaCl), calcium chloride ($CaCl_2$) sodium hydroxide (NaOH), N-hydroxysuccinimide (NHS), 1-ethyl-3-(3-dimethylaminopropyl)-carbodiimide hydrochloride (EDC), 2-aminoethyl methacrylate hydrochloride (AEMA), and acetone were purchased from Sigma-Aldrich. ACRL-PEG-NHS (3.5 kDa) was purchased from JenKen Technology. Rhodamine-labeled polylysine was obtained from Nanocs Inc. Alexa Fluor 488-phalloidin and 4',6-diamidino-2-phenylindole (DAPI) were purchased from Life Technologies. The integrin binding peptide (Gly)4-Arg-Gly-Asp-Ala-Ser-Ser-Lys-Tyr (SEQ ID NO: 1) was custom made by Commonwealth Biotech. Regular B16-F10 cells (ATCC) and GM-CSF transduced B16-F10 cells (kindly provided by the Dranoff's lab at Dana Farber Cancer Institute) were cultured in Dulbecco's modified Eagle medium (DMEM) supplemented with 10% (vol/vol) FBS and 1% (vol/vol) penicillin-streptomycin, all obtained from Invitrogen.

Chemical Modification

MA-alginate was prepared by reacting alginate with AEMA. Sodium alginate (1 g) was dissolved in a buffer solution [0.6% (wt/vol), pH ~6.5] of 100 mM Mes. NHS (1.3 g) and EDC (2.8 g) were added to the mixture to activate the carboxylic acid groups of alginate. After 5 min, AEMA (2.24 g; molar ratio of NHS:EDC:AEMA=1:1.3:1.1) was added to the product and the solution was stirred at RT for 24 h. The mixture was precipitated in acetone, filtered, and dried in a vacuum oven overnight at RT. $^1$H NMR was used to characterize chemical modification of alginate and degree of functionalization of MA-alginate (FIG. 10).

Cryogel Vaccine Fabrication

Macroporous matrices were synthesized by redox-induced free-radical polymerization of MA-alginate in water.

ACRL-PEG-G4RGDASSKY (SEQ ID NO: 2) was synthesized according to Bencherif S et al. Biomaterials. 2008; 29:1739-49, incorporated herein by reference. Alginate cryogel vaccines were synthesized by mixing 23 mg [2.3% (wt/vol)] of MA-alginate macromonomer in deionized water with tetramethylethylenediamine (TEMED) [0.5% (wt/vol)] and ammonium persulfate (APS) [0.25% (wt/vol)]. CpG-ODN 1826, 5'-TCC ATG ACG TTC CTG ACG TT-3' (SEQ ID NO: 3), (Invivogen) and GM-CSF (PeproTech) were added to the polymer solution prior cryopolymerization. Fabrication conditions were chosen to allow the solution to freeze before the gelation takes place. More specifically, the precursor solution was precooled to 4° C. to decrease the rate of polymerization before freezing, and once the initiator was added to the prepolymer solution, the solution was quickly poured into a precooled (−20° C.) Teflon mold. After a complete incubation period of 17 h, the gels were heated to RT to remove ice crystals and washed with deionized water. Cell-adhesive cryogels were synthesized using ACRL-PEG-G4RGDASSKY (SEQ ID NO: 2) as a comonomer [0.8% (wt/vol)] during the polymerization. Conventional hydrogels were cross-linked for 30 min at RT for a homogeneous gelation.

Cell Seeding and Incubation of Cellular Cryogel Vaccines

Before seeding cells, the cryogels were treated with 70% ethanol and washed with PBS. The cryogels were mechanically compressed to partially remove pore water under sterile conditions before cell seeding. Briefly, B16-F10 cells were suspended in complete culture medium (DMEM supplemented with 10% FBS and 1% penicillin-streptomycin). Prior seeding, tumor cells were irradiated by receiving 3500 rads (1 rad=0.01 Gy) from a 137Cs source discharging 208 rads/min for 17 min. Twenty microliters of a cell suspension ($10^7$ cells/mL) were added in a dropwise manner on top of each square-shaped cryogel and the cell-loaded cryogels were cultured in FBS-supplemented media for 6 h (37° C. in 5% $CO_2$ environment). Cell distribution was noted to be homogeneous throughout the gel construct.

Controlled Release of Immunomodulator Factors

To determine the incorporation efficiency and release kinetics of CpG-ODN and GM-CSF from cryogel vaccines, standard release studies were carried out. GM-CSF and CpG-ODN releases in the supernatant were detected by ELISA (Invitrogen) and OliGreen assay (Invitrogen), respectively.

Hydrogel Characterization

Structural analysis of the macroporous gel-vaccine was performed using a LEO 982 scanning electron microscope (SEM) (LEO Electron Microscopy). To prepare the samples, cryogels in the frozen state following cryogelation were lyophilized and sectioned for observation. The average size of pores in cryogels was calculated by averaging the diameters of the pores in the gels observed by SEM. The distribution of cells within the scaffolds was visualized with an inverted laser scanning confocal microscope (Leica SP5 XMP, Germany). High-resolution image stacks were collected with 300-nm separation between slices (z-stacks) for the 3D reconstruction of the entire scaffold and visualization of cell-matrix interactions.

Generation of Bone Marrow-Derived DC (BMDC) and In Vitro DC Activation Assays

BMDC from bone marrow progenitors were generated by the following protocol. Murine bones were placed in 70% ethanol for 2 min and subsequently washed in PBS. Both bone ends were cut off, and the marrow was flushed out with RPMI 1640 medium (Gibco, Grand Island, N.Y.). The red cells were lysed with ammonium chloride (0.45 M). The cells were centrifuged for 10 min at 1,500 rpm and $2 \times 10^5$/ml cells were cultured for 10 d in Petri dishes in 10 ml of complete medium (RPMI 1640 medium supplemented with 10% FBS, 1% penicillin-streptomycin, 2 mM L-glutamine, $5 \times 10^{-5}$ M 2-mercaptoethanol, and 15%-30% of mouse GM-CSF). To evaluate viability and activation induction of BMDC from CpG-ODN loaded cryogel vaccines, two square-shaped blank scaffolds or scaffolds containing CpG-ODN (5'-TCC ATG AGC TTC CTG AGC TT-3') (SEQ ID NO: 4) were incubated with bone morrow DC in complete culture medium for 1 d (RPMI 1640 medium supplemented with 10% FBS and 1% penicillin-streptomycin). A live/dead assay was performed to evaluate BMDC viability in the presence of cryogels. Briefly, isolated BMDC in triplicate were incubated with the live/dead assay dye solution (Molecular Probes) containing 0.5 µL of calcein-AM and 2 µL of ethidium homodimer-1 in 1 mL of PBS. After 30 min incubation, the cells were rinsed with PBS, and cell viability was quantified by flow cytometry (FACS). Yield evaluation and induced BMDC maturation was quantified and tested by FACS, respectively. The following antibodies conjugated to fluorescent markers (Proimmune) were used for surface stainings: MHC II (2 G9/PE), CD86 (B7-2, GL1, rat IgG2a), CD11c (N418, hamster IgG). For purified antibodies, the appropriate anti-TNP isotype controls were used. The IL-12 concentration in the cell-culture supernatant was then analyzed with ELISA (R&D systems), according to the manufacturer's instructions.

Minimally Invasive Delivery of Cryogel Cancer Vaccines and Cell Recruitment

Female C57BL/6J mice (n=10; The Jackson Laboratory), 4-6 wk of age, were anesthetized with 2.5% isoflurane using an inhalation anesthesia system (E-Z Anesthesia; Euthanex). Each mouse received a 2 s.c. dorsal injections of cryogel vaccines suspended in 0.2 mL of PBS by means of a 16-gauge needle under the dorsal panniculus carnosus. To visualize the cell-recruitment and homing capacity of cryogels, mice were sacrificed, and the explanted scaffolds were embedded in paraffin and 5 µm sections were stained with hematoxylin and eosin (H&E) for histological analysis. To quantify dendritic cell recruitment, explanted cryogels were digested in collagenase type II (250 U/ml; Worthington) that was agitated at 37° C. for 45 min. The cell suspensions were then poured through a 40 mm cell strainer to isolate cells from scaffold particles, and the cells were pelleted and washed with cold PBS and counted with a Z2 coulter counter (Beckman Coulter). To assess DC infiltration, cells isolated from alginate sponges were then stained with primary antibodies (Proimmune) conjugated to fluorescent markers to allow for analysis by flow cytometry. Allophycocyanin (APC)-conjugated CD11c and APC-conjugated CD11c stains were conducted for DC infiltration analysis Animal work was performed under a protocol approved by the Harvard Standing Committee on Animals in compliance with the National Institutes of Health guidelines.

In Situ Identification of DC Subsets and T Cells

Blank alginate sponges and sponges containing 1.5 µg of GM-CSF in combination with 100 µg of CpG-ODN were injected into subcutaneous pockets on the back of 6- to 9-week-old male C57BL/6J mice. To analyze DC recruitment, scaffolds were excised at various time points and digested the ingrown tissue into single-cell suspensions with a collagenase type II solution (250 U/ml; Worthington) that was agitated at 37° C. for 45 min. The cell suspensions were then poured through a 40 mm cell strainer to isolate cells from scaffold particles, and the cells were pelleted and washed with cold PBS and counted with a Z2 coulter counter (Beckman Coulter). To assess DC infiltration and activation, subsets of the total cell population isolated from alginate sponges were stained with primary antibodies (Proimmune) conjugated to fluorescent markers to allow for analysis by flow cytometry. Allophycocyanin (APC)-conjugated CD11c (DC marker) and phycoerythrin (PE)-conjugated CD86 (B7, costimulatory molecule) stains were conducted for DC recruitment analysis, and APC-conjugated CD11c, and PE-conjugated MHCII stains were conducted for DC programming analysis. To further delineate the presence of specific DC subsets, cells were stained with APC-conjugated CD11c and PE-conjugated PDCA-1 (pDC marker), APC-conjugated CD11c and PE-conjugated CD8 (CD8 DC), or APC-conjugated CD11c and FITC-conjugated CD11b (CD11b DC). To assess T cell infiltration, PE-Cy7-conjugated CD3 stains were performed in conjunction with APC-conjugated CD8a (CD8 T cells), FITC-conjugated CD4 (CD4 T cells), and PE-conjugated FoxP3 (Treg) and analyzed with flow cytometry. Cells were gated according to positive FITC, APC, and PE with isotype controls, and the percentage of cells staining positive for each surface antigen was recorded. To determine the cytokines (IL-12, IFN-γ, etc) concentration at the cryogel vaccine site, adjacent tissue was excised and digested with tissue protein extraction reagent (Pierce). Several cytokines concentrations in the tissue were then analyzed with a Bio-Plex Pro Mouse Cytokines 23-plex Assay, according to the manufacturer's instructions.

Prophylactic Immunization, Long-Term Protection, and Toxicology

Two square-shaped RGD-containing alginate sponges pre-cultured with irradiated melanoma tumor cells and each loaded with GM-CSF (1.5 ug/scaffold) and CpG-ODN (50 ug/scaffold) were injected subcutaneously into each sides of the lower flank of C57BL/6J mice (n=10/group). For control groups, mice were also injected with blank cell-seeded alginate sponges as well as sponges loaded with one single immunomodulator factor, either GM-CSF or CpG-ODN. Additionally, cryogel cancer vaccines were compared with a common cell-based vaccine. Therefore, a group of mice were vaccinated with $5 \times 10^5$ irradiated (3500 rads) GM-CSF-transduced B16-F10 cells, as described previously. See Dranoff G et al. Proc. Natl. Acad. Sci. USA. 1993; 90:3539-43; and Dranoff G. Immunol. Rev. 2002; 188:147-54, incorporated herein by reference. Animals were challenged 6 days later with a subcutaneous injection of $1 \times 10^5$ B16-F10 melanoma cells in the back of the neck. To assess long-term immunological response to melanoma vaccines, surviving mice in each group (n>3) were tumor rechallenged following 126 days post first tumor challenge with $1 \times 10^5$ B16-F10 melanoma cells. Animals were monitored for the onset of tumor growth (approximately 1 mm³) and sacrificed when challenge tumors reached 20 mm (longest diameter) or severe ulceration or bleeding developed. Following 18 months after initial tumor challenge, several surviving immunized mice from successive tumor inoculations (day 6 and day 96 post vaccination) were euthanized. Tissues from the major organs (heart, liver, spleen, lungs, kidney, brain, lymph nodes, pancreas, small intestine, colon, stomach) and explanted implants were fixed in a 10% neutral buffered formalin solution, resuspended in 70% ethanol and sent to Mass Histology Service (Worcester, Mass.) for toxicology study.

Statistical Analysis

All values in the present study were expressed as mean±1 SD unless otherwise noted. The significant differences between the groups were analyzed by a Student's t-test, ANOVA, and log rank test. Differences were considered significant at $P<0.05$.

The following experimental methods were used to characterize the gelatin cryogels described herein.

Mice

C57BL/6J and C57BL/6J-Tyr$^{c-2J}$ mice (female, aged 6-8 weeks; Jackson Laboratories) were used in the experiments described herein.

Methacrylated Gelatin Synthesis

Methacrylated gelatin (GelMA) was synthesized (FIG. 26A) by allowing Type A porcine skin gelatin (Sigma) at 10% (w/v) to dissolve in stirred Dulbecco's phosphate buffered saline (DPBS; GIBCO) at 50° C. for 1 h. Methacrylic anhydride (Sigma) was added dropwise to a final volume ratio of 1:4 methacrylic anhydride:gelatin solution. This resulted in GelMA with a degree of substitution of 79% (FIG. 27). The solution was stirred at 50° C. for 1 h, and then diluted 5× with DPBS. The resulting mixture was dialyzed in 12-14 kDa molecular weight cutoff tubing (Spectrum Labs) for 4 d against distilled water (dH$_2$O) with frequent water replacement. The dialyzed solution was lyophilized, and the resulting GelMA was stored at −20° C. until use. Rhodamine-labeled GelMA, created from the reaction of GelMA with NHS-rhodamine (Thermo Scientific), was purified using an identical dialysis and lyophilization process.

Gelatin Cryogel Preparation

Cryogels were formed by dissolving GelMA in dH$_2$O to the final desired concentration in the presence of 0.5% (w/v) ammonium persulfate (APS; Bio-Rad) and 0.1% (w/v) tetramethylethylenediamine (TEMED; Bio-Rad). This pre-polymer solution was pipetted into cylindrical (5 mm diameter, 2 mm thickness) polystyrene molds and placed in a freezer set to −12° C. (FIG. 26B). Cryopolymerization was allowed to proceed for 18 h, and the resulting cryogels were thawed and hydrated in dH$_2$O prior to use.

Interconnected Porosity

To test for cryogels for interconnected porosity, scaffolds were first thawed and hydrated for 1 d. Hydrated scaffolds were weighed on a scale, and a Kimwipe was lightly applied to the scaffold surface for 30 s to wick away loosely held water, and the mass was again recorded. The interconnected volume was calculated as the mass of water wicked away divided by the total hydrated mass.

Scanning Electron Microscopy

For scanning electron microscopy, cryogels were serially transitioned from dH$_2$O into absolute ethanol with 20 min incubations in 30, 50, 70, 90, and 100% ethanol solutions. Samples were incubated in hexamethyldisilazane (Electron Microscopy Sciences) for 10 min and dried in a desiccator for 1 h. Dried cryogels were adhered onto sample stubs using carbon tape and coated with a platinum/palladium in a sputter coater. Samples were imaged using secondary electron detection on a Carl Zeiss Supra 55 VP field emission scanning electron microscope (SEM). Cell-laden cryogels were fixed in 4% paraformaldehyde (PFA) and prepared for SEM as described above. Images were false-colored in Adobe Photoshop CS6 to highlight cells.

2-Photon Microscopy

To characterize the hydrated cryogel structure, rhodamine-GelMA cryogels were placed in dH$_2$O in a 35 mm glass-bottom culture plate (MatTek), and imaged on a Leica SP5 inverted laser scanning confocal microscope. 2-photon excitation was achieved using a Chameleon Vision 2 pulsed infrared (IR) laser (Coherent) at 820 nm, and fluorescence emission was collected through a 565-605 nm bandpass filter by a non-descanned detector. For imaging of cell-laden cryogels, cells were first labeled with 5-chloromethylfluorescein diacetate (CMFDA) according to the manufacturer's instructions (Molecular Probes) prior to seeding on scaffolds. After cell attachment, cells were fixed with 4% PFA in DPBS, and cell nuclei were stained with Hoescht 3342 (Molecular Probes). For 3-color imaging of cell-laden rhodamine-cryoGelMA scaffolds, the IR laser was tuned to 800 nm and Hoescht 3342, CMFDA, and rhodamine-GelMA were detected through 430-480 nm, 500-550 nm, and 565-605 nm bandpass filters, respectively.

Bulk Cryogel Imaging

Bright field and fluorescence images of bulk cryogels were acquired using a Zeiss Axio Zoom V16 stereomicroscope. To capture high-speed cryogel injection videos, a Hamamatsu Orca-Flash 4.0 sCMOS camera was used at 200 frames per second.

Cells and Cryogel Seeding

NIH 3T3 cells were cultured in Dulbecco's Modified Eagles Medium (DMEM) with 10% (v/v) fetal calf serum, 100 U/ml penicillin, and 100 µg/ml streptomycin (Gibco) at 37° C. in a 5% CO2 atmosphere. Prior to seeding into cryogels, cells were harvested using a non-enzymatic cell dissociation solution (Sigma) and resuspended at $10^7$ cells/ml in complete medium. Cryogels were dehydrated by wicking with a Kimwipe, and rehydrated in 100 µl of cell suspension in a 2 ml round-bottom centrifuge tube. Tubes were incubated at 37° C. for 45 min to allow for cell attachment. Gels were placed directly in complete medium following incubation, and cultured on an orbital shaker at 80 rpm.

In Vitro Cell Viability

To assess viability, cells were retrieved after culture on cryogels using 0.05% trypsin/EDTA at 37° C. for 45 min Scaffolds were mechanically disrupted with a pipette, and filtered through a 70 µm cell strainer. Cells were stained using the Muse Count and Viability Assay Kit and analyzed using a Muse Cell Analyzer (EMD Millipore). To assess metabolic activity, cryogels were transferred to new wells with 10% AlamarBlue (AbD Serotec) in cell culture medium and incubated for 6 h. The reduction of the substrate was assessed as described in the manufacturer's instructions.

Cryosection Preparation and Staining

Prior to freezing and sectioning, samples were fixed in 4% PFA in DPBS at room temperature for 20 min. The gels were washed three times in DPBS and placed in a 30% (w/v) sucrose in DPBS solution overnight at 4° C. Cryogels were then incubated at room temperature in a 15% (w/v) sucrose+ 50% OCT compound (Tissue-Tek) for 4 h, and then neat OCT for 4 h. Gels were frozen in OCT on dry ice. The frozen blocks were sectioned at −20° C. into 20 µm sections on a Leica CM1950 cryostat. F-actin was stained using Alexa Fluor 488 phalloidin (Molecular Probes). Samples were mounted in Prolong Gold Antifade Reagent with DAPI (Molecular Probes), coverslipped, and imaged on a Zeiss LSM 710 upright confocal microscope. To visualize proliferation within the cryogels, cells were pulsed with 5-ethynyl-2'-deoxyuridine (EdU; Molecular Probes) for 6 h, fixed, cryosectioned, and stained according to the manufacturer's instructions.

Gelatin Zymography

Zymography was performed using a 10% polyacrylamide gel, containing 0.1% (w/v) gelatin or GelMA using standard protocols. Recombinant human (Chemicon) and murine (R&D Systems) pro-MMP-2 and -9 were used to assess GelMA zymogram degradability. For zymography of in vivo implant sites, scaffolds were mechanically disrupted using a 20 G needle in 300 µl of lysis buffer composed of 0.025 M Tris-HCl, pH 7.5, 0.1 M NaCl, 1% v/v IGEPAL CA-630, 10 µg/ml aprotinin, 2 µg/ml leupeptin, and 4 mM benzamidine (Sigma). Samples were vortexed briefly, incubated for 30 min on ice, and centrifuged at 16 000×g to remove debris. The protein content of the resulting lysate was quantified using a bicinchoninic acid assay (Thermo Scientific), and samples were diluted to an equal protein concentration prior to loading for zymography.

In Vitro Cryogel Degradation

Cryogels created using rhodamine-GelMA were incubated with 25 U/ml collagenase type II (Worthington) in DPBS and were placed on an orbital shaker at 80 rpm and 37° C. The collagenase solution was collected periodically and completely replaced with fresh enzyme solution. Fluorescence of the supernatants with excitation at 550 nm and emission at 580 nm were compared to a standard curve of rhodamine-GelMA also prepared in collagenase. To test the degradability of cryogels by mammalian enzymes, rhodamine-cryoGelMA gels were treated with recombinant murine and human MMP-2 and -9. Recombinant proenzymes were activated with 2.5 mM p-aminophenylmercuric acetate (Calbiochem) in zymogram development buffer for 3 h at 37° C., and each gel was incubated in 100 µl of buffer containing 1 µg of enzyme for a subsequent 18 h. Fluorescence signal from the supernatants was measured on a plate reader, and normalized to fluorescence signal from gels incubated in zymogram development buffer only.

In Vivo Imaging

In vivo imaging studies were performed using an IVIS Spectrum system (PerkinElmer). Living Image 4.0 (PerkinElmer) software was used for quantitative analysis of all images. Cryogels were injected subcutaneously into mice using a 1 ml syringe equipped with a 16 G needle in 200 µl DPBS. To monitor gel degradation in vivo, rhodamine-GelMA was injected subcutaneously in the flank of C57BL/6J-Tyr$^{c-2J}$ mice and fluorescence signal was monitored longitudinally with excitation and emission measured at 570 nm and 620 nm, respectively. The opposite flank was injected with an unlabeled cryogel, and the fluorescence signal from this site was subtracted to correct for baseline.

To visualize local MMP activity at the cryogel site, mice were maintained for two weeks prior to imaging on an alfalfa-free purified rodent diet (Harlan) in order to reduce food autofluorescence. Next, mice were injected with rhodamine-labeled cryogels, and injected intravenously with MMPSense 750 FAST 1 w later. 6 h post-injection, fluorescence signal was measured at 745 nm excitation and 800 nm emission. Baseline fluorescence signal at the scaffold site prior to MMPSense 750 FAST injection was subtracted for quantitative analysis.

Histology of Injected Cryogels

Cryogels injected in C57BL/6J mice were retrieved along with the surrounding 1×1 cm skin samples and fixed overnight in 10% neutral buffered formalin. Samples were embedded in paraffin and sectioned at 7 µm thickness by the Harvard Rodent Histopathology Core. Hematoxylin and eosin (H&E) staining was performed to assess inflammation and cell recruitment at the implant site.

GM-CSF Release

5 µg of recombinant murine granulocyte macrophage colony-stimulating factor (GM-CSF) (Peprotech) was incorporated per cryogel by direct encapsulation prior to polymerization. Gels were retrieved while frozen and placed in 1% BSA fraction V (Roche) in DPBS and placed on an orbital shaker at 80 rpm. The complete supernatant was recovered periodically and frozen until it was analyzed using a murine GM-CSF ELISA (R&D Systems). The amount of GM-CSF in the supernatant of the thawing solution after 1 h was considered unencapsulated and was used to calculate the encapsulation efficiency.

Quantification of In Vivo Cell Recruitment

Blank and GM-CSF-releasing gelatin cryogels were thawed and hydrated for 1 h prior to injection. After the desired implantation period, scaffolds were retrieved and digested in 250 U/ml type II collagenase in DPBS for 45 min at 37° C., and counted using a Muse Cell Analyzer.

$^1$H-NMR

GelMA and control dialyzed gelatin were dissolved in deuterium oxide ($D_2O$; Sigma) at 15% (w/v) at 80° C. $^1$H-NMR spectra with samples equilibrated at 60° C. on a 600 MHz NMR spectrometer (Varian). Data were Fourier transformed, baseline corrected, and referenced to $D_2O$. To calculate the degree of substitution, the integral of the peaks corresponding to the methylene protons of the methacrylate groups were compared to the integral of the aromatic side chain protons, as previously described. See, e.g., Nichol J W. Biomaterials 2010; 31:5536-44.

Mechanical Testing

Cryogel samples were hydrated for one day prior to mechanical testing. Samples were compressed at a rate of 1 mm/min on an Instron 3342 mechanical tester equipped with a 50 N load cell. The Young's modulus was calculated from the linear region of the resulting stress-strain curve between 0-5% strain. Fracture was identified as an abrupt disruption in the rate of increase of stress with strain.

Live Dead Imaging

Cells on cryogels were stained with a Live/Dead kit (Molecular Probes) to assess viability. Media was removed from the culture wells, and gels were washed with DPBS. DPBS containing 2 μm calcein AM and 4 μm ethidium homodimer-1 was added to the wells and a 20 min incubation was performed at 37° C. Scaffolds were imaged on a Zeiss Axio Zoom V16 stereomicroscope.

BrDU Incorporation Assay

Cryogel cell cultures were pulsed with 30 μM bromodeoxyuridine (BrDU) for 4 h. Cells were retrieved using trypsin, fixed and permeabilized with Cytofix/Cytoperm (BD Biosciences), additionally permeabilized with 0.5% Triton X-100, treated with DNAse (1 μg/$10^6$ cells), stained with anti-BrDU APC antibody (BU20A; eBioscience), and analyzed by flow cytometry using a BD LSRFortessa cell analyzer.

The invention will be further described in the following examples, which do not limit the scope of the invention described in the claims.

Example 1

Injectable Biodegradable Preformed Macroscopic Geometric Gels

The compositions and methods described herein provide hydrogels for minimally invasive delivery of shape memory scaffolds for in vivo applications. This method has demonstrated highly efficient and reproducible fabrication of injectable shape-defined macroporous scaffolds. Although only one type of covalently alginate-based crosslinked gel system was evaluated herein, the material performance is readily manipulated by altering its composition, formulation, and degradation profile. The formation of specific shapes and structural stability are desirable characteristics for shape-defined materials, and the most important requirement of these types of materials for minimally invasive therapies is the ability to collapse and faithfully reform the scaffold's structure in a stimulus-responsive manner. A combination of mechanical compression and dehydration is sufficient to compress the scaffolds developed in this work, allowing minimally invasive delivery through a conventional-gauge needle.

Figure 1:
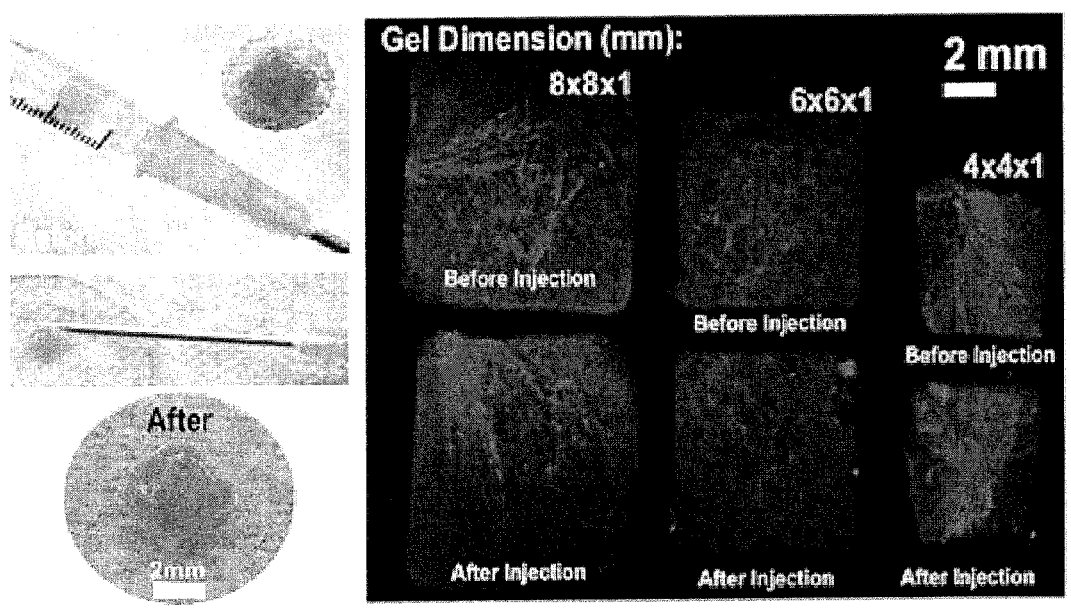
FIG. 1 is a series of four photomicrographs showing injectable alginate-based hydrogel systems. Rhodamine-labeled 1% methacrylated (MA)-alginate gels with various sizes and shapes (disc, cylinders, squares, etc.) were prepared by cryogenic polymerization. Square shape injectable scaffolds are shown. Fluorescent macroscopic gels suspended in 0.2 mL of phosphate buffered saline (PBS) were injected via 16-gauge diameter needles with a complete geometric restoration as illustrated in the microscopy image before and after injection.

These results described herein demonstrated that shape-defined macroporous alginate-based scaffolds were prepared with different geometric sizes and shapes, and successfully passed through a surgical needle without mechanical fracture, and all scaffolds regained their three-dimensional shape immediately (<1s) after rehydration (FIG. 1). The fabrication method is capable to manufacture biocompatible, biodegradable and complicated macroporous tissue scaffolds efficiently and economically. In addition to the application described herein, shape memory scaffolds are especially useful in applications in which large, structurally defined implants are required.

Example 2

Structural Integrity of Injectable Macroscopic Shape-Defined Gels

The deformation of conventional (nanoporous) and macroporous 1% MA-alginate gels under mechanical compression associated with shear forces was examined. Subject to mechanical compression, the gels experience a body of force, which results in a shape change. The influence of the macropores on the gel mechanical properties was also evaluated since the stiffness of the scaffold dictate the extent of the deformation under an applied shear force. Conventional gels give a Young's modulus (i.e., the slope of the initial part of the stress vs. strain curves in FIG. 2) of 42±4 kPa in compression test. However, macroporous gels led to a dramatic reduction in the modulus to 4±2 kPa. As shown in FIG. 2, cylindrical (4 mm diameter×8 mm height) nanoporous gels reduced their heights by ~16% when subjected to a vertical load before mechanical fracture. In comparison, cylindrical macroporous gels give much larger deformation under lower mechanical stress, due to its lower modulus. Macroporous scaffolds attained 90% or more of compression strain without mechanical fracture, demonstrating their ability to maintain their structural integrity after compression, compaction, and minimally invasive delivery. Also, these results confirmed that the scaffolds displayed shape memory in vitro.

In the hydrogels described herein, the large volume change of the macroporous shape-defined gels was caused by reversible collapse of the interconnected pores. The collapsing pores force water contained in the macropores to flow out of the gel. Gel deformation and water convection enhances water transport in and out of the gel. Once the mechanical load is removed, the elastically deformed gel immediately returns to its original, undeformed shape-defined configuration in less than 1 s, as surrounding water was reabsorbed into the gel.

Example 3

Shape Memory Injectable Scaffolds as a Controlled Drug Delivery Carrier

Covalently crosslinked alginate scaffolds possessing shape memory properties were successfully used as a drug delivery system in vivo. The gels having a predefined size and structure were able to exceptionally maintain their structural features after minimally invasive subcutaneously insertion in mice. Suspended gels in PBS were spontaneously hydrated with full geometric restoration after one single injection per site on the lower back of mice. Injected animals did not demonstrate abnormalities in feeding, grooming, or behavior during the time frame of the experiment, nor did they exhibit signs of distress.

Figure 3:
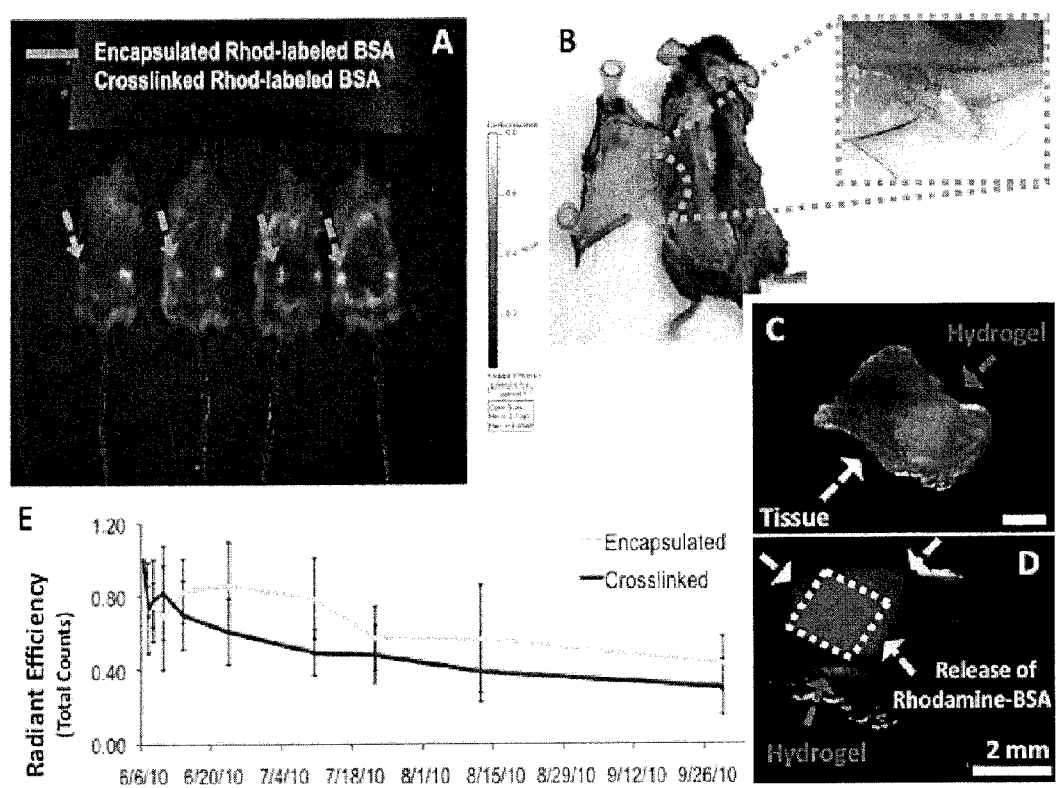
FIG. 3A is a fluorescence photograph showing minimally invasive subcutaneous injection of macroporous scaffolds into the lower back of mice.
FIG. 3B is a photograph showing hydrogel localization after subcutaneous injection of preformed rhodamine-labeled 1% MA-alginate gels (4 mm×4 mm×1 mm) in the subcutis of a mouse after 3 days.
FIG. 3C is a photograph showing merged phase-contrast and fluorescence of a subcutaneously injected rhodamine-labeled alginate macroporous scaffold with restoration of geometry after placement.
FIG. 3D is a photograph of a subcutaneously injected rhodamine-labeled alginate macroporous scaffold with restoration of geometry. Dashed lines denote square-shaped geometry restoration of inserted shape-defined scaffolds.
FIG. 3E is a line graph showing in vivo sustained release profiles of crosslinked (chemically anchored) or encapsulated (physically entrapped) rhodamine-labeled bovine serum albumin (BSA) to injected cryogels. Upon dissection 3 days post-injection, rhodamine-labeled gels recovered their square shape features, had soft consistencies, and were integrated into the surrounding tissues. Values represent mean and standard deviation (n=4).

The hydrogels maintained their hydrogel shape integrity at the site of injection. Animal studies performed to examine the integration of the spongy-like gels with the host tissue showed that the alginate-based scaffolds were biocompatible and did not elicit an immune response or rejection when injected in mice. After 3 days post-injection, rhodamine-labeled scaffolds were surgically removed from mice and analyzed. As shown in FIG. 3B, the scaffold guided in vivo tissue formation around the scaffold indicating the scaffolds could support tissue growth and integration. Furthermore, fluorescent microscopy used to visualize the rhodamine-labeled scaffold, noticeably displayed the original geometry, structural integrity, square-defined shape retention of the gels in vivo (FIG. 3C).

Rhodamine-labeled BSA was also used as a drug delivery model. By providing a drug depot at the site of injection, such devices achieve high local drug concentrations without significant systemic administration. Sustained release of BSA was achieved from the injected square-defined scaffolds as shown in FIG. 3D. Targeted and controlled delivery of rhodamine-labeled BSA in mice was quantified via real-time non-invasive live imaging (FIG. 3A). Exemplary compound, BSA, was either physically entrapped or chemically grafted to the scaffold during the cryopolymerization process. As illustrated in FIG. 3E, sustained controlled release of BSA was achieved over of period of 4 months. Surprisingly, the release profiles for both types of BSA were similar indicating that the release is mainly mediated by matrix degradation over protein diffusion.

Example 4

Cryogel Compositions Enhance Survivability and Limit Migration of Injected Cells In Vivo One application for the compositions and methods described herein is the non-invasive method of cell injection based on cell-scaffold integration. Cell transplantation is a therapeutic option for patients with impaired regional or global function due to cell death. However, the limited number of transplantation methods of cells is considered a major factor limiting the efficacy of cell therapies. As cell and bioactive molecule carriers, injectable preformed scaffolds offer the possibility of homogeneously distributing cells and molecular signals throughout the scaffold. Moreover, the scaffolds are injected directly into tissues or cavities, e.g., muscle, bone, skin, fat, organs, even of irregular shape and size, in a minimally invasive manner. The compositions and methods described herein offer significant advantages such as injectability and efficient cell encapsulation post-polymerization while allowing sufficient mechanical strength to withstand biomechanical loading and providing temporary support for the cells.

Figure 4:
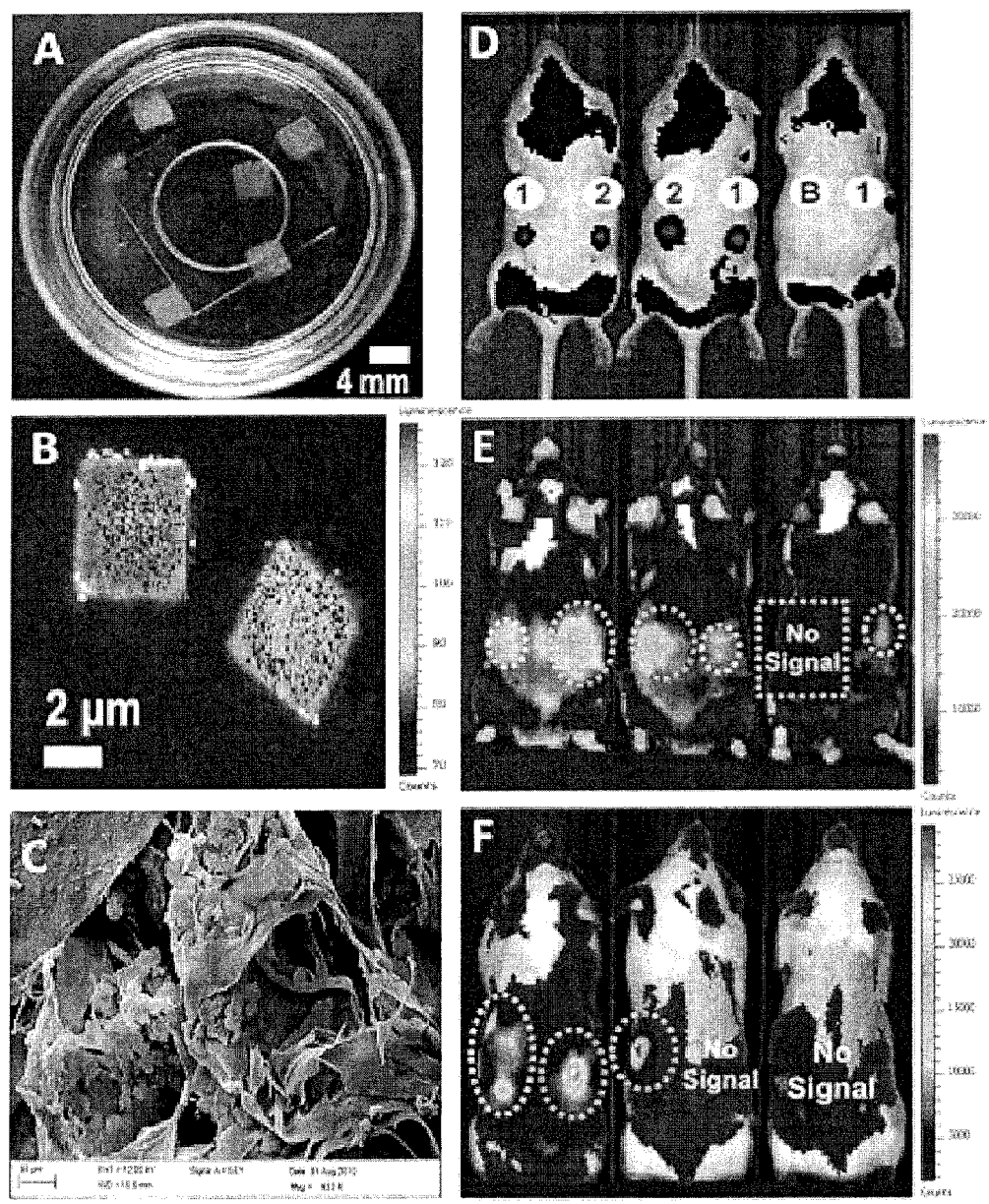
FIGS. 4A-F are a series of photographs showing that injectable pre-seeded scaffolds promote in situ localization of bioluminescent B16 cells.

Square-shaped rhodamine-labeled RGD-containing alginate cryogels (4×4×1; units: mm) were prepared, purified, sterilized, and subsequently seeded with bioluminescent B16 cells, and maintained in culture for 6 hr in cell culture medium before animal subcutaneous injection to promote cell-scaffold integration (FIGS. 4A, 4B, and 4C). Large interconnected pores significantly enhanced cell seeding and distribution, while maintaining relatively high seeding efficiencies (>50%) and viability (>95%). To image bioluminescence of seeded B16 melanoma cells in vitro, 0.15 mg/g of luciferin was added on top of the gel, which freely diffused through the gel network, staining the cells and indicating homogeneous infiltration and depth viability of cells throughout the 3-D construct (FIG. 4B). This is due to the effective nutrient delivery into and waste removal from the inner regions of the scaffold. SEM images confirmed a homogeneous distribution and engraftment of cells within the scaffold (FIG. 4C).

A unique characteristic of these cell/scaffold constructs is that when an appropriate shear stress is applied, the deformable hydrogel is dramatically and reversibly compressed (up to 90% of its volume) resulting in injectable macroporous preformed scaffolds. This property allows gel/cell constructs to be delivered via syringe with high precision to target sites. Homogenous cellular distribution and cell viability are unaffected by the shear thinning process and gel/cell constructs stay fixed at the point of introduction, suggesting that these gels are useful for the delivery of cells to target biological sites in tissue regeneration efforts.

Subsequently, healthy C57BL/6 mice received a subcutaneous injection on their backs of 200×10$^3$ B16's integrated into alginate macroporous scaffolds. The resulting injected gels were delivered to a targeted site where they quickly recovered to their original mechanical rigidity with location permanency. As shown in FIG. 4D, cell-loaded rhodamine-labeled alginate scaffolds were syringe-delivered (1 cc, 16 G) with high precision in the back of mice and visualized by in vivo optical live imaging. Integration of melanoma B16 cells to RGD-modified alginate cryogel scaffolds and their injections into healthy mice was investigated to demonstrate successful syringe-delivery and function of pre-cultured cells while promoting homing, survival, and engraftment of tumorigenic cells. The results presented herein demonstrate that the designed tissue-engineered scaffolds mimic the natural environment where cells normally reside, and as a result tumors are formed after every injection of tumorigenic cell-embedded matrix in healthy BALB/c mice. The inoculation of melanoma cells subcutaneously was monitored via real-time non-invasive live imaging (FIG. 4D). The incidence of tumor formation and tumor growth was examined over a period of 9 days. The success of the melanoma B16 tumor model is clearly evident as shown in FIGS. 4D-4E. As an in vivo model, the cell/scaffold construct has fulfilled several criteria: successful syringe-delivery with precision to a target site and cell survival in their current local environment resulting in tumor formation.

As described herein rhodamine-labeled (1) and rhodamine-labeled RGD-modified (2) cell-seeded alginate cryogels were administered in mice to study the effect of cell-engraftment in cell transplantation and homing. As a control, a bolus of free cells (B) was also injected. Rhodamine-labeled scaffolds were successfully injected subcutaneously as shown in FIG. 4D. Except for the bolus injection site, red-emitting rhodamine dyes show intense fluorescent red spots in each side of the mice's back indicating in vivo localization of cell-seeded scaffolds. After 2 days post-injection, bioluminescence of cell-seeded scaffolds was measured 30 min after intraperitoneal injection of luciferin. As shown in FIG. 4E, bioluminescence for injected RGD-modified cell-seeded gels was particularly brighter when compared to the plain scaffolds showing the necessity to incorporate RGD to the polymeric network to support cell-engraftment and thus efficient cell transplantation. For the injection of the cellular bolus, the absence of bioluminescence suggests minimal cell retention at the injection site, rapid cell migration, and likely limited cell transplants survival. Similarly, 9 days post-injection, bioluminescence of cell-seeded scaffolds was mainly apparent for RGD-modified scaffolds confirming the developed non-invasive method for cell injection based on cell-scaffold integration is crucial to decrease migration, promote homing, enhance survivability, and engraftment of cells in vivo (FIG. 4F).

Decreasing the rapid cell death that occurs within a few days after transplantation of graft cells is of great relevance for the success of cell transplantation therapies. The results presented herein confirm that the incorporation of the cell-adhesive peptide plays a key role in regulating interactions between cells and the scaffold and cell-fate. These gels are also suitable for use as a delivery system for the sustained delivery of proteins (e.g., growth factors) involved in cell differentiation and maturation (FIG. 3E). This technique is also a tool for enhancing stem cell survival in vivo.

Example 5

Injectable Biodegradable Cryogels for Immunotherapy Applications

A minimally invasive scaffold-based active vaccine containing host pathogens was developed for the therapeutic treatment of cancer. In the case of cancer, the immune system needs an external boost from immunotherapies to be able to become more effective in fighting cancer. The active immunotherapy system described herein was designed to stimulate the patient's immune system, with the objective of promoting an antigen-specific antitumor effect using the body's own immune cells. In addition, the cryogel-vaccine leads to a durable antitumor response that protects tumor recurrence. Dendritic cells (DCs) are antigen-presenting cells critically involved in regulating the immune system. The vaccine mediates in situ manipulation of dendritic cell recruitment, activation, and their dispersion to the lymph nodes. Cytosine-guanosine oligonucleotide (CpG-ODN) was used as an adjuvant further stimulate responses to the vaccine.

As shown in FIG. 5A, both components (adjuvant and cytokine) can be easily incorporated into the cryogel matrix and released in a sustained fashion to recruit and host DCs, and subsequently present cancer antigens from the irradiated cells (or other cell-associated antigens) and danger signals to activate resident naïve DCs and promote their homing to the lymph nodes, which is necessary for a robust anti-cancer immune response. Specific and protective anti-tumor immunity was generated with our minimally invasive alginate-based active vaccine, as 80% survival was achieved in animals that otherwise die from cancer within a couple of months. The data using the cryogel-based prophylactic vaccine for melanoma was shown to induce a very strong immunologic memory, as 100% survival was achieved in the rechallenged animals following 100 days post vaccination.

Different tumor cell-associated antigens are used in the cellular cryogel-based vaccine platform, thereby permitting treatment or prophylaxis for a variety of cancers. Active specific immunotherapy involves the priming of the immune system in order to generate a T-cell response against tumor-associated antigens. One example of the active specific approach is adoptive T-cell therapy, which involves the ex vivo cultivation of T cells with demonstrated activity against a specific target cancer antigen. Cells are obtained from the subject, purified, and cultured. Such ex vivo cultivation increases the frequency of these T cells to achieve therapeutic levels. The cells are then infused back into the patient via injectable alginate-based cryogel.

Creating an infection-mimicking microenvironment by appropriately presenting exogenous cytokines (e.g., GM-CSF) and danger signals (e.g., CpG-ODN), in concert with cancer antigen provides a means to precisely control the number and timing of DC trafficking and activation, in situ. At different time points post scaffold-based vaccine injection (vax C), cells were isolated from the cryogels and surrounding tissues, spleen, and lymph nodes (LN) for cell counting and fluorescence-activated cell sorting (FACS) analysis to determine the overall number of cells and percentage of DCs (CD11c+ cells) and T cells (CD3+ cells). Cells infiltrating the vaccine site and the enlargement of spleen and LN after vaccination revealed a significant immunologic response to cancer. The increased numbers of immune system cells fighting cancer antigens made the two organs expand and become "swollen." As shown in FIG. 3A, the total numbers of cells increased dramatically for the vaccinated (V) and vaccinated/challenged (VC) mice when compared to the control groups (C) for the spleen, LN, and cryogels. The increase number of cells remained relatively high within the first 2 weeks post vaccination and started to noticeably drop by day 13 impaired with a reduction of immunologic and inflammatory responses.

Macroporous cryogel matrices were fabricated for controlled release of GM-CSF to recruit and house host DCs, and with an interconnected porous structure that allows for cell infiltration and subsequently present cancer antigens (irradiated B16F10 melanoma cells) and danger signals (CpG-ODN) to activate the resident DCs and dramatically enhance their homing to lymph nodes and proliferation. Matrices were loaded with 3 mg of GM-CSF and injected into the subcutaneous pockets of C57BL/6J mice. FIG. 3B indicates that the cryogel vaccine controls or therapeutically alters immune cell trafficking and activation in the body. Within the first 10 d post vaccination, a large number of DCs are recruited to the vaccine site. As these activated DCs may home to the inguinal lymph nodes and spleen, present antigens to naïve T cells, and stimulate and expand specific T-cell populations that elicit anti-tumor responses, the total number of CD11c(+) DCs is inversely proportional to the total number of CD3(+) T cells. FACS analysis of cells infiltrating the vaccine site revealed a significant CD3(+) T cell response peaking at day 13. Local CD3(+) T cell numbers dropped sharply by day 24 and were negligible at day 30.

These cryogel matrices released approximately 20% of their bioactive GM-CSF load within the first 5 days, followed by slow and sustained release of bioactive GM-CSF over the next 10 days (FIG. 8, cryogel A); this release profile was chosen to allow diffusion of the factor through the surrounding tissue to effectively recruit resident DCs. Cryogels can be successfully used for specific spatiotemporal delivery of several drugs, as the incorporation of a second biomolecule (CpG-ODN) did not alter the release profile of GM-CSF over time (FIG. 8, cryogel B). However, slowly degrading PLG microspheres integrated in the scaffolds seem to release GM-CSF much more slowly than pure cryogels (5% vs 24% release at day 14). Hybrid cryogel have been created as a potential carrier for controlled delivery of hydrophobic and/or low molecule weight drugs. Our results not only provide a new strategy for delivery drugs from an injectable 3-D preformed macroporous scaffolds as a sustained-release drug carrier but also open an avenue for the design of new hybrid injectable hydrogels.

Example 6

Injectable Biodegradable Cryogels as a Gene Delivery System

Nonviral gene delivery systems based upon polycation/plasmid DNA complexes are gaining recognition as an alternative to viral gene vectors for their potential in avoiding immunogenicity and toxicity problems inherent in viral systems. Studies were carried out to determine the feasibility of using a controlled release system based on encapsulated condensed plasmid DNA in injectable cryogels to achieve gene transfer in the surrounding tissues after injection. A unique feature of the cryogel-based gene delivery system is the biodegradability of the polymeric system, which can provide a sustained release of DNA at different rates depending on the polymer, cross-link density, mass fraction, and porosity created during the cryogelation process. Encapsulated DNA complexed with polyethylenimine (PEI), a nondegradable cationic polymer known to be an effective gene carrier, and naked PEI/DNA complexes, which were prepared at a ratio of 7:1 (PEI:DNA) were injected subcutaneously on the lower back of naïve mice using luciferase as a reporter gene (FIG. 9). At 1 day after injection, encapsulated PEI/DNA displayed strong bioluminescence providing the highest transgene expression at ~10 photons/s, about two-order of magnitude higher than that produced by naked PEI/DNA. After 10 days, the expression levels for naked PEI/DNA were about the same as day 1 but increased by 1 order of magnitude when released in a controllable fashion from the cryogels. Till 29 days, encapsulated PEI/DNA still provided a level of transgene expression at ~$10^7$ photons/s, similar to that observed at previous time points. This level was significantly higher than those offered by naked PEI/DNA.

In this study, subcutaneous gene delivery allowed gene expression on the lower back of naïve mice, although the distribution pattern and intensity was vehicle-dependent. Naked PEI/DNA complexes produced limited bioluminescence (signal nearly above background), probably because of its vulnerability to DNAses. However, encapsulated PEI/DNA complexes in cryogels used in this study provided a targeted and sustained high level of gene expression around the injection site for at least 3 weeks. These findings indicate that a 3-D macroporous scaffold may facilitate sustained release and efficient cell transfection of polymer/DNA complexes.

In summary, the present approach has demonstrated that cryogels promote gene transfection to surrounding cells in the subcutis of mice, with an efficiency superior in terms of prolonged gene expression to naked DNA. The results establish an injectable delivery system as an effective gene carrier applicable to program or treat targeted cells.

Example 7

Immunologically Active Injectable Sponges

In this example, a novel cell-based immunotherapy for cancer was developed with the aim of enhancing anti-tumor immunity, reducing ex vivo cell manipulation, preventing repetitive vaccination, and minimizing invasiveness during administration. For this cell-based immunotherapy, a minimally invasive sponge-based vaccine was designed, containing living irradiated tumor cells along with immunomodulatory factors for the prophylactic treatment of melanoma. In the framework of scaffold-based cancer immunotherapy, macroporous 3D alginate cryogels were prepared using MA-alginate by the process of cryopolymerization at −20° C. using a free-radical cross-linking mechanism. During cryotropic gelation, most of the solvent (water) was frozen, and the dissolved solutes (macromonomers, immunomodulator agents, and initiator system) were concentrated in small semifrozen regions called nonfrozen liquid microphase, in which the free-radical cryopolymerization and gelation proceeded with time (FIG. 5A). After complete polymerization, and when subsequently incubated at room temperature (RT) and washed with water to remove unreacted polymeric precursors, the ice crystals melted and left behind a system of large, continuously interconnected macropores throughout the entire cryogel construct (FIGS. 5B-C). Irradiated tumor cells (3500 rads) were initially seeded in sterilized cryogels (FIG. 5A), resulting in cells being homogeneously distributed in gel pores due to the unique interconnected macroporous network. Cryogels were further modified with RGD peptides to enhance tumor cell attachment by way of integrin-mediated cell adhesion motifs for cell-surface antigen display. RGD modification of alginate cryogels enhanced attachment and spreading of cells after 6 h incubation prior to vaccination (FIG. 5D). Autologous tumor cells are a source of tumor-associated antigens (TAA) for vaccination purposes, since, by definition, all relevant candidate TAA should be contained within them. A unique feature of these cryogels is that when an appropriate mechanical force is applied, the gel will shear-collapse, resulting in a biomaterial that flows through a conventional-gauge needle. Unlike traditional nanoporous hydrogels, which are rather brittle, MA-alginate cryogels are elastic, soft, sponge-like materials that can withstand large deformations and can be easily compressed to a fraction of their sizes without being mechanically damaged. See Bencherif S A et al. Proc. Natl. Acad. Sci. USA. 2012; 109:19590-5. Shape-defined macroporous alginate-based scaffold vaccines prepared with a square-shape size were successfully passed through a surgical needle without mechanical fracture or cell dispersion. See id. After the shear force is removed, the scaffolds quickly recovered their original shapes once placed subcutaneously (FIGS. 14A-B).

Macroporous alginate sponges were designed to present GM-CSF, danger signals, and cancer antigens in a defined spatiotemporal manner in vivo and serve to as a residence for recruited dendritic cells as they are programmed. GM-CSF was physically encapsulated (85% efficiency) into cryogels through the crosslinking process. Cryogels were successfully used to control the spatiotemporal delivery of several biomolecules (adjuvant and cytokine), as the incorporation of a second immunostimulatory agent (CpG-ODN) did not alter the release profile of GM-CSF over time (FIG. 15B), although the encapsulation efficiency was slightly lower (75%). Similarly to GM-CSF, TLR-activating CpG-ODN was physically immobilized within the polymer network of alginate and the encapsulation efficiency (approximately 45%) was independent of the incorporation of GM-CSF (FIG. 15C). The inferior encapsulation efficiency of negatively charged CpG-ODN could be attributed to a combination of its low molecular mass coupled with electrostatic repulsions due to negatively charged alginate chains. These matrices released approximately 80% of their bioactive GM-CSF and CpG-ODN loads within the first 4 days, followed by slow and sustained release of the bioactive immunostimulatory factors over the next month (FIGS. 15B-D); these release profiles were chosen to enable diffusion of the factors through the surrounding tissue to effectively recruit and activate resident dendritic cells.

Figure 16:
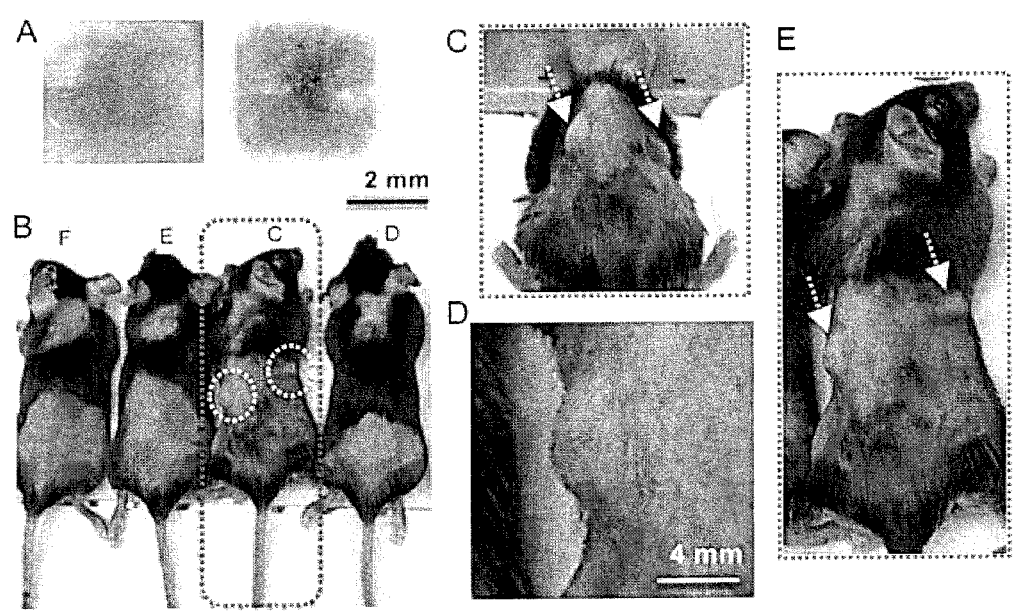

Next, experiments were performed to determine whether the cryogel vaccines were immunologically active. Following vaccination, a local progressive swelling at the vaccination injection site was observed within the first two weeks, which is indicative of a strong inflammatory response and recruitment of immune cells (FIG. 16). As DC are key players in the defense against cancer because of their role in T cell priming and T helper differentiation, changes in their phenotype upon exposure to CpG-ODN-loaded cryogels in vitro were detected. To this end, isolated bone marrow-derived DC (BMDC) (FIG. 17A) that were 97% viable (FIG. 18) and with at least 90% of cells staining positive for CD11c were exposed to cryogels or conditioned media (FIG. 17B). Approximately 60% of BMDC (group C, FIG. 17C) exposed to CpG-loaded cryogels stained positive for CD86 and MHCII, similarly to the positive control (group D, FIG. 17C) of BMDC cultured in medium supplemented with CpG-ODN. However, similar to the negative control (group A, FIG. 3C), the cells (group B, FIG. 17C) cultured with blank cryogels did not activate BMDC. In addition, the upregulation of interleukin (IL)-12 secretion by BMDC was investigated. Activated DC are known to generate signals, such as the IL-12 cytokine, that alert the immune system to potentially dangerous material and modulate subsequent lymphocyte activation and differentiation. The stimulation from released CpG-ODN induced activation of immature BMDC, as indicated by a significant increase of IL-12 production (233 pg/mL). This is in contrast to the adjuvant-free cryogels, which were not immunogenic and led to a low concentration of IL-12 (9 pg/mL). See FIG. 17D. This data shows that the cryogels are not only able to release CpG-ODN, but are immunogenic since they have the potential to activate resident DC within and around the matrix.

To check the capacity of the cryogel sponges to promote cellular infiltration in situ, blank cryogels and their nanoporous counterparts were implanted into the subcutaneous pockets of C57BL/6J mice. After 1 day, the scaffolds were explanted and the total number of infiltrated cells quantified. Cryogels facilitated substantial cellular infiltration when compared with nanoporous hydrogels, as a total number of $6\times10^6$ cells were recruited to the cryogels as opposed to $0.2\times10^6$ cells recruited to nanoporous hydrogels, representing an increase of 2900%. Cryogels have an interconnected macroporous architecture, which is advantageous over nanoporous hydrogel scaffolds with respect to their ability to facilitate cellular infiltration and trafficking.

Further, selective cell recruitment and spatially controlled cell homing was tested. The ability of the cryogels to selectively recruit and home DC at the vaccination site was tested. GM-CSF loaded cryogels were used to provide a 3-D matrix in the surrounding tissue and regulate dendritic-cell recruitment for their activation and subsequent dispersion (FIG. 19A). Since 80% of GM-CSF was released from the scaffolds within the first few days following injection, the capacity of the cryogel vaccines to recruit and host DC after only one day post-injection was determined. Cryogel sponges loaded with 1.5 μg of GM-CSF were injected into the subcutaneous pockets of C57BL/6J mice. Histological analysis at day 1 revealed that the total cellular infiltration into cryogels (FIGS. 19B and 19E) was significantly enhanced compared with the control (no GM-CSF incorporated; FIG. 19B-C). Fluorescence-activated cell sorting (FACS) analysis for $CD11b^+$ $CD11c^+$ DC showed that GM-CSF increased not only the total resident cell number but also the percentage of cells that were dendritic cells (FIGS. 19C-E and 20). Surprisingly, the number of dendritic cells residing in the material as a result of GM-CSF delivery was 3 times higher than the number of dendritic cells that are commonly programmed and administered by ex vivo protocols (~$10^6$ cells). GM-CSF delivery promoted greater cellular penetration into the cryogel sponges, as indicated by the measurement of DC numbers (FIG. 19D) and histological analysis (FIGS. 19D-E), thereby allowing for the subsequent programming of resident DC precursors and DC.

Example 8

Autologous Tumor Cell Vaccines

Creating an infection-mimicking microenvironment by appropriately presenting exogenous cytokines (e.g., GM-CSF) and danger signals (e.g., CpG-ODN) in concert with antigen-displaying cells may provide an avenue to precisely control the number and timing of DC trafficking and activation in situ—this example describes experiments to test this concept. At different time points post scaffold-based vaccine injection, cells were isolated from the cryogels and from the surrounding tissues, spleen, and lymph nodes (LN) for cell counting and fluorescence-activated cell sorting (FACS) analysis in order to determine the overall number of cells and percentage of DC ($CD11c^+$ cells) and T cells ($CD3^+$ cells) (FIGS. 7A-B). A significant immunologic response to the vaccines was reflected in the number of cells infiltrating the vaccine site along with the enlargement of the spleen and lymph node (FIG. 21). The total numbers of cells increased dramatically for the vaccinated (V) and vaccinated/challenged (VC) mice when compared to the control groups (C) for the spleen, LN, and cryogels (FIG. 7A). The increased number of cells remained relatively high within the first 2 weeks following vaccination and started to noticeably drop by day 13.

As described previously, macroporous cryogel matrices were fabricated for controlled release of GM-CSF to recruit and house host DC. The interconnected porous structure that allows for cell infiltration and the presentation of cancer antigens (irradiated B16F10 melanoma cells) and danger signals (CpG-ODN) that activates the resident DC and dramatically enhances their proliferation and homing to lymph nodes. FIGS. 7A-B show that the cryogel vaccine was able to control immune cell trafficking and activation in the body. Within the first 2 weeks post vaccination, a large number of DC were recruited to the vaccine site (FIG. 7B). These activated DC could then home to the inguinal lymph nodes and spleen, present antigens to naïve T cells, and stimulate and expand specific T-cell populations that elicit anti-tumor responses. $CD11c^+$ DC were rapidly and massively recruited and housed at the vaccine site, peaking at day 9, indicating that this cryogel vaccine provides a supportive microenvironment for cell-trafficking during the immune response. Later, DC were subsequently released over time while being substituted with $CD3^+$ T cells (FIG. 7B). FACS analysis of cells infiltrating the vaccine site revealed a significant $CD3^+$ T cell migration peaking at day 13. Local $CD3^+$ T cell numbers dropped sharply by day 24 and were negligible at day 30, likely due to antigen clearance (FIG. 7B).

Example 9

Cryogel Vaccines Promote CD8+ DC, Plasmacytoid DC and CD8+ T Cells while Reducing FoxP3+ Cell Numbers In order to better understand the cellular response to the cryogel vaccines, the DC and T cell types at the vaccine site, draining lymph nodes, and spleen were examined at the peak of cell infiltration along with cytokine expression at the vaccine site (FIGS. 22A-G). Similarly to the examples above, three different conditions were tested: blank cryogels (C: control), cryogel vaccines with CpG-ODN/GM-CSF (V: vaccinated mice), and cryogel vaccines with CpG-ODN/GM-CSF challenged with tumor cells six days later (VC: vaccinated/challenged). Analysis was performed at three sites: cryogel localization, draining lymph nodes, and spleen. Nine days following vaccination, the number of CD11c+ cells as well as the number of plasmacytoid and CD8+ DC in the vaccinated groups at the implantation site and the draining lymph node were greater than that for the blank cryogel group (FIGS. 22A-B). In the spleen, the mean number of DC, plasmacytoid DC, and CD8+ DC for the vaccinated conditions was higher, but the difference does not achieve statistical significance (FIG. 22C). In the lymph node, there was a greater number of plasmacytoid DC in the vaccinated/challenged group in comparison to the vaccinated group, otherwise the number of DC were similar for both groups at the different sites. For both of the vaccinated groups at all of the sites examined, plasmacytoid DC represented greater than 50% of all of the DC while CD8+ DC constituted a quarter to a third of the remaining DC. This set of data demonstrates that these cancer vaccines engineered to selectively trigger Toll-like receptors 9 have the potential to lead to increased immunogenicity.

At day 13, the number of CD3+ T lymphocytes in the cryogel sponges and the lymph nodes was greater in the vaccinated animals compared to the animals that received only blank cryogel injections (FIG. 22D). As shown in FIG. 22E, the number of CD8+ T cells was greater in the vaccinated and vaccinated/challenged mice in comparison to the blank control cryogels at all of the investigated sites, however there was no statistical difference between the vaccinated and vaccinated/challenged groups. These data demonstrate that an immune response is triggered after vaccination.

Further, the potency of the cancer vaccine has been associated with the elimination of different metabolic pathways in tumor-associated immune suppression via reduction of the impacts of regulatory T cells (Tregs). Tregs, identified as the FoxP3+ subset of CD4+ T cells, play pivotal roles in controlling the balance between immune stimulation and suppression. The ratio of CD8+ effectors to FoxP3+ T cells at day 23, however, was greater in the vaccinated mice in comparison to the blank controls at all of the sites and in the lymph nodes and cryogels for the vaccinated/challenged mice (FIG. 22F). For the vaccinated animals, in the cryogel sponge, the ratio of CD8+ T cells to FoxP3+ T cells was over 2.5 times greater than in blank cryogels. Overall, there was no significant difference in T cell numbers between the vaccinated and the vaccinated/challenged mice. FoxP3+ Tregs impose critical barriers that were overcome naturally via infection-mimicking cryogel vaccines, allowing the priming of protective antigen-specific CD8+ T cells.

Additionally, at day 13, the cryogels and surrounding tissue for the three conditions were resected, and several biomarkers were measured (FIG. 22G). The concentrations of RANTES, eotaxin, IL-1β, IL-1α, GM-CSF, IL-10, MCP-1α, and MCP-1β were greater in the tissue of the vaccinated animals compared to the animals that received blank cryogels. In particular, the concentration of RANTES (CCL5), a cytokine that plays an active role in recruiting leukocytes into inflammatory sites, was markedly elevated and found to be at least 10-fold higher. Further, the production of a unique combination of cytokines, such as eotaxin, IL-1β, and GM-CSF, were quantified to be over 5 fold greater. Similarly, the concentration of IL-1β, GM-CSF, and MCP-1β biomarkers was greater in the vaccine/challenged group in comparison to the blank control group. These data demonstrate that the biomarker profiles are affected (to varying extents) when vaccinated mice are exposed to tumor cells during challenge. The concentration of IL-12, TNF-α, and INF-α were similar among the groups. There was no difference in the concentrations of cytokines between the vaccinated and the vaccinated/challenged groups.

Example 10

Activity of Cryogel Vaccines in Melanoma Model

The ability of the vaccine to evoke anti-tumor immunity was next tested in the prophylactic setting. GM-CSF and CpG-ODN can be released in a sustained fashion to recruit and host DC, and subsequently present cancer antigens from the irradiated cells and danger signals to activate resident naïve DC and promote their homing to the lymph nodes, which is necessary for a robust anti-cancer immune response. Specific and protective anti-tumor immunity was generated with the minimally invasive alginate-based active vaccine, as 80% survival was achieved in animals that otherwise die from cancer within a couple of months (FIG. 23A). This cryogel-based prophylactic vaccine for melanoma induced a strong immunologic memory, as 100% survival was achieved in the rechallenged animals following 126 days post vaccination (FIG. 23C). The cryogel-based vaccines provided a powerful short-term and long-term protective immunity when antigen-displaying cells, adjuvant, and chemoattractant were all combined together. The combination of CpG-loaded cryogel and genetically engineered GM-CSF-secreting tumor cells resulted in synergistic enhancement of cellular-vaccine efficacy in vivo. The induced effect was comparable to that of the cryogel-vaccines during the first tumor challenge. However, cryogel-vaccine performance was more effective during the second tumor challenge; this demonstrates that encapsulating GM-CSF within the polymer scaffold can provide a more suitable spatio-temporal release of cytokines, resulting in long-term active immunological memory. In addition, the benefit of providing a 3D matrix for the housing of recruited dendritic cells while they are programmed was demonstrated by the failure of long-term protection of bolus vaccine formulations consisting of bolus injections of irradiated tumor cells, with and without CpG-ODN (FIG. 23C). The combination of tumor antigen-displaying B16-F10 cells, GM-CSF, and TLR9-activating CpG-ODN in the vaccine matrix was required for optimal tumor protection as a markedly enhanced mouse survival was achieved following two tumor challenges (FIG. 23D).

The ability of continuous dendritic cell recruitment and programming to generate an immune response was next tested in the melanoma model. The scaffold-based vaccines provided significant protection, especially when GM-CSF was released from the device. Animal survival increased from 30% to 80% when mice were vaccinated with sponges loaded with GM-CSF transduced tumor cells as opposed to regular tumor cells (FIG. 23A). This infection-mimicking material induced better immune protection than that obtained with previously reported cell-based therapies. See Dranoff G et al. Proc. Natl. Acad. Sci. USA. 1993; 90:3539-43; and Dranoff G. Immunol. Rev. 2002; 188:147-54. Materials presenting CpG-ODN or GM-CSF alone with tumor cells resulted in only a 70% and 10% survival during the first tumor challenge, respectively, and only a 50% overall survival during the second tumor challenge for the CpG-ODN loaded cryogel vaccine, indicating the benefit of recruiting dendritic cells with GM-CSF for long-term protection (FIGS. 23C-D). Except for the GM-CSF-secreting B16-F10 cells vaccine, mice immunized with the different regimens including TLR-activating CpG-ODN displayed delay in time of tumor appearance, significantly retarded tumor growth, and prolonged survival (FIGS. 23A-B). Particularly, vaccination of mice with the cryogel vaccine containing both immunomodulators (GM-CSF and CpG-ODN) significantly decreased the rate of tumor progression (FIG. 23B), and improved life expectancy over controls was observed (FIG. 23A). In contrast, a single treatment with irradiated, GM-CSF-secreting B16-F10 cells, a cell therapy now in clinical trials, attenuated tumor growth similarly to CpG-ODN loaded cryogel vaccines; however, the survival rate was significantly reduced compared to vaccines containing both immunomodulators, 30% vs. 80% (FIGS. 23A-B). Injecting tumor cell-loaded sponges without immunomodulatory factors resulted in little immune protection suggesting that the material without GM-CSF and CpG-ODN was inert to DC. However, injectable alginate sponges containing both immunostimulatory factors and syngeneic irradiated tumor cells provided a suitable residence to recruit and program DC to elicit a potent immunity capable of preventing melanoma. To ensure that the vaccines are safe as well as effective, explanted implants and organs were sent for toxicological analysis. The pathology report indicated no evidence of pathologic changes, although minimal granulomas were located at the vaccine implants, suggesting long-term effectiveness. The absence of toxicity to the liver, kidney, or other organs suggests that the scaffold-based vaccines have minimal adverse effects and no safety concerns.

Example 11

Cryogel Vaccines for Anti-Tumor Immunity Against Breast Cancer

Several reports from experimental models and clinical studies have described that HER-2/neu is an immunogenic molecule since it generates antibody responses and activation of HER-2/neu peptide-specific cytotoxic T lymphocytes and T helpers. Therefore, here the HER-2/neu-specific humoral response was studied by investigating HER-2/neu-specific IgG antibody production in response to the HER-2/neu-based cryogel breast cancer vaccine in BALB/c mice.

The presence of HER-2/neu-specific IgG antibody was assessed by flow cytometric analysis on CT26-Her-2/neu colon adenocarcinoma cells incubated with mouse sera at different time points prior to challenge (days 14 and 28) and 1 week post-challenge (day 37), followed by fluorescein isothiocyanate (FITC)-conjugated anti-mouse antibody. The vaccines were found to be safe and effective in raising vaccine type-dependent HER-2/neu immunity, as observed with HER-2/neu-specific IgG stimulation in immunized mice (groups 1, 2, 3, 4, and 5 of FIG. 24), indicating a neu-specific Th2-type response.

Throughout the course of the study, low HER-2/neu-specific antibody titers were detected in the sera of unvaccinated mice (groups 7 and 8) or mice immunized with blank cryogels (group 6). Mice vaccinated with HER-2/neu positive breast cancer cells did not induce a strong neu-specific IgG antibody response at day 14. However, from day 28, cryogels with tumor cell-associated antigens (groups 2 and 3) resulted in an approximately 70-fold increase of HER-2/neu-specific IgG antibody when compared to controls (groups 5, 6, and 7) and up to a 7-fold increase of HER-2/neu-specific IgG antibody when compared to cryogels with tumor lysate-associated antigens (group 1) and to bolus injection vaccines (groups 4 and 5) (FIG. 24).

Specific and protective anti-tumor immunity was generated with these minimally invasive alginate-based active vaccines. As shown in FIG. 25, the cryogel-based prophylactic vaccines for breast cancer induced a strong humoral immunologic response. In particular, at day 78 (ongoing study), 80% and 100% survival was achieved in animals from groups 2 and 3, respectively, that otherwise would die from cancer within a month (groups 6 and 7). Bolus injections of vaccine also promoted a robust anti-HER-2/neu immune response, as 80% of mice (groups 4 and 5) were still alive at day 78 following animal challenge (FIG. 25). However, cryogel vaccines with tumor lysate-associated antigens induced a limited protective anti-HER2/neu immune response, as the mice died within 2 months.

Taken together, this unique and flexible cryogel vaccine system is a promising cell-based immunotherapy approach for the treatment of breast cancer using allogeneic tumor-cells. The data presented herein demonstrates that the HER-2/neu-based cryogel vaccine provides a more potent prophylactic protection against mammary cancer than the positive control (G-vax vaccine) in mice, which is in agreement with the higher anti-HER-2/neu antibody levels detected in the blood. This data shows that the cryogel-based vaccine is over 80% effective. To test sustained tumor immunity to prevent relapse, at day 100 following immunization, the mice will be rechallenged with $10^5$ HER-2/neu-overexpressing breast cancer cells and monitored for the onset of tumor development.

Example 12

Bulk Cryogel Behavior

The bulk behavior of cryogels formed with GelMA macromonomer concentrations between 1 and 2% (w/v) was studied to assess their suitability as injectable preformed hydrogels. 1.0% cryoGelMA showed a superior interconnected porosity of 91±2%, relative to 1.5 and 2.0% gels which had mean interconnected porosities of less than 5% (FIG. 26C). Mechanical testing revealed that cryogels made with 1.5% and 2.0% GelMA led to brittle gels that could not undergo large strains (FIGS. 28A-C). However, 1.0% cryoGelMA gels demonstrated complete shape recovery when released after deformation to high strains (FIG. 29A). 1.0% cryoGelMA gels collapsed dramatically when water was wicked away from the interconnected pores, and rapidly reassumed their previous shape when rehydrated (FIG. 29B). Due to their ability to undergo large deformation and allow rapid influx/efflux of water, the potential of 1.0% cryoGelMA gels to be injected through a conventional needle was next analyzed. Disc-shaped cryoGelMA gels (5 mm diameter, 2 mm thickness) could collapse, travel through a 16 G needle (1.65 mm inner diameter), and quickly (260±80 ms, n=10) return to their original geometry after exiting the needle (FIG. 29C). Based on these findings, 1.0% cryoGelMA was used in gelatin cryogel studies described herein.

Example 13

Gelatin Cryogel Scaffold Architecture

Since cell trafficking within scaffolds is subject to sufficient pore size (>10 μm) and interconnectivity, the microarchitecture of cryoGelMA gels was next assessed. Scanning electron microscopy (SEM) revealed a highly porous surface and scaffold interior (FIG. 30A). Since the processing used to prepare the hydrogels for SEM can cause shrinkage, 2-photon fluorescence imaging of rhodamine-cryoGelMA was used to study the structure of these scaffolds in their hydrated state (FIG. 30B). The gels demonstrated a highly interconnected pore structure, with the pore diameter increasing with depth into the scaffold from the surface to the interior, likely due to a temperature gradient within the scaffold during the freezing process. The hydrated pore size from the scaffold surface to a depth of 350 µm varied between 20-300 µm. Together these data indicate that cryoGelMA has an interconnected porous structure with pore sizes compatible with cell trafficking, movement, or migration.

Example 14

Gelatin Cryogel Cell Compatibility

The suitability of cryoGelMA gels as a substrate for cell attachment and growth was also tested. Free fluid was first wicked from cryoGelMA gels, and a cell suspension of NIH 3T3 fibroblasts, a cell line commonly used for cell compatibility testing, was then placed on the gels. 3T3 cells were found distributed throughout the scaffold volume, as seen with 2-photon microscopy (FIG. 31A). To study the interaction of cells with cryoGelMA, SEM was used to assess 3T3 cell morphology at the scaffold surface (FIG. 31B). 3T3 cells attached to the cryoGelMA surface and assumed their characteristic spindle-like morphology after 1 day of culture. Subsequent culture for 2 days led to the formation of a monolayer of cells on the surface of the cryogel, and deposition of extracellular matrix by the fibroblasts on the cryogel surface (FIGS. 32A-B). Cell coverage of the cryogel surface was also seen to increase over the culture period using fluorescence microscopy, and high cell viability was maintained on the scaffold surface (FIGS. 33A-B). Cryogels were also seen to contract slightly over the 3 day culture period, indicating that 3T3 cells were exerting traction forces on the cryogel. Consistent with this observation, F-actin staining of histological sections showed actin stress fiber formation within cells in the scaffold interior (FIG. 31C).

Retrieval and analysis of cells from cryoGelMA scaffolds over the culture period showed maintenance of >90% cell viability (FIG. 31D). Cell number and metabolic activity increased over the culture period (FIG. 31D). Cell proliferation on cryoGelMA scaffolds was further studied by characterizing new DNA synthesis. BrDU incorporation after 1 d of culture showed cells were proliferating on cryoGelMA gels, albeit at a lower rate than cells cultured on tissue culture polystyrene (FIG. 34), as is expected when a high density of cells is cultured in a 3D environment relative to a sparse 2D culture.

To assess whether proliferation occurred uniformly on cryoGelMA scaffolds, histological sections were stained after pulsing cell-laden scaffolds with EdU (FIG. 31E). EdU-positive nuclei could be seen throughout the scaffold thickness. Collectively, these results indicate that cryoGelMA provides a substrate for cell attachment, sustaining cell viability, and allowing cell proliferation.

Example 15

Enzymatic Degradation of Gelatin Cryogels In Vitro

Studies were also performed to test whether modification of gelatin with methacrylate groups and subsequent cryopolymerization preserved the inherent enzymatic degradability of gelatin. Fluorescent cryogels were first incubated in the presence of 25 U/ml collagenase type II, and fluorescence in the supernatant was monitored as a proxy for gel degradation (FIG. 35A). This analysis revealed that cryoGelMA gels could be degraded completely in the presence of collagenase over a period of 10 days.

The ability of the mammalian gelatinases, MMP-2 and -9, to degrade gelatin with a high degree of methacrylation was next assessed. GelMA was incorporated as a substrate into a polyacrylamide gel and zymography was performed with recombinant mouse and human gelatinases (FIG. 35B). After Coomassie staining of the gel, bands of GelMA degradation were observed with all of the enzymes tested, indicating preservation of enzymatic degradability following methacrylation of gelatin. Short-term degradation studies of rhodamine-cryoGelMA gels by activated mammalian gelatinases were also conducted (FIG. 35C). All of the enzymes tested were seen to accelerate gel degradation compared to buffer alone. Together these results demonstrate that cryoGelMA is enzymatically degraded by collagenase and mammalian gelatinases.

Example 16

In Vivo Injection of Gelatin Cryogels

The in vivo response to cryoGelMA scaffolds was also explored. CryoGelMA gels injected subcutaneously through a conventional needle regained their original shape under the skin (FIGS. 36A-B). Implanted scaffolds were covered by a thin fibrous capsule after 2 months and underwent a reduction in bulk size. H&E staining revealed mild inflammation at the scaffold border after 1 week with the presence of mononuclear phagocytes and lymphocytes and sparse infiltration of the scaffold by mononuclear cells (FIG. 36C). At 2 months post-implant, a foreign body reaction was present at the scaffold border with the presence of macrophages, multinucleated giant cells, fibroblasts, and collagen deposition (FIG. 36D). The interior of the scaffold was acellular at 2 months and no adverse reaction was seen in the skin. These results show that cryoGelMA gels induce only mild acute inflammation after injection followed by a foreign body reaction.

Example 17

In Vivo Cell Recruitment to Gelatin Cryogels

As a demonstration of the utility of cryoGelMA in vivo, the ability of this material to release a chemotactic protein and allow host cell infiltration into the scaffold was analyzed. GM-CSF, a cytokine involved in immune cell development that is being widely explored in cancer vaccines, was used as a recruitment signal for immune cells (FIG. 37A). Direct incorporation of GM-CSF in the prepolymer solution led to 84±2% encapsulation efficiency after cryopolymerization. GM-CSF is likely to be released by both diffusion out of the cryogel walls and by degradation of the walls in vivo. To study the diffusive element of this process, in vitro GM-CSF release over a period of 14 days in DPBS containing 1% BSA was analyzed (FIGS. 37B-C). Sustained release of GM-CSF was seen over this period, with an initial burst release followed by a more constant release rate. The total amount of GM-CSF released over this period accounted for only ~2% of the amount encapsulated, indicating that gel degradation mediates payload delivery.

GM-CSF-releasing cryoGelMA was injected subcutaneously to assess cell recruitment Implantation of GM-CSF-releasing scaffolds into C57/B16J mice led to recruitment of ~20× more live cells at 14 days post-implant relative to blank cryoGelMA (FIG. 37D). H&E staining showed thin fibrous capsule formation, and minimal cellular infiltration of blank scaffolds, whereas GM-CSF-releasing gels were surrounded by a thick fibrous capsule and contained a large primarily granulocytic cellular infiltrate (FIG. 37E). These results show that cryoGelMA delivers a chemotactic protein and allows cell infiltration and recruitment in vivo.

In addition, FIGS. 39A-C depict the massive increase in immune cell recruitment, a key process in immunotherapy using the devices described herein, that occurs when GM-CSF is released from gelatin cryogels. There was a visible accumulation of cells that occurs in cryoGelMA gels when GM-CSF is released from the gel (FIG. 39A-B). A comparison of the size of recovered blank and GM-CSF releasing cryoGelMA gels 17 days after injection into mice shows increased size of the GM-CSF-releasing implants (FIG. 39C). Histology of center of blank cryoGelMA scaffold 14 days after subcutaneous injection in mice shows very few immune cells present in the matrix (FIG. 40A). In contrast, histology of center of GM-CSF releasing cryoGelMA scaffold 14 days after subcutaneous injection in mice shows massive immune cell recruitment filling the scaffold pores (FIG. 40B). Macrophages (a key antigen presenting cell type) are also present at the site of GM-CSF releasing cryoGelMA scaffold injection after 14 days (FIG. 41).

A variety of immune cells are recruited to cryoGelMA at various doses of GM-CSF. Flow cytometric phenotyping of immune cells residing in blank and GM-CSF releasing gelatin cryogels was performed. Doses of 1, 5, and 10 μg of GM-CSF were encapsulated in each cryogel, and cryogels were implanted in the flanks of C57/B16J mice for 14 days. Flow cytometric analysis revealed the presence of roughly the same percentage of granulocytes (CD11b+Gr-1+), macrophages (CD11b+F4/80+), dendritic cells/macrophages (CD11c+CD11b+), and CD4+ cells in all conditions. Further staining revealed that a large fraction of CD4+ cells were CD4+ regulatory T cells (CD4+/(CD25+FoxP3+)) (FIGS. 42A-F).

Blank cryoGelMA gels created mild inflammation that resolved quickly in the absence of GM-CSF. Flow cytometric phenotyping of immune cells resident in gelatin cryogels was performed. Implanted gelatin cryogels were retrieved at day 6 or day 15 post-injection from C57/B16J mice and analyzed by flow cytometry for the percentage of macrophage/dendritic cells and NK cells as a percentage of all live cells. A large fraction of resident cells were macrophages/dendritic cells (CD11b+CD11c+) and natural killer (NK1.1+) cells at day 6, but a significant reduction in these cells was observed by day 15. Staining for CD4+, CD8+, CD19+, and Gr-1+ cells was not substantial at either timepoint.

Example 18

In Vivo Gelatin Cryogel Degradation

The relative degradation of blank- and GM-CSF-cryoGelMA was monitored by in vivo fluorescence imaging of rhodamine-GelMA cryogels. GM-CSF-releasing cryogels degraded much more rapidly than blank cryogels over the course of 18 weeks (FIG. 38A-B). Since MMPs are thought to be key players in gelatin degradation, 7 day implanted scaffolds were assessed for the presence of MMPs using gelatin zymography (FIG. 38C). Degradation bands corresponding to the various molecular weight forms of MMP-2 and -9, were greatly enhanced in GM-CSF-cryoGelMA relative to blank-cryoGelMA. In vivo imaging using an MMP-sensitive fluorescent dye revealed MMP activity was concentrated at the implant site of both blank and GM-CSF-releasing cryogels (FIG. 38D). The magnitude of fluorescent signal from the MMP-sensitive dye at the scaffold site was significantly enhanced in GM-CSF-releasing scaffolds (FIG. 38E). Collectively, these results show that cryoGelMA can be degraded by recruited cells, likely via MMP expression.

The results of the studies described herein show that cryoGelMA is a cell and tissue compatible biomaterial that can be injected in a minimally invasive manner through a conventional needle. CryoGelMA can be degraded by MMPs, is capable of controlled release of proteins, and allows cell trafficking within its interconnected pores. These advantageous properties indicate that cryoGelMA is useful for cell-triggered scaffold remodeling and protein release for applications in biomaterials-based therapy, e.g., immunotherapy such as cancer immunotherapy.

Example 19

CpG Incorporation into cryoGelMA Gels

Three incorporation strategies are used for incorporating CpG oligonucleotides into cryoGelMA gels. A slow release profile of CpG from the material leads to more sustained immune cell activation, increasing vaccine effectiveness. In one strategy, crosslinked gelatin is mixed with free CpG (FIG. 44A). Low electrostatic interactions between CpG and gelatin results in rapid release of CpG if directly incorporated into the gel. A second strategy is to condense the CpG into nanoparticles using cationized gelatin and then cross-linking gelatin (e.g., methacrylated gelatin) will free CpG ODN condensates (FIG. 44B). This strategy is used to slow release of CpG. A third strategy is to use cationized methacrylated gelatin to condense the CpG before incorporation (FIG. 45). The methacrylate groups on the resulting particles allow them to covalently bind to the gel during cryogel formation, localizing the CpG tightly.

Choice of CpG incorporation strategy is employed to tune CpG release rates for optimal effect, e.g., optimal vaccine efficacy. When 12 ug of CpG was incorporated into gelatin cryogels, the predicted release profiles were observed, allowing tuning of CpG release for optimal vaccine efficacy (FIG. 46).

Example 20

CryoGelMA is Immune Neutral in the Absence of GM-CSF

Studies were performed to determine the effect of cryoGelMA gels loaded with or without GM-CSF or CpG on dendritic cell activation. Freshly thawed cryoGelMA gels were vortexed for 1 minute and incubated for 30 minutes in cell culture media. Mouse bone marrow derived dendritic cells were cultured in the conditioned media for 12 hours and analyzed by flow cytometry for activation markers CD40 and CD86. No significant difference was seen in comparison to cells cultured in untreated culture medium (FIGS. 47A-B). CryoGelMA conditioned media does not cause substantial mouse bone marrow derived dendritic cells activation in vitro. In contrast, the positive control, lipopolysaccharide (LPS) did cause substantial dendritic cell activation.

The effect of cryoGelMA gels on the production of inflammatory cytokines by dendritic cells was also assessed. Dendritic cells were seeded on cryoGelMA gels (3D condition). Dendritic cells were also seeded on tissue culture polystyrene (2D condition). LPS was used as a positive control for inducing the production of inflammatory cytokines. CLI is an inhibitor of TLR4, the receptor for endotoxin. See, e.g., Li M. et al., 2006. Mol. Pharmacol., 69:1288-1295. No significant activation of dendritic cells is seen by culturing dendritic cells on the material alone (3D) (FIGS. 48A-C).

Thus, cryoGelMA gels do not cause dendritic cell activation in the absence of GM-CSF or CpG.

Example 21

Seeding of Dendritic Cells in Gelatin Cryogels

CryoGelMA gels were seeded with mouse bone marrow derived dendritic cells. FIG. 49 shows a section of the cryogels containing dendritic cells 48 hours after they were seeded onto the gels.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An injectable device comprising a cell-adhesive, highly crosslinked cryogel composition comprising open interconnected macropores,
   wherein said cryogel composition comprises at least 75% pores,
   wherein said cryogel composition is characterized by shape memory following deformation by compression through a needle,
   wherein said cryogel composition comprises a crosslinked gelatin polymer, wherein said gelatin is methacrylated,
   wherein said cryogel composition comprises a methacrylated gelatin concentration of 0.5% to 1.4% (w/v), and
   wherein said cryogel composition comprises a live attenuated breast cancer cell in one or more of said open interconnected pores.

2. The device of claim 1, wherein the device recruits cells into the cryogel composition upon injection into a subject.

3. The device of claim 2, wherein the cryogel composition is degraded by the recruited cells.

4. The device of claim 1, wherein the cryogel composition is formed by cryopolymerization of methacrylated gelatin.

5. The device of claim 4, wherein the cryogel composition further comprises a methacrylated alginate macromonomer.

6. The device of claim 1, wherein said cryogel composition comprises a biomolecule in one or more of said open interconnected pores.

7. The device of claim 6, wherein said biomolecule comprises a small molecule, nucleic acid, or protein.

8. The device of claim 7, wherein said protein comprises granulocyte-macrophage colony-stimulating factor (GM-CSF).

9. The device of claim 7, wherein said nucleic acid comprises a CpG nucleic acid oligonucleotide (CpG-ODN).

10. The device of claim 1, wherein the device is between 100 um$^3$ to 100 mm$^3$ in size.

11. A method for eliciting an immune response, comprising injecting the device of claim 1 into a subject, wherein an immune response is elicited against the live attenuated breast cancer cell.

12. The method of claim 11, wherein the device is injected into the subject one to 5 times in the lifetime of the subject.

13. The method of claim 11, wherein the injected device comprises at least $0.5 \times 10^6$ immune cells at least 1 day after injection into the subject.

14. The method of claim 11, wherein the injected device comprises $10^7$ or fewer cells 15 days or more after injection.

15. The method of claim 11, wherein the injected device, a tissue within 10 cm of the injected device, or both comprises an elevated level of a cytokine compared to the level of the cytokine at a site in the subject more than 10 cm away from the injected device.

16. The method of claim 11, wherein the device increases the survival time of at least 80% of subjects diagnosed with a cancer by at least 1 month compared to the survival time of untreated subjects, wherein increased survival time is determined by comparing the prognosis for survival in the subjects from a time period prior to administration of the device to the prognosis for survival in the subjects following administration of the device, wherein an increase in predicted survival time indicates that the treatment increased survival of the subjects following administration of the device.

17. The method of claim 11, wherein the device reduces the rate of tumor growth in the subject compared to the rate of tumor growth in an untreated subject.

18. The device of claim 7, wherein said nucleic acid comprises deoxyribonucleic acid (DNA).

19. The device of claim 1, wherein the device is in the shape of a disc, cylinder, square, rectangle, or string.

20. The device of claim 1, wherein said highly crosslinked cryogel composition comprises a crosslinking density of at least 50% polymer crosslinking.

21. The device of claim 1, wherein said highly crosslinked cryogel composition comprises a crosslinking density of at least 50-100% polymer crosslinking.

22. The device of claim 1, wherein said device comprises live attenuated HER-2/neu expressing breast cancer cells.

23. The device of claim 1, wherein said live attenuated breast cancer cell is an irradiated breast cancer cell.

24. The device of claim 1, wherein said cryogel composition comprises macropores having a diameter of 20 μm to 300 μm.

25. A syringe comprising an injectable device comprising a cell-adhesive, highly crosslinked cryogel composition comprising open interconnected pores,
   wherein said cryogel composition comprises at least 75% pores,
   wherein said cryogel composition is characterized by shape memory following deformation by compression,
   wherein said cryogel composition comprises a crosslinked gelatin polymer, wherein said gelatin is methacrylated,
   wherein said cryogel composition comprises a methacrylated gelatin concentration of 0.5% to 1.4% (w/v), and
   wherein said cryogel composition comprises live attenuated breast cancer cells in one or more of said open interconnected pores.

26. The syringe of claim 25, comprising a 16-gauge, an 18-gauge, a 22-gauge, a 24-gauge, a 26-gauge, a 28-gauge, a 30-gauge, a 32-gauge, or a 34-gauge needle.

27. The syringe of claim 25, comprising an 18 to 30-gauge needle.

28. The syringe of claim 26, wherein the device is between 1 mm³ to 50 mm³ in size.

29. The syringe of claim 26, wherein 90% or more of the cancer cells survive passage of the device through the bore of the needle.

30. The syringe of claim 25, wherein said cryogel composition is characterized by shape memory following deformation by compression through a needle, such that said cryogel returns to its original undeformed three-dimensional shape less than one second after compression through the needle.

31. The syringe of claim 25, wherein said cryogel composition comprises macropores having a diameter of 20 μm to 300 μm.

32. The method of claim 11, wherein the device
   (i) comprises live attenuated HER-2/neu expressing breast cancer cells, and
   (ii) increases the level of HER-2/neu-specific IgG antibody in subjects diagnosed with a cancer by approximately 70-fold compared to untreated subjects.

33. The device of claim 1, wherein said cryogel composition is characterized by shape memory following deformation by compression through a needle such that said cryogel composition returns to its original undeformed three-dimensional shape less than one second after compression through the needle.

34. The device of claim 6, wherein said biomolecule comprises a pathogen-associated molecular pattern (PAMP).

35. An injectable device comprising a cell-adhesive, highly crosslinked cryogel composition comprising open interconnected macropores,
   wherein said cryogel composition comprises at least 75% pores,
   wherein said cryogel composition is characterized by shape memory following deformation by compression through a needle,
   wherein said cryogel composition comprises a crosslinked gelatin polymer, wherein said gelatin is methacrylated, and
   wherein said cryogel composition comprises a methacrylated gelatin concentration of 0.5% to 1.4% (w/v).

36. The device of claim 35, wherein said cryogel composition comprises macropores having a diameter of 20 μm to 300 μm.

37. The device of claim 35, wherein said cryogel composition is characterized by shape memory following deformation by compression through a needle, such that said cryogel returns to its original undeformed three-dimensional shape less than one second after compression through the needle.

38. The device of claim 35, wherein said highly crosslinked cryogel composition comprises a crosslinking density of at least 50-100% polymer crosslinking.

39. A syringe comprising the device of claim 35.

* * * * *

UNITED STATES PATENT AND TRADEMARK OFFICE
CERTIFICATE OF CORRECTION

PATENT NO. : 9,675,561 B2
APPLICATION NO. : 14/166689
DATED : June 13, 2017
INVENTOR(S) : Sidi A. Bencherif et al.

It is certified that error appears in the above-identified patent and that said Letters Patent is hereby corrected as shown below:

In the Specification

At Column 1, Lines 28-33, please replace "This invention was made with U.S. Government support under Grant Numbers R01 DE013349, 5R01 DE019917-03, and R01 EB015498 from the National Institutes of Health and Award Number ECS-0335765 from the National Science Foundation. The Government has certain rights in the invention." with -- This invention was made with government support under DE013349 and DE019917 and EB015498 awarded by National Institutes of Health (NIH) and under 0335765 awarded by National Science Foundation (NSF). The Government has certain rights in this invention. --

Signed and Sealed this
Fourth Day of October, 2022

Katherine Kelly Vidal
*Director of the United States Patent and Trademark Office*